(12) United States Patent
Yun et al.

(10) Patent No.: US 8,705,046 B2
(45) Date of Patent: Apr. 22, 2014

(54) METHOD AND APPARATUS FOR PERFORMING OPTICAL IMAGING USING FREQUENCY-DOMAIN INTERFEROMETRY

(71) Applicant: The General Hospital Corporation, Boston, MA (US)

(72) Inventors: Seok-Hyun Yun, Cambridge, MA (US); Brett Eugene Bouma, Quincy, MA (US); Guillermo J. Tearney, Cambridge, MA (US); Johannes Fitzgerald de Boer, Amstelveen (NL)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/720,507

(22) Filed: Dec. 19, 2012

(65) Prior Publication Data
US 2013/0128274 A1 May 23, 2013

Related U.S. Application Data

(63) Continuation of application No. 13/191,885, filed on Jul. 27, 2011, now Pat. No. 8,355,138, which is a continuation of application No. 12/795,529, filed on Jun. 7, 2010, now Pat. No. 8,384,909, which is a continuation of application No. 10/577,562, filed as application No. PCT/US2004/029148 on Sep. 8, 2004, now Pat. No. 7,733,497.

(60) Provisional application No. 60/514,769, filed on Oct. 27, 2003.

(51) Int. Cl.
*G01B 9/02* (2006.01)
*G01B 11/02* (2006.01)

(52) U.S. Cl.
USPC .......................................... 356/479; 356/497

(58) Field of Classification Search
USPC ......... 356/477, 479.497; 250/227.19, 227.27; 385/12
See application file for complete search history.

(56) References Cited

U.S. PATENT DOCUMENTS 2,339,754 A   1/1944   Brace
3,090,753 A   5/1963   Matuszak et al.
(Continued)

FOREIGN PATENT DOCUMENTS

CN   1550203   12/2004
DE   4105221   9/1991
(Continued)

OTHER PUBLICATIONS

Office Action dated Dec. 9, 2008 for U.S. Appl. No. 09/709,162.
Office Action dated Dec. 23, 2008 for U.S. Appl. No. 11/780,261.
Office action dated Jan. 9, 2010 for U.S. Appl. No. 11/624,455.
Office Action dated Feb. 18, 2009 for U.S. Appl. No. 11/285,301.
(Continued)

*Primary Examiner* — Michael A Lyons
(74) *Attorney, Agent, or Firm* — Andrews Kurth LLP

(57) ABSTRACT

An apparatus and method are provided. In particular, at least one first electro-magnetic radiation may be provided to a sample and at least one second electro-magnetic radiation can be provided to a non-reflective reference. A frequency of the first and/or second radiations varies over time. An interference is detected between at least one third radiation associated with the first radiation and at least one fourth radiation associated with the second radiation. Alternatively, the first electro-magnetic radiation and/or second electro-magnetic radiation have a spectrum which changes over time. The spectrum may contain multiple frequencies at a particular time. In addition, it is possible to detect the interference signal between the third radiation and the fourth radiation in a first polarization state. Further, it may be preferable to detect a further interference signal between the third and fourth radiations in a second polarization state which is different from the first polarization state. The first and/or second electro-magnetic radiations may have a spectrum whose mean frequency changes substantially continuously over time at a tuning speed that is greater than 100 Tera Hertz per millisecond.

14 Claims, 20 Drawing Sheets

(56) References Cited

U.S. PATENT DOCUMENTS

| | | |
|---|---|---|
| 3,601,480 A | 8/1971 | Randall |
| 3,856,000 A | 12/1974 | Chikama |
| 3,872,407 A | 3/1975 | Hughes |
| 3,941,121 A | 3/1976 | Olinger |
| 3,973,219 A | 8/1976 | Tang et al. |
| 3,983,507 A | 9/1976 | Tang et al. |
| 4,030,827 A | 6/1977 | Delhaye et al. |
| 4,030,831 A | 6/1977 | Gowrinathan |
| 4,140,364 A | 2/1979 | Yamashita et al. |
| 4,141,362 A | 2/1979 | Wurster |
| 4,224,929 A | 9/1980 | Furihata |
| 4,295,738 A | 10/1981 | Meltz et al. |
| 4,300,816 A | 11/1981 | Snitzer et al. |
| 4,303,300 A | 12/1981 | Pressiat et al. |
| 4,428,643 A | 1/1984 | Kay |
| 4,479,499 A | 10/1984 | Alfano |
| 4,533,247 A | 8/1985 | Epworth |
| 4,585,349 A | 4/1986 | Gross et al. |
| 4,601,036 A | 7/1986 | Faxvog et al. |
| 4,607,622 A | 8/1986 | Fritch et al. |
| 4,631,498 A | 12/1986 | Cutler |
| 4,639,999 A | 2/1987 | Daniele |
| 4,650,327 A | 3/1987 | Ogi |
| 4,734,578 A | 3/1988 | Horikawa |
| 4,744,656 A | 5/1988 | Moran et al. |
| 4,751,706 A | 6/1988 | Rohde et al. |
| 4,763,977 A | 8/1988 | Kawasaki et al. |
| 4,770,492 A | 9/1988 | Levin et al. |
| 4,827,907 A | 5/1989 | Tashiro et al. |
| 4,834,111 A | 5/1989 | Khanna et al. |
| 4,868,834 A | 9/1989 | Fox et al. |
| 4,890,901 A | 1/1990 | Cross, Jr. |
| 4,892,406 A | 1/1990 | Waters |
| 4,905,169 A | 2/1990 | Buican et al. |
| 4,909,631 A | 3/1990 | Tan et al. |
| 4,925,302 A | 5/1990 | Cutler |
| 4,928,005 A | 5/1990 | Lefevre et al. |
| 4,940,328 A | 7/1990 | Hartman |
| 4,965,441 A | 10/1990 | Picard |
| 4,965,599 A | 10/1990 | Roddy et al. |
| 4,966,589 A | 10/1990 | Kaufman |
| 4,984,888 A | 1/1991 | Tobias et al. |
| 4,993,834 A | 2/1991 | Carlhoff et al. |
| 4,998,972 A | 3/1991 | Chin et al. |
| 5,039,193 A | 8/1991 | Snow et al. |
| 5,040,889 A | 8/1991 | Keane |
| 5,045,936 A | 9/1991 | Lobb et al. |
| 5,046,501 A | 9/1991 | Crilly |
| 5,065,331 A | 11/1991 | Vachon et al. |
| 5,085,496 A | 2/1992 | Yoshida et al. |
| 5,120,953 A | 6/1992 | Harris |
| 5,121,983 A | 6/1992 | Lee |
| 5,127,730 A | 7/1992 | Brelje et al. |
| 5,197,470 A | 3/1993 | Helfer et al. |
| 5,202,745 A | 4/1993 | Sorin et al. |
| 5,202,931 A | 4/1993 | Bacus et al. |
| 5,208,651 A | 5/1993 | Buican |
| 5,212,667 A | 5/1993 | Tomlinson et al. |
| 5,214,538 A | 5/1993 | Lobb |
| 5,217,456 A | 6/1993 | Narciso, Jr. |
| 5,228,001 A | 7/1993 | Birge et al. |
| 5,241,364 A | 8/1993 | Kimura et al. |
| 5,248,876 A | 9/1993 | Kerstens et al. |
| 5,250,186 A | 10/1993 | Dollinger et al. |
| 5,251,009 A | 10/1993 | Bruno |
| 5,262,644 A | 11/1993 | Maguire |
| 5,275,594 A | 1/1994 | Baker |
| 5,281,811 A | 1/1994 | Lewis |
| 5,283,795 A | 2/1994 | Fink |
| 5,291,885 A | 3/1994 | Taniji et al. |
| 5,293,872 A | 3/1994 | Alfano et al. |
| 5,293,873 A | 3/1994 | Fang |
| 5,302,025 A | 4/1994 | Kleinerman |
| 5,304,173 A | 4/1994 | Kittrell et al. |
| 5,304,810 A | 4/1994 | Amos |
| 5,305,759 A | 4/1994 | Kaneko et al. |
| 5,317,389 A | 5/1994 | Hochberg et al. |
| 5,318,024 A | 6/1994 | Kittrell et al. |
| 5,321,501 A | 6/1994 | Swanson et al. |
| 5,333,144 A | 7/1994 | Liedenbaum et al. |
| 5,348,003 A | 9/1994 | Caro |
| 5,353,790 A | 10/1994 | Jacques et al. |
| 5,383,467 A | 1/1995 | Auer et al. |
| 5,394,235 A | 2/1995 | Takeuchi et al. |
| 5,404,415 A | 4/1995 | Mori et al. |
| 5,411,016 A | 5/1995 | Kume et al. |
| 5,419,323 A | 5/1995 | Kittrell et al. |
| 5,424,827 A | 6/1995 | Horwitz et al. |
| 5,439,000 A | 8/1995 | Gunderson et al. |
| 5,441,053 A | 8/1995 | Lodder et al. |
| 5,450,203 A | 9/1995 | Penkethman |
| 5,454,807 A | 10/1995 | Lennox et al. |
| 5,459,325 A | 10/1995 | Hueton et al. |
| 5,459,570 A | 10/1995 | Swanson et al. |
| 5,465,147 A | 11/1995 | Swanson |
| 5,486,701 A | 1/1996 | Norton et al. |
| 5,491,524 A | 2/1996 | Hellmuth et al. |
| 5,491,552 A | 2/1996 | Knuttel |
| 5,522,004 A | 5/1996 | Djupsjobacka et al. |
| 5,526,338 A | 6/1996 | Hasman et al. |
| 5,555,087 A | 9/1996 | Miyagawa et al. |
| 5,562,100 A | 10/1996 | Kittrell et al. |
| 5,565,983 A | 10/1996 | Barnard et al. |
| 5,565,986 A | 10/1996 | Knuttel |
| 5,566,267 A | 10/1996 | Neuberger |
| 5,583,342 A | 12/1996 | Ichie |
| 5,590,660 A | 1/1997 | MacAulay et al. |
| 5,600,486 A | 2/1997 | Gal et al. |
| 5,601,087 A | 2/1997 | Gunderson et al. |
| 5,621,830 A | 4/1997 | Lucey et al. |
| 5,623,336 A | 4/1997 | Raab et al. |
| 5,635,830 A | 6/1997 | Itoh |
| 5,649,924 A | 7/1997 | Everett et al. |
| 5,697,373 A | 12/1997 | Richards-Kortum et al. |
| 5,698,397 A | 12/1997 | Zarling et al. |
| 5,710,630 A | 1/1998 | Essenpreis et al. |
| 5,716,324 A | 2/1998 | Toida |
| 5,719,399 A | 2/1998 | Alfano et al. |
| 5,730,731 A | 3/1998 | Mollenauer et al. |
| 5,735,276 A | 4/1998 | Lemelson |
| 5,740,808 A | 4/1998 | Panescu et al. |
| 5,748,318 A | 5/1998 | Maris et al. |
| 5,748,598 A | 5/1998 | Swanson et al. |
| 5,752,518 A | 5/1998 | McGee et al. |
| 5,784,352 A | 7/1998 | Swanson et al. |
| 5,785,651 A | 7/1998 | Baker et al. |
| 5,795,295 A | 8/1998 | Hellmuth et al. |
| 5,801,826 A | 9/1998 | Williams |
| 5,801,831 A | 9/1998 | Sargoytchev et al. |
| 5,803,082 A | 9/1998 | Stapleton et al. |
| 5,807,261 A | 9/1998 | Benaron et al. |
| 5,810,719 A | 9/1998 | Toida |
| 5,817,144 A | 10/1998 | Gregory |
| 5,836,877 A | 11/1998 | Zavislan et al. |
| 5,840,023 A | 11/1998 | Oraevsky et al. |
| 5,840,075 A | 11/1998 | Mueller et al. |
| 5,842,995 A | 12/1998 | Mahadevan-Jansen et al. |
| 5,843,000 A | 12/1998 | Nishioka et al. |
| 5,843,052 A | 12/1998 | Benja-Athon |
| 5,847,827 A | 12/1998 | Fercher |
| 5,862,273 A | 1/1999 | Pelletier |
| 5,865,754 A | 2/1999 | Sevick-Muraca et al. |
| 5,867,268 A | 2/1999 | Gelikonov et al. |
| 5,871,449 A | 2/1999 | Brown |
| 5,872,879 A | 2/1999 | Hamm |
| 5,877,856 A | 3/1999 | Fercher |
| 5,887,009 A | 3/1999 | Mandella et al. |
| 5,892,583 A | 4/1999 | Li |
| 5,910,839 A | 6/1999 | Erskine et al. |
| 5,912,764 A | 6/1999 | Togino |
| 5,920,373 A | 7/1999 | Bille |
| 5,920,390 A | 7/1999 | Farahi et al. |
| 5,921,926 A | 7/1999 | Rolland et al. |
| 5,926,592 A | 7/1999 | Harris et al. |

(56) References Cited

U.S. PATENT DOCUMENTS

| | | |
|---|---|---|
| 5,949,929 A | 9/1999 | Hamm |
| 5,951,482 A | 9/1999 | Winston et al. |
| 5,955,737 A | 9/1999 | Hallidy et al. |
| 5,956,355 A | 9/1999 | Swanson et al. |
| 5,968,064 A | 10/1999 | Selmon et al. |
| 5,975,697 A | 11/1999 | Podoleanu et al. |
| 5,983,125 A | 11/1999 | Alfano et al. |
| 5,987,346 A | 11/1999 | Benaron et al. |
| 5,991,697 A | 11/1999 | Nelson et al. |
| 5,994,690 A | 11/1999 | Kulkarni et al. |
| 5,995,223 A | 11/1999 | Power |
| 6,002,480 A | 12/1999 | Izatt et al. |
| 6,004,314 A | 12/1999 | Wei et al. |
| 6,006,128 A | 12/1999 | Izatt et al. |
| 6,007,996 A | 12/1999 | McNamara et al. |
| 6,010,449 A | 1/2000 | Selmon et al. |
| 6,014,214 A | 1/2000 | Li |
| 6,016,197 A | 1/2000 | Krivoshlykov |
| 6,020,963 A | 2/2000 | DiMarzio et al. |
| 6,025,956 A | 2/2000 | Nagano et al. |
| 6,033,721 A | 3/2000 | Nassuphis |
| 6,037,579 A | 3/2000 | Chan et al. |
| 6,044,288 A | 3/2000 | Wake et al. |
| 6,045,511 A | 4/2000 | Ott et al. |
| 6,048,742 A | 4/2000 | Weyburne et al. |
| 6,053,613 A | 4/2000 | Wei et al. |
| 6,069,698 A | 5/2000 | Ozawa et al. |
| 6,078,047 A | 6/2000 | Mittleman et al. |
| 6,091,496 A | 7/2000 | Hill |
| 6,091,984 A | 7/2000 | Perelman et al. |
| 6,094,274 A | 7/2000 | Yokoi |
| 6,107,048 A | 8/2000 | Goldenring et al. |
| 6,111,645 A | 8/2000 | Tearney et al. |
| 6,117,128 A | 9/2000 | Gregory |
| 6,120,516 A | 9/2000 | Selmon et al. |
| 6,134,003 A | 10/2000 | Tearney et al. |
| 6,134,010 A | 10/2000 | Zavislan |
| 6,134,033 A | 10/2000 | Bergano et al. |
| 6,141,577 A | 10/2000 | Rolland et al. |
| 6,151,522 A | 11/2000 | Alfano et al. |
| 6,159,445 A | 12/2000 | Klaveness et al. |
| 6,160,826 A | 12/2000 | Swanson et al. |
| 6,161,031 A | 12/2000 | Hochman et al. |
| 6,166,373 A | 12/2000 | Mao |
| 6,174,291 B1 | 1/2001 | McMahon et al. |
| 6,175,669 B1 | 1/2001 | Colston et al. |
| 6,185,271 B1 | 2/2001 | Kinsinger |
| 6,191,862 B1 | 2/2001 | Swanson et al. |
| 6,193,676 B1 | 2/2001 | Winston et al. |
| 6,198,956 B1 | 3/2001 | Dunne |
| 6,201,989 B1 | 3/2001 | Whitehead et al. |
| 6,208,415 B1 | 3/2001 | De Boer et al. |
| 6,208,887 B1 | 3/2001 | Clarke |
| 6,245,026 B1 | 6/2001 | Campbell et al. |
| 6,249,349 B1 | 6/2001 | Lauer |
| 6,249,381 B1 | 6/2001 | Suganuma |
| 6,249,630 B1 | 6/2001 | Stock et al. |
| 6,263,234 B1 | 7/2001 | Engelhardt et al. |
| 6,264,610 B1 | 7/2001 | Zhu |
| 6,272,376 B1 | 8/2001 | Marcu et al. |
| 6,274,871 B1 | 8/2001 | Dukor et al. |
| 6,282,011 B1 | 8/2001 | Tearney et al. |
| 6,297,018 B1 | 10/2001 | French et al. |
| 6,301,048 B1 | 10/2001 | Cao et al. |
| 6,308,092 B1 | 10/2001 | Hoyns |
| 6,324,419 B1 | 11/2001 | Guzelsu et al. |
| 6,341,036 B1 | 1/2002 | Tearney et al. |
| 6,353,693 B1 | 3/2002 | Kano et al. |
| 6,359,692 B1 | 3/2002 | Groot |
| 6,374,128 B1 | 4/2002 | Toida et al. |
| 6,377,349 B1 | 4/2002 | Fercher |
| 6,381,015 B1 * | 4/2002 | Sonehara et al. ............ 356/497 |
| 6,384,915 B1 | 5/2002 | Everett et al. |
| 6,393,312 B1 | 5/2002 | Hoyns |
| 6,394,964 B1 | 5/2002 | Sievert, Jr. et al. |
| 6,396,941 B1 | 5/2002 | Bacus et al. |
| 6,421,164 B2 | 7/2002 | Tearney et al. |
| 6,437,867 B2 | 8/2002 | Zeylikovich et al. |
| 6,441,892 B2 | 8/2002 | Xiao et al. |
| 6,441,959 B1 | 8/2002 | Yang et al. |
| 6,445,485 B1 | 9/2002 | Frigo et al. |
| 6,445,939 B1 | 9/2002 | Swanson et al. |
| 6,445,944 B1 | 9/2002 | Ostrovsky |
| 6,459,487 B1 | 10/2002 | Chen et al. |
| 6,463,313 B1 | 10/2002 | Winston et al. |
| 6,469,846 B2 | 10/2002 | Ebizuka et al. |
| 6,475,159 B1 | 11/2002 | Casscells et al. |
| 6,475,210 B1 | 11/2002 | Phelps et al. |
| 6,477,403 B1 | 11/2002 | Eguchi et al. |
| 6,485,413 B1 | 11/2002 | Boppart et al. |
| 6,485,482 B1 | 11/2002 | Belef |
| 6,501,551 B1 | 12/2002 | Tearney et al. |
| 6,501,878 B2 | 12/2002 | Hughes et al. |
| 6,516,014 B1 | 2/2003 | Sellin et al. |
| 6,517,532 B1 | 2/2003 | Altshuler et al. |
| 6,538,817 B1 | 3/2003 | Farmer et al. |
| 6,540,391 B2 | 4/2003 | Lanzetta et al. |
| 6,549,801 B1 | 4/2003 | Chen et al. |
| 6,552,796 B2 | 4/2003 | Magnin et al. |
| 6,556,305 B1 | 4/2003 | Aziz et al. |
| 6,556,853 B1 | 4/2003 | Cabib et al. |
| 6,558,324 B1 | 5/2003 | Von Behren et al. |
| 6,560,259 B1 | 5/2003 | Hwang et al. |
| 6,564,087 B1 | 5/2003 | Pitris et al. |
| 6,564,089 B2 | 5/2003 | Izatt et al. |
| 6,567,585 B2 | 5/2003 | Harris et al. |
| 6,593,101 B2 | 7/2003 | Richards-Kortum et al. |
| 6,611,833 B1 | 8/2003 | Johnson et al. |
| 6,615,071 B1 | 9/2003 | Casscells, III et al. |
| 6,622,732 B2 | 9/2003 | Constantz |
| 6,654,127 B2 | 11/2003 | Everett et al. |
| 6,657,730 B2 | 12/2003 | Pfau et al. |
| 6,658,278 B2 | 12/2003 | Gruhl |
| 6,680,780 B1 | 1/2004 | Fee |
| 6,685,885 B2 | 2/2004 | Nolte et al. |
| 6,687,007 B1 | 2/2004 | Meigs |
| 6,687,010 B1 | 2/2004 | Horii et al. |
| 6,687,036 B2 | 2/2004 | Riza |
| 6,692,430 B2 | 2/2004 | Adler |
| 6,701,181 B2 | 3/2004 | Tang et al. |
| 6,721,094 B1 | 4/2004 | Sinclair et al. |
| 6,738,144 B1 | 5/2004 | Dogariu et al. |
| 6,741,355 B2 | 5/2004 | Drabarek |
| 6,757,467 B1 | 6/2004 | Rogers |
| 6,790,175 B1 | 9/2004 | Furusawa et al. |
| 6,806,963 B1 | 10/2004 | Wälti et al. |
| 6,816,743 B2 | 11/2004 | Moreno et al. |
| 6,831,781 B2 | 12/2004 | Tearney et al. |
| 6,839,496 B1 | 1/2005 | Mills et al. |
| 6,882,432 B2 | 4/2005 | Deck |
| 6,900,899 B2 | 5/2005 | Nevis |
| 6,903,820 B2 | 6/2005 | Wang |
| 6,909,105 B1 | 6/2005 | Heintzmann et al. |
| 6,949,072 B2 | 9/2005 | Furnish et al. |
| 6,961,123 B1 | 11/2005 | Wang et al. |
| 6,980,299 B1 | 12/2005 | de Boer |
| 6,996,549 B2 | 2/2006 | Zhang et al. |
| 7,006,231 B2 | 2/2006 | Ostrovsky et al. |
| 7,006,232 B2 | 2/2006 | Rollins et al. |
| 7,019,838 B2 | 3/2006 | Izatt et al. |
| 7,027,633 B2 | 4/2006 | Foran et al. |
| 7,061,622 B2 | 6/2006 | Rollins et al. |
| 7,072,047 B2 | 7/2006 | Westphal et al. |
| 7,075,658 B2 | 7/2006 | Izatt et al. |
| 7,099,358 B1 | 8/2006 | Chong |
| 7,113,288 B2 | 9/2006 | Fercher |
| 7,113,625 B2 | 9/2006 | Watson et al. |
| 7,130,320 B2 | 10/2006 | Tobiason et al. |
| 7,139,598 B2 | 11/2006 | Hull et al. |
| 7,142,835 B2 | 11/2006 | Paulus |
| 7,148,970 B2 | 12/2006 | De Boer |
| 7,177,027 B2 | 2/2007 | Hirasawa et al. |
| 7,190,464 B2 | 3/2007 | Alphonse |
| 7,230,708 B2 | 6/2007 | Lapotko et al. |

(56) References Cited

U.S. PATENT DOCUMENTS

| | | | |
|---|---|---|---|
| 7,231,243 B2 | 6/2007 | Tearney et al. |
| 7,236,637 B2 | 6/2007 | Sirohey et al. |
| 7,242,480 B2 | 7/2007 | Alphonse |
| 7,267,494 B2 | 9/2007 | Deng et al. |
| 7,272,252 B2 | 9/2007 | De La Torre-Bueno et al. |
| 7,304,798 B2 | 12/2007 | Izumi et al. |
| 7,310,150 B2 | 12/2007 | Guillermo et al. |
| 7,330,270 B2 | 2/2008 | O'Hara et al. |
| 7,336,366 B2 | 2/2008 | Choma et al. |
| 7,342,659 B2 | 3/2008 | Horn et al. |
| 7,355,716 B2 | 4/2008 | De Boer et al. |
| 7,355,721 B2 | 4/2008 | Quadling et al. |
| 7,359,062 B2 | 4/2008 | Chen et al. |
| 7,366,376 B2 | 4/2008 | Shishkov et al. |
| 7,382,809 B2 | 6/2008 | Chong et al. |
| 7,391,520 B2 | 6/2008 | Zhou et al. |
| 7,458,683 B2 | 12/2008 | Chernyak et al. |
| 7,530,948 B2 | 5/2009 | Seibel et al. |
| 7,539,530 B2 | 5/2009 | Caplan et al. |
| 7,609,391 B2 | 10/2009 | Betzig |
| 7,630,083 B2 | 12/2009 | de Boer et al. |
| 7,643,152 B2 | 1/2010 | de Boer et al. |
| 7,643,153 B2 | 1/2010 | de Boer et al. |
| 7,646,905 B2 | 1/2010 | Guittet et al. |
| 7,649,160 B2 | 1/2010 | Colomb et al. |
| 7,664,300 B2 | 2/2010 | Lange et al. |
| 7,733,497 B2 | 6/2010 | Yun et al. |
| 7,782,464 B2 | 8/2010 | Mujat et al. |
| 7,805,034 B2 | 9/2010 | Kato et al. |
| 7,969,578 B2 | 6/2011 | Yun et al. |
| 2001/0036002 A1 | 11/2001 | Tearney et al. |
| 2001/0047137 A1 | 11/2001 | Moreno et al. |
| 2002/0016533 A1 | 2/2002 | Marchitto et al. |
| 2002/0024015 A1 | 2/2002 | Hoffmann et al. |
| 2002/0048025 A1 | 4/2002 | Takaoka |
| 2002/0048026 A1 | 4/2002 | Isshiki et al. |
| 2002/0052547 A1 | 5/2002 | Toida |
| 2002/0057431 A1 | 5/2002 | Fateley et al. |
| 2002/0064341 A1 | 5/2002 | Fauver et al. |
| 2002/0076152 A1 | 6/2002 | Hughes et al. |
| 2002/0085209 A1 | 7/2002 | Mittleman et al. |
| 2002/0086347 A1 | 7/2002 | Johnson et al. |
| 2002/0091322 A1 | 7/2002 | Chaiken et al. |
| 2002/0093662 A1 | 7/2002 | Chen et al. |
| 2002/0109851 A1 | 8/2002 | Deck |
| 2002/0113965 A1 | 8/2002 | Roche et al. |
| 2002/0122182 A1 | 9/2002 | Everett et al. |
| 2002/0122246 A1 | 9/2002 | Tearney et al. |
| 2002/0140942 A1 | 10/2002 | Fee et al. |
| 2002/0158211 A1 | 10/2002 | Gillispie |
| 2002/0161357 A1 | 10/2002 | Anderson et al. |
| 2002/0163622 A1 | 11/2002 | Magnin et al. |
| 2002/0168158 A1 | 11/2002 | Furusawa et al. |
| 2002/0172485 A1 | 11/2002 | Keaton et al. |
| 2002/0183623 A1 | 12/2002 | Tang et al. |
| 2002/0188204 A1 | 12/2002 | McNamara et al. |
| 2002/0196446 A1 | 12/2002 | Roth et al. |
| 2002/0198457 A1 | 12/2002 | Tearney et al. |
| 2003/0001071 A1 | 1/2003 | Mandella et al. |
| 2003/0013973 A1 | 1/2003 | Georgakoudi et al. |
| 2003/0023153 A1 | 1/2003 | Izatt et al. |
| 2003/0026735 A1 | 2/2003 | Nolte et al. |
| 2003/0028114 A1 | 2/2003 | Casscells, III et al. |
| 2003/0030816 A1 | 2/2003 | Eom et al. |
| 2003/0043381 A1 | 3/2003 | Fercher |
| 2003/0053673 A1 | 3/2003 | Dewaele et al. |
| 2003/0067607 A1 | 4/2003 | Wolleschensky et al. |
| 2003/0082105 A1 | 5/2003 | Fischman et al. |
| 2003/0097048 A1 | 5/2003 | Ryan et al. |
| 2003/0108911 A1 | 6/2003 | Klimant et al. |
| 2003/0120137 A1 | 6/2003 | Pawluczyk et al. |
| 2003/0135101 A1 | 7/2003 | Webler |
| 2003/0137669 A1 | 7/2003 | Rollins et al. |
| 2003/0164952 A1 | 9/2003 | Deichmann et al. |
| 2003/0165263 A1 | 9/2003 | Hamer et al. |
| 2003/0171691 A1 | 9/2003 | Casscells, III et al. |
| 2003/0174339 A1 | 9/2003 | Feldchtein et al. |
| 2003/0199769 A1 | 10/2003 | Podoleanu et al. |
| 2003/0216719 A1 | 11/2003 | Debenedictis et al. |
| 2003/0218756 A1 | 11/2003 | Chen et al. |
| 2003/0220749 A1 | 11/2003 | Chen et al. |
| 2003/0236443 A1 | 12/2003 | Cespedes et al. |
| 2004/0002650 A1 | 1/2004 | Mandrusov et al. |
| 2004/0039298 A1 | 2/2004 | Abreu |
| 2004/0054268 A1 | 3/2004 | Esenaliev et al. |
| 2004/0072200 A1 | 4/2004 | Rigler et al. |
| 2004/0075841 A1 | 4/2004 | Van Neste et al. |
| 2004/0076940 A1 | 4/2004 | Alexander et al. |
| 2004/0077949 A1 | 4/2004 | Blofgett et al. |
| 2004/0085540 A1 | 5/2004 | Lapotko et al. |
| 2004/0086245 A1 | 5/2004 | Farroni et al. |
| 2004/0095464 A1 | 5/2004 | Miyagi et al. |
| 2004/0100631 A1 | 5/2004 | Bashkansky et al. |
| 2004/0100681 A1 | 5/2004 | Bjarklev et al. |
| 2004/0110206 A1 | 6/2004 | Wong et al. |
| 2004/0126048 A1 | 7/2004 | Dave et al. |
| 2004/0126120 A1 | 7/2004 | Cohen et al. |
| 2004/0133191 A1 | 7/2004 | Momiuchi et al. |
| 2004/0150829 A1 | 8/2004 | Koch et al. |
| 2004/0150830 A1 | 8/2004 | Chan |
| 2004/0152989 A1 | 8/2004 | Puttappa et al. |
| 2004/0165184 A1 | 8/2004 | Mizuno |
| 2004/0166593 A1 | 8/2004 | Nolte et al. |
| 2004/0189999 A1 | 9/2004 | De Groot et al. |
| 2004/0212808 A1 | 10/2004 | Okawa et al. |
| 2004/0239938 A1 | 12/2004 | Izatt et al. |
| 2004/0246490 A1 * | 12/2004 | Wang ............................ 356/479 |
| 2004/0246583 A1 | 12/2004 | Mueller et al. |
| 2004/0254474 A1 | 12/2004 | Seibel et al. |
| 2004/0258106 A1 | 12/2004 | Araujo et al. |
| 2004/0263843 A1 | 12/2004 | Knopp et al. |
| 2005/0004453 A1 | 1/2005 | Tearney et al. |
| 2005/0018133 A1 | 1/2005 | Huang et al. |
| 2005/0018200 A1 | 1/2005 | Guillermo et al. |
| 2005/0018201 A1 | 1/2005 | De Boer et al. |
| 2005/0035295 A1 | 2/2005 | Bouma et al. |
| 2005/0036150 A1 | 2/2005 | Izatt et al. |
| 2005/0046837 A1 | 3/2005 | Izumi et al. |
| 2005/0057680 A1 | 3/2005 | Agan |
| 2005/0057756 A1 | 3/2005 | Fang-Yen et al. |
| 2005/0059894 A1 | 3/2005 | Zeng et al. |
| 2005/0065421 A1 | 3/2005 | Burckhardt et al. |
| 2005/0075547 A1 | 4/2005 | Wang |
| 2005/0083534 A1 | 4/2005 | Riza et al. |
| 2005/0119567 A1 | 6/2005 | Choi et al. |
| 2005/0128488 A1 | 6/2005 | Yelin et al. |
| 2005/0165303 A1 | 7/2005 | Kleen et al. |
| 2005/0171438 A1 | 8/2005 | Chen et al. |
| 2005/0190372 A1 | 9/2005 | Dogariu et al. |
| 2005/0254061 A1 | 11/2005 | Alphonse et al. |
| 2006/0020172 A1 | 1/2006 | Luerssen et al. |
| 2006/0033923 A1 | 2/2006 | Hirasawa et al. |
| 2006/0093276 A1 | 5/2006 | Bouma et al. |
| 2006/0103850 A1 | 5/2006 | Alphonse et al. |
| 2006/0146339 A1 | 7/2006 | Fujita et al. |
| 2006/0155193 A1 | 7/2006 | Leonardi et al. |
| 2006/0164639 A1 | 7/2006 | Horn et al. |
| 2006/0171503 A1 | 8/2006 | O'Hara et al. |
| 2006/0184048 A1 | 8/2006 | Saadat et al. |
| 2006/0193352 A1 | 8/2006 | Chong et al. |
| 2006/0244973 A1 | 11/2006 | Yun et al. |
| 2006/0279742 A1 | 12/2006 | Tearney |
| 2007/0019208 A1 | 1/2007 | Toida et al. |
| 2007/0038040 A1 | 2/2007 | Cense et al. |
| 2007/0070496 A1 | 3/2007 | Gweon et al. |
| 2007/0076217 A1 | 4/2007 | Baker et al. |
| 2007/0086013 A1 | 4/2007 | De Lega et al. |
| 2007/0086017 A1 | 4/2007 | Buckland et al. |
| 2007/0091317 A1 | 4/2007 | Freischlad et al. |
| 2007/0133002 A1 | 6/2007 | Wax et al. |
| 2007/0188855 A1 | 8/2007 | Shishkov et al. |
| 2007/0208225 A1 | 9/2007 | Czaniera et al. |
| 2007/0223006 A1 | 9/2007 | Tearney et al. |
| 2007/0233056 A1 | 10/2007 | Yun |

(56) References Cited

U.S. PATENT DOCUMENTS

| | | |
|---|---|---|
| 2007/0233396 A1 | 10/2007 | Tearney et al. |
| 2007/0236700 A1 | 10/2007 | Yun et al. |
| 2007/0258094 A1 | 11/2007 | Izatt et al. |
| 2007/0291277 A1 | 12/2007 | Everett et al. |
| 2008/0002197 A1 | 1/2008 | Sun et al. |
| 2008/0007734 A1 | 1/2008 | Park et al. |
| 2008/0049220 A1 | 2/2008 | Izzia et al. |
| 2008/0094613 A1 | 4/2008 | de Boer et al. |
| 2008/0094637 A1 | 4/2008 | de Boer et al. |
| 2008/0097225 A1 | 4/2008 | Tearney et al. |
| 2008/0097709 A1 | 4/2008 | de Boer et al. |
| 2008/0100837 A1 | 5/2008 | de Boer et al. |
| 2008/0152353 A1 | 6/2008 | de Boer et al. |
| 2008/0154090 A1 | 6/2008 | Hashimshony |
| 2008/0192236 A1 | 8/2008 | Smith et al. |
| 2008/0204762 A1 | 8/2008 | Izatt et al. |
| 2008/0228086 A1 | 9/2008 | Ilegbusi |
| 2008/0265130 A1 | 10/2008 | Colomb et al. |
| 2008/0308730 A1 | 12/2008 | Vizi et al. |
| 2009/0005691 A1 | 1/2009 | Huang |
| 2009/0011948 A1 | 1/2009 | Uniu et al. |
| 2009/0192358 A1 | 7/2009 | Jaffer et al. |
| 2009/0196477 A1 | 8/2009 | Cense et al. |
| 2009/0273777 A1 | 11/2009 | Yun et al. |
| 2009/0281390 A1 | 11/2009 | Qiu et al. |
| 2009/0290156 A1 | 11/2009 | Popescu et al. |
| 2010/0002241 A1 | 1/2010 | Hirose |
| 2010/0086251 A1 | 4/2010 | Xu et al. |
| 2010/0094576 A1 | 4/2010 | De Boer et al. |
| 2010/0150467 A1 | 6/2010 | Zhao et al. |
| 2010/0309477 A1 | 12/2010 | Yun et al. |

FOREIGN PATENT DOCUMENTS

| | | |
|---|---|---|
| DE | 4309056 | 9/1994 |
| DE | 19542955 | 5/1997 |
| DE | 10351319 | 6/2005 |
| EP | 0110201 | 6/1984 |
| EP | 0251062 | 1/1988 |
| EP | 0617286 | 2/1994 |
| EP | 0590268 | 4/1994 |
| EP | 0728440 | 8/1996 |
| EP | 0933096 | 8/1999 |
| EP | 1324051 | 7/2003 |
| EP | 1426799 | 6/2009 |
| FR | 2738343 | 8/1995 |
| GB | 1257778 | 12/1971 |
| GB | 2030313 | 4/1980 |
| GB | 2209221 | 5/1989 |
| GB | 2298057 | 8/1996 |
| JP | 6073405 | 4/1985 |
| JP | 20040056907 | 2/1992 |
| JP | 4135550 | 5/1992 |
| JP | 4135551 | 5/1992 |
| JP | 5509417 | 11/1993 |
| JP | 02214127 | 7/2002 |
| JP | 20030035659 | 2/2003 |
| JP | 2007271761 | 10/2007 |
| WO | 7900841 | 10/1979 |
| WO | 9201966 | 2/1992 |
| WO | 9303672 | 3/1992 |
| WO | 9216864 | 10/1992 |
| WO | 9216865 | 10/1992 |
| WO | 9219930 | 11/1992 |
| WO | 9533971 | 12/1995 |
| WO | 9628212 | 9/1996 |
| WO | 9732182 | 9/1997 |
| WO | 9800057 | 1/1998 |
| WO | 9801074 | 1/1998 |
| WO | 9814132 | 4/1998 |
| WO | 9835203 | 8/1998 |
| WO | 9838907 | 9/1998 |
| WO | 9846123 | 10/1998 |
| WO | 9848838 | 11/1998 |
| WO | 9848846 | 11/1998 |
| WO | 9905487 | 2/1999 |
| WO | 9944089 | 2/1999 |
| WO | 9944089 | 9/1999 |
| WO | 9957507 | 11/1999 |
| WO | 0058766 | 10/2000 |
| WO | 0101111 | 1/2001 |
| WO | 0108579 | 2/2001 |
| WO | 0127679 | 4/2001 |
| WO | 0138820 | 5/2001 |
| WO | 0142735 | 6/2001 |
| WO | 0236015 | 5/2002 |
| WO | 0237075 | 5/2002 |
| WO | 0238040 | 5/2002 |
| WO | 0254027 | 7/2002 |
| WO | 02053050 | 7/2002 |
| WO | 02084263 | 10/2002 |
| WO | 03013624 | 2/2003 |
| WO | 03020119 | 3/2003 |
| WO | 03046495 | 6/2003 |
| WO | 03046636 | 6/2003 |
| WO | 03052478 | 6/2003 |
| WO | 03053226 | 7/2003 |
| WO | 03062802 | 7/2003 |
| WO | 03105678 | 12/2003 |
| WO | 2004034869 | 4/2004 |
| WO | 2004057266 | 7/2004 |
| WO | 20040666824 | 8/2004 |
| WO | 2004088361 | 10/2004 |
| WO | 2004105598 | 12/2004 |
| WO | 2005000115 | 1/2005 |
| WO | 2005047813 | 5/2005 |
| WO | 2005054780 | 6/2005 |
| WO | 2005082225 | 9/2005 |
| WO | 20050822225 | 9/2005 |
| WO | 2006004743 | 1/2006 |
| WO | 2006014392 | 2/2006 |
| WO | 2006039091 | 4/2006 |
| WO | 20060388876 | 4/2006 |
| WO | 2006059109 | 6/2006 |
| WO | 2006124860 | 11/2006 |
| WO | 2006130797 | 12/2006 |
| WO | 2007028531 | 3/2007 |
| WO | 2007038787 | 4/2007 |
| WO | 2007083138 | 7/2007 |
| WO | 2007084995 | 7/2007 |
| WO | 2009153929 | 12/2009 |

OTHER PUBLICATIONS

Beddow et al., (May 2002) "Improved Performance Interferomater Designs for Optical Coherence Tomograohy", IEEE Optical Fiber Sensors Conference, pp. 527-530.

Yaqoob et al., (Jun. 2002) "High-Speed Wavelength-Multiplexed Fiber-Optic Sensors for Biomedicine," Sensors Proceedings of the IEEE, pp. 325-330.

Office Action dated Feb. 18, 2009 for U.S. Appl. No. 11/697,012.

Zhang et al, (Sep. 2004) "Fourier Domain Functional Optical Coherence Tomography", Saratov Fall Meeting 2004, pp. 8-14.

Office Action dated Feb. 23, 2009 for U.S. Appl. No. 11/956,129.

Office Action bated Mar. 16, 2009 for U.S. Appl. No. 11/621,694.

Office Action dated Oct. 1, 2009 for U.S. Appl. No. 11/677,278.

Office dated Oct. 6, 2009 for U.S. Appl. No. 12/015,642.

Lin, Stollen et al., (1977) "A CW Tunable Near-infrared (1.085-1.175-um) Raman Oscillator," Optics Letters, vol. 1, 96.

Summons to attend Oral Proceedings dated Oct. 9, 2009 for European patent application No. 06813365.1

Office Action dated Dec. 15, 2009 for U.S. Appl. No. 11/549,397.

R. Haggitt et al., "Barrett's Esophagus Correlation Between Mucin Histochemistry, Flow Cytometry, and Histological Diagnosis for Predicting Increased Cancer Risk," Apr. 1988, American Journal of Pathology, vol. 131, No. 1, pp. 53-61.

R.H. Hardwick et al., (1995) "c-erbB-2 Overexpression in the Dysplasia/Carcinoma Sequence of Barrett's Oesophagus," Journal of Clinical Pathology, vol. 48, No. 2, pp. 129-132.

(56) References Cited

OTHER PUBLICATIONS

W. Polkowski et al, (1998) "Clinical Decision making in Barrett's Oesophagus can be supported by Computerized Immunoquantitation and Morphometry of Feature Associated with Proliferation and Differeatiation," Journal of pathology, vol. 184, pp. 161-168.
J.R. Turner et al., MN Antigen Expression in Normal Preneoplastic, and Neoplastic Esophagus: A Clinicopathological Study of a New Cancer-Associate Biomarker,: Jun. 1997, Human Pathology, vol. 28, No. 6, pp. 740-744.
D.J. Bowery et al., (1999) "Patterns of Gastritis in Patients with Gastro-Oesophageal Reflux Disease,", Gut, vol. 45, pp. 798-803.
O'Reich et al., (2000) "Expression of Oestrogen and Progesterone Receptors in Low-Grade Endometrial Stromal Sarcomas," British Journal of Cancer, vol. 82, No. 5, pp. 1030-1034.
M.I. Canto et al., (1999) "Vital Staining and Barrett's Esophagus," Gastrointestinal Endoscopy, vol. 49, No. 3, Part 2, pp. S12-S16.
S. Jackle et al., (2000) "In Vivo Endoscopic Optical coherence Tomography of the Human Gastrointestinal Tract-Toward Optical Biopsy," Encoscopy, vol. 32, No. 10, pp. 743-749.
E. Montgomery et al., "Reproducibility of the Diagnosis of Dysplasiain Barrett Esophagus: A Reaffirmation," Apr. 2001, Human Pathology, vol. 32, No. 4, pp. 368-378.
H. Geddert et al., "Expression of Cyclin B1 in the Metaplasia-Dysphasia -Carcinoma Sequence of Barrett Esophagus," Jan. 2002, Cancer, vol. 94, No. 1, pp. 212-218.
P. Pfau et al., (2003) "Criteria for the Diagnosis of Dysphasia by Endoscopic Optical Coherence Tomography," Gastrointestinal Endoscopy, vol. 58, No. 2, pp. 196-2002.
R. Kiesslich et al., (2004) "Confocal LAser Endoscopy for Diagnosing Intraepithelial Neoplasias and Colorectal Cancer in Vivo," Gastroenterology, vol. 127, No. 3, pp. 706-713.
X. Qi et al., (2004) "Computer Aided Diagnosis of Dysphasia in Barrett's Esophagus Using Endoscopic Optical Coherence Tomography," SPIE, Coherence Domain Optical Methods and Optical Coherence Tomography in Biomedicine VIII. Proc. of Conference on., vol. 5316, pp. 33-40.
Seltzer et al., (1991) "160 nm Continuous Tuning of a MQW Laser in an External Cavity Across the Entire 1.3 μm Communications Window," Electronics Letters, vol. 27, pp. 95-96.
Office Action dated Jan. 25, 2010 for U.S. Appl. No. 11/537,048.
International Search Report dated Jan. 27, 2010 for PCT/US2009/050553.
International Search Report dated Jan. 27, 2010 for PCT/US2009/047988.
International Search Report dated Feb. 23, 2010 for U.S. Appl. No. 11/445,131.
Office Action dated Mar. 18, 2010 of U.S. Appl. No. 11/844,454.
Office Action dated Apr. 8, 2010 of U.S. Appl. No. 11/414,564.
Japanese Office Action dated Apr. 13, 2010 for Japanese Patent application No. 2007-515029.
International Search Report dated May 27, 2010 for PCT/US2009/063420.
Office Action dated May 28, 2010 for U.S. Appl. No. 12/015,642.
Office Action dated Jun. 2, 2010 for U.S. Appl. No. 12/112,205.
Office Action dated Jul. 7, 2010 for U.S. Appl. No. 11/624,277.
Montag Ethan D., "Parts of the Eye" online textbook for JIMG 774: Vision & Osycophysics, download on Jun. 23, 2010 from http://www.cis.rit.edu/people/faculty/montag/vandplite/pages/chap_8/ch8p3.html.
Office Action dated Jul. 16, 2010 for U.S. Appl. No. 11/445,990.
Office Action dated Jul. 20, 2010 for U.S. Appl. No. 11/625,135.
Office Action dated Aug. 5, 2010 for U.S. Appl. No. 11/623,852.
Chinese office action dated Aug. 4, 2010 for CN 200780005949.9.
Chinese office aciton dated Aug. 4, 2010 for CN 200780016266.3.
Zhang et al., "Full Range Polarization-Sensitive Fourier Domain Optical Coherence Tomography" Optics Express, Nov. 29, 2004, vol. 12, No. 24.
Office Action dated Aug. 27, 2010 for U.S. Appl. No. 11/569,790.
Office Action dated Aug. 31, 2010 for U.S. Appl. No. 11/677,278.
Office Action dated Sep. 3, 2010 for U.S. Appl. No. 12/139,314.
Yong Zhao et al: "Virtual Data Grid Middleware Services for Data-Intensive Science", Concurrency and Computation: Practice and Experience, Wiley, London, GB, Jan. 1, 2000, pp. 1-7, pp. 1532-0626.
Swan et al., "Toward Nanometer-Scale Resolution in Fluorescence Microscopy using Spectral Self-Iterference" IEEE Journal. Selected Topics in Quantum Electronics 9(2) 2003, pp. 294-300.
Moiseev et al., "Spectral Self-Interfence Fluorescence Microscopy", J. Appl. Phys. 96 (9) 2004, pp. 5311-5315.
Hendrik Verschueren, "Interference Reflection Microscopy in Cell Biology", J. cell Sci. 75, 1985, pp. 289-301.
Park et al., "Diffraction Phase and Fluorescence Microscopy", Opt. Expr. 14 (18) 2006, pp. 8263-8268.
Swan et al., "High Resolution Spectral Self-Interference Fluorescence Microscopy", Proc. SPIE 4621, 2002, pp. 77-85.
Sanchez et al., "Near-Field Fluorscence Microscopy Based on Two-Photon Excvitation with Metal Tips", Phys. Rev. Lett. 82 (20) 1999, pp. 4014-4017.
Wojtkowski, Maciej, Ph.D. "Three-Dimensional Retinal Imaging with High-Speed Ultrahigh-Resolution Optical Coherence Tomography" Ophthalmology, Oct. 2005, 112(10): 1734-1746.
Vaughan, J.M. et al., "Brillouin Scattering, Density and Elastic Properties of the Lens and Cornea of the Eye", Nature, vol. 284, Apr. 3, 1980, pp. 489-491.
Hess, S.T. et al., "Ultra-high Resolution Imaging by Fluorescence Photoactivation Localization Microscopy" Biophysical Journal vol. 91, Dec. 2006, 4258-4272.
Fernandez-Suarez, M. et al., "Fluorescent Probes for Super-Resolution Imaging in Living Cells" Nature reviews Molecular Cell Biology vol. 9, Dec. 2008.
Extended European Search Report mailed Dec. 14, 2010 for EP 10182301.1.
S. Hell et al. "Breaking the diffraction resolution limit bu stimulated-emission—stimulated-emission-depletion fluorescence microscopy," Optics Letters. 19:495 (1995) and Ground State Depletion (GSD).
S. Hell et al. "Ground-State-Depletion fluorescence microscopy—a concept for breaking the diffraction resolution limit", Applied Physics B. 60:780 (1994) fluorescence microscopy, photo-activated localization microscopy (PALM).
E. Betzig et al. "Imaging intracellular fluorescent proteins at nanometer resolution," Science 313:1642 (2006), stochastic optical reconstruction microscopy (STORM).
M. Rust et al. "Sub-diffraction-limited imaging by stochastic optical reconstruction microscopy (STORM)," Nature Methods 3:783 (2006), and structured illumination micrscopy (SIM).
Bailey et al. "Enhancement of Axial Resolution in Fluorescence Microscopy by Stading-Wave Excitation," Nature 366:44 (1993).
M. Gustafsson "Surpassing the lateral resolution limit by a factor of two using structured illumination microscopy," Journal of Microscopy 198:82 (2000).
M. Gustafsson "Nonlinear structured illumination microscopy: Wide-field fluorescence imaging with theoretically unlimited resolution," PNAS 102:13081 (2005)).
R. Thompson et al. "Precise nanometer localization analysis for individual fluorescent probes," Biophysical Journal 82:2775 (2002).
K. Drabe et al. "Localization of Spontaneous Emission in front of a mirror," Optics Communications 73:91 (1989).
Swan et al. "Toward nanometer-scale resolution in fluorescence microscopy using spectral self-interference," IEEE Quantum Electronics 9:294 (2003).
Joo, et al. "Spectral Domain optical coherence phase and multiphoton microscopy," Optics Letters 32:623 (2007).
Virmani et al., "Lesions from sudden coronary death: A comprehensive morphological classification scheme for atherosclerotic lesions," Arterioscler. Thromb. Vase. Bio., 20:1262-75 (2000).
Gonzalez, R.C. and Wintz, P., "Digital Image Processing" Addison-Wesley Publishing Company, Reading MA, 1987.
V. Tuchin et al., "Speckle interferometry in the measurements ofbiotissues vibrations," SPIE, 1647: 125 (1992).
A.A. Bednov et al., "Investigation of Statistical Properties of Lymph Flow Dynamics Using Speckle-Microscopy," SPIE, 2981: 181-90 (1997).

(56) References Cited

OTHER PUBLICATIONS

Feng et al., "Mesocopic Conductors and Correlations in Laser Speckle Patters" Science, New Series, vol. 251, No. 4994, pp. 633-639 (Feb. 8, 1991).
Lee et al., "The Unstable Atheroma," Arteriosclerosis, Thrombosis & Vascular Biology, 17:1859-67 (1997).
International Search report dated Apr. 29, 2011 for PCT/US2010/051715.
International Search report dated Sep. 13, 2010 for PCT/US2010/023215.
International Search Report dated Jul. 28, 2011 for PCT/US2010/059534.
Internatinal Search report dated Nov. 18, 2011 for PCT/US2011/027450.
International Search report dated Nov. 18, 2011 for PCT/US2011/027437.
International Search report dated Nov. 22, 2011 for PCT/US2011/027421.
Liptak David C. et al., (2007) "On the Development of a Confocal Rayleigh-Brillouin Microscope" *American Institute of Physics* vol. 78, 016106.
Office Action mailed Oct. 1, 2008 for U.S. Appl. No. 11/955,986.
Invitation of Pay Additional Fees mailed Aug. 7, 2008 for International Application No. PCT/US2008/062354.
Invitation of Pay Additional Fees mailed Jul. 20, 2008 for International Application No. PCT/US2007/081982.
International Search Report and Written Opinion mailed Mar. 7, 2006 for PCT/US2005/035711.
International Search Report and Written Opinion mailed Jul. 18, 2008 for PCT/US2008/057533.
Aizu, Y et al. (1991) "Bio-Speckle Phenomena and Their Application to the Evaluation of Blood Flow" Optics and Laser Technology, vol. 23, No. 4, Aug. 1, 1991.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Gonick, Maria M., et al (2002) "Visualization of Blood Microcirculation Parameters in Human Tissues by Time Integrated Dynamic Speckles Analysis" vol. 972, No. 1, Oct. 1, 2002.
International Search Report and Written Opinion mailed Jul. 4, 2008 for PCT/US2008/051432.
Jonathan, Enock (2005) "Dual Reference Arm Low-Coherence Interferometer-Based Reflectometer for Optical Coherence Tomography (OCT) Application" *Optics Communications* vol. 252.
Motaghian Nezam, S.M.R, (2007) "increased Ranging Depth in optical Frequency Domain Imaging by Frequency Encoding" *Optics Letters*, vol. 32, No. 19, Oct. 1, 2007.
Office Action dated Jun. 30, 2008 for U.S. Appl. No. 11/670,058.
Office Action dated Jul. 7, 2008 for U.S. Appl. No. 10/551,735.
Australian Examiner's Report mailed May 27, 2008 for Australian patent application No. 2003210669.
Notice of Allowance mailed Jun. 4, 2008 for U.S. Appl. No. 11/174,425.
European communication dated May 15, 2008 for European patent application No. 05819917.5.
International Search Report and Written Opinion mailed Jun. 10, 2008 for PCT/US2008/051335.
Oh. W.Y. et al (2006) "Ultrahigh-Speed Optical Frequency Domain Imaging and Application to laser Ablation Monitoring" *Applied Physics Letters*, vol. 88.
Office Action dated Aug. 21, 2008 for U.S. Appl. No. 11/505,700.
Sticker, Markus (2002) En Face Imaging of Single Cell layers by Differential Phase-Contrast Optical Coherence Microscopy) *Optics Letters*, col. 27, No. 13, Jul. 1, 2002.
International Search Report and Written Opinion dated Jul. 17, 2008 for International Application No. PCT/US2008/057450.
International Search Report and Written Opinion dated Aug. 11, 2008 for International Application No. PCT/US2008/058703.

US National Library of Medicine (NLM), Bethesda, MD, US; Oct. 2007, "Abstracts of the 19th Annual Symposium of Transcatheter Cardiovascular Therapeutics, Oct. 20-25, 2007, Washington, DC, USA."
International Search Report and Written Opinion dated May 26, 2008 for International Application No. PCT/US2008/051404.
Office Action dated Aug. 25, 2008 for U.S. Appl. No. 11/264,655.
Office Action dated Sep. 11, 2008 for U.S. Appl. No. 11/624,334.
Office Action dated Aug. 21, 2008 for U.S. Appl. No. 11/956,079.
Gelikono, V. M. et al. Oct. 1, 2004 "Two-Wavelength Optical CoherenceTomography" Radio physics and Quantum Electronics, Kluwer Academic Publishers-Consultants. vol. 47, No. 10-1.
International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy".
Database Biosis Biosciences Informati-on Service, Philadelphia, PA, US; Oct. 2006, Yelin D. et al: "Three-Dimensional Miniature Endoscopy".
International Search Report and Written Opinion mailed Mar. 14, 2005 for PCT/US2004/018045.
Notification of the international Preliminary Report on Patentability mailed Oct. 21, 2005.
Shim M.G. et al., "Study of Fiber-Optic Probes for in vivo Medical Raman Spectroscopy" Applied Spectroscopy. vol. 53, No. 6, Jun. 1999.
Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.
Jun Zhang et al. "Full Range Polarization-Sensitive Fourier Domain Optical Coherence Tomography" Optics Express, vol. 12, No. 24. Nov. 29, 2004.
Yonghua et al., "Real-Time Phase-Resolved Functional Optical Hilbert Transformation" Optics Letters, vol. 27, No. 2, Jan. 15, 2002.
Siavash et al., "Self-Referenced Doppler Optical Coherence Tomography" Optics Letters, vol. 27, No. 23, Dec. 1, 2002.
International Search Report and Written Opinion dated Dec. 20, 2004 for PCT/US04/10152.
Notification Concerning Transmittal of International Preliminary Report on Patentability dated Oct. 13, 2005 for PCT/US04/10152.
International Search Report and Written Opinion dated Mar. 23, 2006 for PCT/US2005/042408.
International Preliminary Report on Patentability dated Jun. 7, 2007 for PCT/US2005/042408.
International Search Report and Written Opinion dated Feb. 28, 2007 for International Application No. PCT/US2006/038277.
International Search Report and Written Opinion dated Jan. 30, 2009 for International Application No. PCT/US2008/081834.
Fox, J.A. et al; "A New Galvanometric Scanner for Rapid tuning of C02 Lasers" New York, IEEE, US vol. Apr. 7, 1991.
Motaghian Nezam, S.M. et al: "High-speed Wavelength-Swept Semiconductor laser using a Diffrection Grating and a Polygon Scanner in Littro Configuration" *Optical Fiber Communication and the National Fiber Optic Engineers Conference* Mar. 29, 2007.
International Search Report and Written Opinion dated Feb. 2, 2009 for International Application No. PCT/US2008/071786.
BTlenca A et al: "The Role of Amplitude andphase in Fluorescence Coherence Imaging: From Wide Filed to Nanometer Depth Profiling", *Optics IEEE*, May 5, 2007.
Inoue, Yusuke et al: "Varible Phase-Contrast Fluorescence Spectrometry for Fluorescently Strained Cells", *Applied Physics Letters*, Sep. 18, 2006.
Bernet, S et al: "Quantitative Imaging of Complex Samples by Spiral Phase Contrast Microscopy", *Optics Express*, May 9, 2006.
International Search Report and Written Opinion dated Jan. 15, 2009 for International Application No. PCT/US2008/074863.
Office Action dated Feb. 17, 2009 for U.S. Appl. No. 11/211,483.
Notice of Reasons for Rejection mailed Dec. 2, 2008 for Japanese patent application No. 2000-533782.
International Search Report and Written Opinion dated Feb. 24, 2009 for PCT/US2008/076447.
European Official Action dated Dec. 2, 2008 for EP 07718117.0.

(56) References Cited

OTHER PUBLICATIONS

Barfuss et at (1989) "Modified Optical Frequency Domain Reflectometry with High spatial Resolution for Components of integrated optic Systems", Journal of Lightwave Technology, IEEE vol. 7., No. 1.

Yun et al., (2004) "Removing the Depth-Degeneracy in Optical Frequency Domain Imaging with Frequency Shifting", Optics Express, vol. 12, No. 20.

International Search Report and Written Opinion dated Jun. 10, 2009 for PCT/US08/075456.

European Search Report issued May 5, 2009 for European Application No. 01991471.2.

Motz, J.T. et al: "Spectral-and Frequency-Encoded Fluorescence Imaging" Optics Letters, OSA, Optical Society of America, Washington, DC, US, vol. 30, No. 20, Oct. 15, 2005, pp. 2760-2762.

Japanese Notice of Reasons for Rejection dated Jul. 14, 2009 for Japanese Patent application No. 2006-503161.

Office Action dated Aug. 18, 2009 for U.S. Appl. No. 12/277,178.

Office Action dated Aug. 13, 2009 for U.S. Appl. No. 10/136,813.

Office Action dated Aug. 6, 2009 for U.S. Appl. No. 11/624,455.

Office Action dated May 15, 2009 for U.S. Appl. No. 11/537,123.

Office Action dated Apr. 17, 2009 for U.S. Appl. No. 11/537,343.

Office Action dated Apr. 15, 2009 for U.S. Appl. No. 12/205,775.

Fujimoto et al., "High Resolution in Vivo Intra-Arterial Imaging with Optical Coherence Tomography," *Official Journal of the British Cardiac Society*, vol. 82, pp. 128-133 Heart, 1999.

D. Huang et al., "Optical Coherence Tomography," *Science*, vol. 254, pp. 1178-1181, Nov. 1991.

Tearney et al., "High-Speed Phase—and Group Delay Scanning with a Grating Based Phase Control Delay Line," *Optics Letters*, vol. 22, pp. 1811-1813, Dec. 1997.

Rollins, et al., "In Vivo Video Rate Optical Coherence Tomography," *Optics Express*, vol. 3, pp. 219-229, Sep. 1998

Saxer, et al., High Speed Fiber-Based Polarization-Sensitive Optical Coherence Tomography of in Vivo Human Skin, *Optical Society of America*, vol. 25, pp. 1355-1357, Sep. 2000.

Oscar Eduardo Martinez, "3000 Times Grating Compress or with Positive Group Velocity Dispersion," *IEEE*, vol. QE-23, pp. 59-64, Jan. 1987.

Kulkarni, et al., "Image Enhancement in Optical Coherence Tomography Using Deconvolution," *Electronics Letters*, vol. 33, pp. 1365-1367, Jul. 1997.

Bashkansky, et al., "Signal Processing for Improving Field Cross-Correlation Function in Optical Coherence Tomography," *Optics & Photonics News*, vol. 9, pp. 8137-8138, Yung et al., "Phase-Domain Processing of Optical Coherence Tomography Images," *Journal of Biomedical Optics*, vol. 4, pp. 125-136, Jan. 1999.

Tearney, et al., "In Vivo Endoscopic Optical Biopsy with Optical Coherence Tomography," *Science*, vol. 276, Jun. 1997.

W. Drexler et al., "In Vivo Ultrahigh-Resolution Optical Coherence Tomography," *Optics Letters*, vol. 24, pp. 1221-1223, Sep. 1999.

Nicusor V. Iftimia et al., (2005) "A Portable, Low Coherence Interferometry Based Instrument for Fine Needle Aspiration Biopsy Guidance," Accepted to Review of Scientific Instruments, published May 23, 2005.

Abbas, G.L., V.W.S. Chan et al., "Local-Oscillator Excess-Noise Suppression for Homodyne and Heterodyne-Detection," *Optics Letters*, vol. 8, pp. 419-421, Aug. 1983 issue.

Agrawal, G.P., "Population Pulsations and Nondegenerate 4-Wave Mixing in Semiconductor-Lasers and Amplifiers," *Journal of the Optical Society of America B-Optical Physics*, vol. 5, pp. 147-159, Jan. 1998.

Andretzky, P. et al., "Optical Coherence Tomography by Spectral Radar: Improvement of Signal-to-Noise Ratio," *The International Society for Optical Engineering*, USA, vol. 3915, 2000.

Ballif, J. et al., "Rapid and Scalable Scans at 21 m/s in optical Low-Coherence Reflectometry," *Optics Letters*, vol. 22, pp. 757-759, Jun. 1997.

Barfuss H. et al., "Modified Optical Frequency-Domain Reflectometry with High Spatial-Resolution for Components of Integrated Optic Systems," *Journal of Lightwave Technology*, vol. 7, pp. 3-10, Jan. 1989.

Beaud, P. et al., "Optical Reflectometry with Micrometer Resolution for the Investigation of Integrated Optical-Devices," *Leee Journal of Quantum Electronics*, vol. 25, pp. 755-759, Apr. 1989.

Bouma, Brett et al., "Power-Efficient Nonreciprocal Interferometer and Linear-Scanning Fiber-Optic Catheter for Optical Coherence Tomography," *Optics Letters*, vol. 24, pp. 531-533, Apr. 1999.

Brinkmeyer, E. et al., "Efficient Algorithm for Non-Equidistant Interpolation of Sampled Data," *Electronics Letters*, vol. 28, p. 693, Mar. 1992.

Brinkmeyer, E. et al., "High-Resolution OCDR in Dispersive Wave-Guides," *Electronics Letters*, vol. 26, pp. 413-414, Mar. 1990.

Chinn, S.R. et al., "Optical Coherence Tomography Using a Frequency-Tunable Optical Source," *Optics Letters*, vol. 22, pp. 340-342, Mar. 1997.

Danielson, B.L. et al., "Absolute Optical Ranging Using Low Coherence Interferometry," *Applied Optics*, vol. 30, p. 2975, Jul. 1991.

Dorrer, C. et al., "Spectral Resolution and Sampling Issues in Fourier-Transform Spectral Interferometry," *Journal of the Optical Society of America B-Optical Physics*, vol. 17, pp. 1795-1802, Oct. 2000.

Dudley, J.M. et al., "Cross-Correlation Frequency Resolved Optical Gating Analysis of Broadband Continuum Generation in Photonic Crystal Fiber: Simulations and Experiments," *Optics Express*, vol. 10, p. 1215, Oct. 2002.

Eickhoff, W. et al., "Optical Frequency-Domain Reflectometry in Single-Mode Fiber," *Applied Physics Letters*, vol. 39, pp. 693-695, 1981.

Fercher, Adolf "Optical Coherence Tomography," *Journal of Biomedical Optics*, vol. 1, pp. 157-173, Apr. 1996.

Ferreira, L.A. et al., "Polarization-Insensitive Fiberoptic White-Light Interferometry," *Optics Communications*, vol. 114, pp. 386-392, Feb. 1995.

Fujii, Yohji, "High-Isolation Polarization-Independent Optical Circulator", *Journal of Lightwave Technology*, vol. 9, pp. 1239-1243, Oct. 1991.

Glance, B., "Polarization Independent Coherent Optical Receiver," *Journal of Lightwave Technology*, vol. LT-5, p. 274, Feb. 1987.

Glombitza, U., "Coherent Frequency-Domain Reflectometry for Characterization of Single-Mode Integrated-Optical Wave-Guides," *Journal of Lightwave Technology*, vol. 11, pp. 1377-1384, Aug. 1993.

Golubovic, B. et al., "Optical Frequency-Domain Reflectometry Using Rapid Wavelength Tuning of a Cr4+:Forsterite Laser," *Optics Letters*, vol. 11, pp. 1704-1706, Nov. 1997.

Haberland, U. H. P. et al., "Chirp Optical Coherence Tomography of Layered Scattering Media," *Journal of Biomedical Optics*, vol. 3, pp. 259-266, Jul. 1998.

Hammer, Daniel X. et al., "Spectrally Resolved White-Light Interferometry for Measurement of Ocular Dispersion," *Journal of the Optical Society of America A-Optics Image Science and Vision*, vol. 16, pp. 2092-2102, Sep. 1999.

Harvey, K. C. et al., "External-Cavity Diode-Laser Using a Grazing-Incidence Diffraction Grating," *Optics Letters*, vol. 16, pp. 910-912, Jun. 1991.

Hausler, Gerd et al., "'Coherence Radar' and 'Spectral Radar' New Tools for Dermatological Diagnosis," *Journal of Biomedical Optics*, vol. 3, pp. 21-31, Jan. 1998.

Hee, Michael R. et al., "Polarization-Sensitive Low-Coherence Reflectometer for Birefringence Characterization and Ranging," *Journal of the Optical Society of America B (Optical Physics)*, vol. 9, p. 903-908, Jun. 1992.

Hotate Kazuo et al., "Optical Coherence Domain Reflectometry by Synthesis of Coherence Function," *Journal of Lightwave Technology*, vol. 11, pp. 1701-1710, Oct. 1993.

Inoue, Kyo et al., "Nearly Degenerate 4-Wave-Mixing in a Traveling-Wave Semiconductor-Laser Amplifier," *Applied Physics Letters*, vol. 51, pp. 1051-1053, 1987.

Ivanov, A. P. et al., "New Method for High-Range Resolution Measurements of Light Scattering in Optically Dense Inhomogeneous Media," *Optics Letters*, vol. 1, pp. 226-228, Dec. 1977.

(56) References Cited

OTHER PUBLICATIONS

Ivanov, A. P. et al., "Interferometric Study of the Spatial Structure of a Light-Scattering Medium," *Journal of Applied Spectroscopy*, vol. 28, pp. 518-525, 1978.

Kazovsky, L. G. et al., "Heterodyne Detection Through Rain, Snow, and Turbid Media: Effective Receiver Size at Optical Through Millimeter Wavelenghths," *Applied Optics*, vol. 22, pp. 706-710, Mar. 1983.

Kersey, A. D. et al., "Adaptive Polarization Diversity Receiver Configuration for Coherent Optical Fiber Communications," *Electronics Letters*, vol. 25, pp. 275-277, Feb. 1989.

Kohlhaas, Andreas et al., "High-Resolution OCDR for Testing Integrated-Optical Waveguides: Dispersion-Corrupted Experimental Data Corrected by a Numerical Algorithm," *Journal of Lightwave Technology*, vol. 9, pp. 1493-1502, Nov. 1991.

Larkin, Kieran G., "Efficient Nonlinear Algorithm for Envelope Detection in White Light Interferometry," *Journal of the Optical Society of America A-Optics Image Science and Vision*, vol. 13, pp. 832-843, Apr. 1996.

Leitgeb, R. et al., "Spectral measurement of Absorption by Spectroscopic Frequency-Domain Optical Coherence Tomography," *Optics Letters*, vol. 25, pp. 820-822, Jun. 2000.

Lexer, F. et al., "Wavelength-Tuning Interferometry of Intraocular Distances," *Applied Optics*, vol. 36, pp. 6548-6553, Sep. 1997.

Mitsui, Takahisa, "Dynamic Range of Optical Reflectometry with Spectral Interferometry," *Japanese Journal of Applied Physics Part 1-Regular Papers Short Notes & Review Papers*, vol. 38, pp. 6133-6137, 1999.

Naganuma, Kazunori et al., "Group-Delay Measurement Using the Fourier-Transform of an Interferometric Cross-Correlation Generated by White Light," *Optics Letters*, vol. 15, pp. 393-395, Apr. 1990.

Okoshi,Takanori, "Polarization-State Control Schemes for Heterodyne or Homodyne Optical Fiber Communications," *Journal of Lightwave Technology*, vol. LT-3, pp. 1232-1237, Dec. 1995.

Passy, R. et al., "Experimental and Theoretical Investigations of Coherent OFDR with Semiconductor-Laser Sources," *Journal of Lightwave Technology*, vol. 12, pp. 1622-1630, Sep. 1994.

Podoleanu, Adrian G., "Unbalanced Versus Balanced Operation in an Optical Coherence Tomography System," *Applied Optics*, vol. 39, pp. 173-182, Jan. 2000.

Price, J. H. V. et al., "Tunable, Femtosecond Pulse Source Operating in the Range 1.06-1.33 mu m Based on an Yb3+-doped Holey Fiber Amplifier," *Journal of the Optical Society of America B-Optical Physics*, vol. 19, pp. 1286-1294, Jun. 2002.

Schmitt, J. M. et al, "Measurement of Optical-Properties of Biological Tissues by Low-Coherence Reflectometry," *Applied Optics*, vol. 32, pp. 6032-6042, Oct. 1993.

Silberberg, Y. et al., "Passive-Mode Locking of a Semiconductor Diode-Laser," *Optics Letters*, vol. 9, pp. 507-509, Nov. 1984.

Smith, L. Montgomery et al., "Absolute Displacement Measurements Using Modulation of the Spectrum of White-Light in a Michelson Interferometer," *Applied Optics*, vol. 28, pp. 3339-3342, Aug. 1989.

Sonnenschein, C. M. et al., "Signal-To-Noise Relationships for Coaxial Systems that Heterodyne Backscatter from Atmosphere," *Applied Optics*, vol. 10, pp. 1600-1604, Jul. 1971.

Sorin, W. V. et al., "Measurement of Rayleigh Backscattering at 1.55 mu m with 32 mu m Spatial Resolution," *IEEE Photonics Technology Letters*, vol. 4, pp. 374-376, Apr. 1992.

Sorin, W. V. et al., "A Simple Intensity Noise-Reduction Technique for Optical Low-Coherence Reflectometry," *IEEE Photonics Technology Letters*, vol. 4, pp. 1404-1406, Dec. 1992.

Swanson, E. A. et al., "High-Speed Optical Coherence Domain Reflectometry," *Optics Letters*, vol. 17, pp. 151-153, Jan. 1992.

Takada, K. et al., "High-Resolution OFDR with Incorporated Fiberoptic Frequency Encoder," *IEEE Photonics Technology Letters*, vol. 4, pp. 1069-1072, Sep. 1992.

Takada, Kazumasa et al., "Narrow-Band light Source with Acoustooptic Tunable Filter for Optical Low-Coherence Reflectometry," *IEEE Photonics Technology Letters*, vol. 8, pp. 658-660, May, 1996.

Takada, Kazumasa et al., "New Measurement System for Fault Location in Optical Wave-Guide Devices Based on an Interometric-Technique," *Applied Optics*, vol. 26, pp. 1603-1606, May 1987.

Tateda, Mitsuhiro et al., "Interferometric Method for Chromatic Dispersion Measurement in a Single-Mode Optical Fiber," *IEEE Journal of Quantum Electronics*, vol. 17, pp. 404-407, Mar. 1981.

Toide, M. et al., "Two-Dimensional Coherent Detection Imaging in Multiple Scattering Media Based the Directional Resolution Capability of the Optical Heterodyne Method," *Applied Physics B (Photophysics and Laser Chemistry)*, vol. B52, pp. 391-394, 1991.

Trutna, W. R. et al., "Continuously Tuned External-Cavity Semiconductor-Laser," *Journal of Lightwave Technology*, vol. 11, pp. 1279-1286, Aug. 1993.

Uttam, Deepak et al., "Precision Time Domain Reflectometry in Optical Fiber Systems Using a Frequency Modulated Continuous Wave Ranging Technique," *Journal of Lightwave Technology*, vol. 3, pp. 971-977, Oct. 1985.

Von Der Weid, J. P. et al., "On the Characterization of Optical Fiber Network Components with Optical Frequency Domain Reflectometry," *Journal of Lightwave Technology*, vol. 15, pp. 1131-1141, Jul. 1997.

Wysocki, P.F. et al., "Broad-Spectrum, Wavelength-Swept, Erbium-Doped Fiber Laser at 1.55-Mu-M," *Optics Letters*, vol. 15, pp. 879-881, Aug. 1990.

Youngquist, Robert C. et al., "Optical Coherence-Domain Reflectometry—A New Optical Evaluation Technique," *Optics Letters*, vol. 12, pp. 158-160, Mar. 1987.

Yun, S. H. et al., "Wavelength-Swept Fiber Laser with Frequency Shifted Feedback and Resonantly Swept Intra-Cavity Acoustooptic Tunable Filter," *IEEE Journal of Selected Topics in Quantum Electronics*, vol. 3, pp. 1087-1096, Aug. 1997.

Yun, S. H. et al., "Interrogation of Fiber Grating Sensor Arrays with a Wavelength-Swept Fiber Laser," *Optics Letters*, vol. 23, pp. 843-845, Jun. 1998.

Yung, K. M., "Phase-Domain Processing of Optical Coherence Tomography Images," *Journal of Biomedical Optics*, vol. 4, pp. 125-136, Jan. 1999.

Zhou, Xiao-Qun et al., "Extended-Range Fmcw Reflectometry Using an optical Loop with a Frequency Shifter," *IEEE Photonics Technology Letters*, vol. 8, pp. 248-250, Feb. 1996.

Zorabedian, Paul et al., "Tuning Fidelity of Acoustooptically Controlled External Cavity Semiconductor-Lasers," *Journal of Lightwave Technology*, vol. 13, pp. 62-66, Jan. 1995.

Victor S. Y. Lin et al., "A Porous Silicon-Based Optical Interferometric Biosensor," *Science Magazine*, vol. 278, pp. 840-843, Oct. 31, 1997.

De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.

Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.

Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.

Roth, Jonathan E. et al., "Simplified Method for Polarization-Sensitive Optical Coherence Tomography," *Optics Letters*, vol. 26, No. 14, Jul. 15, 2001, pp. 1069-1071.

Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.

Wang, Xuedong et al., (2001) "Propagation of Polarized Light in Birefringent Turbid Media: Time-Resolved Simulations," Optical Imaging Laboratory, Biomedical Engineering Program, Texas A&M University, Aug. 27, 2001, pp. 254-259.

(56) References Cited

OTHER PUBLICATIONS

Wong, Brian J.F. et al., "Optical Coherence Tomography of the Rat Cochlea," Journal of *Biomedical Optics*, vol. 5, No. 4, Oct. 2000, pp. 367-370.

Yao, Gang et al., "Propagation of Polarized Light in Turbid Media: Simulated Animation Sequences," *Optics Express*, vol. 7, No. 5, Aug. 28, 2000, pp. 198-203.

Wang, Xiao-Jun et al., "Characterization of Dentin and Enamel by Use of Optical Coherence Tomography," *Applied Optics*, vol. 38, No. 10, Apr. 1, 1999, pp. 2092-2096.

De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.

Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.

Groner, Warren et al., "Orthogonal Polarization Spectral Imaging: A New Method for Study of the Microcirculation," *Nature Medicine Inc.*, vol. 5 No. 10, Oct. 1999, pp. 1209-1213.

De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.

Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.

Lu, Shih-Yau et al., "Homogeneous and Inhomogeneous Jones Matrices," *J. Opt. Soc. Am. A.*, vol. 11, No. 2, Feb. 1994, pp. 766-773.

Bickel, S. William et al., "Stokes Vectors, Mueller Matrices, and Polarized Scattered Light," *Am. J. Phys.*, vol. 53, No. 5, May 1985 pp. 468-478.

Brehonnet, F. Le Roy et al., "Optical Media and Target Characterization by Mueller Matrix Decomposition," *J. Phys. D: Appl. Phys.* 29, 1996, pp. 34-38.

Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.

De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.

De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.

Everett, M.J. et al., "Birefringence Characterization of Biological Tissue by Use of Optical Coherence Tomography," *Optics Letters*, vol. 23, No. 3, Feb. 1, 1998, pp. 228-230.

Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.

Barakat, Richard, "Statistics of the Stokes Parameters," *J. Opt. Soc. Am, B.*, vol. 4, No. 7, Jul. 1987, pp. 1256-1263.

Schmitt, J.M. et al., "Cross-Polarized Backscatter in Optical Coherence Tomography of Biological Tissue," *Optics Letters*, vol. 23, No. 13, Jul. 1, 1998, pp. 1060-1062.

Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.

Pierce, Mark C. et al., "Simultaneous Intensity, Birefringence, and Flow Measurements with High-Speed Fiber-Based Optical Coherence Tomography," *Optics Letters*, vol. 27, No. 17, Sep. 1, 2002, pp. 1534-1536.

De Boer, Johannes F. et al., "Review of Polarization Sensitive Optical Coherence Tomography and Stokes Vector Determination," *Journal of Biomedical Optics*, Jul. 2002, vol. 7, No. 3, pp. 359-371.

Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.

Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.

Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.

Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.

Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.

Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.

Tripathi, Renu et al., "Spectral Shaping for Non-Gaussian Source Spectra in Optical Coherence Tomography," *Optics Letters*, vol. 27, No. 6, Mar. 15, 2002, pp. 406-408.

Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.

White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.

De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.

Jiao, Shuliang et al., "Optical-Fiber-Based Mueller Optical Coherence Tomography," *Optics Letters*, vol. 28, No. 14, Jul. 15, 2003, pp. 1206-1208.

Jiao, Shuliang et al., "Contrast Mechanisms in Polarization-Sensitive Mueller-Matrix Optical Coherence Tomography and Application in Burn Imaging," *Applied Optics*, vol. 42, No. 25, Sep. 1, 2003, pp. 5191-5197.

Moreau, Julien et al., "Full-Field Birefringence Imaging by Thermal-Light Polarization-Sensitive Optical Coherence Tomography. I. Theory," *Applied Optics*, vol. 42, No. 19, Jul. 1, 2003, pp. 3800-3810.

Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.

Morgan, Stephen P. et al., "Surface-Reflection Elimination in Polarization Imaging of Superficial Tissue," *Optics Letters*, vol. 28, No. 2, Jan. 15, 2003, pp. 114-116.

Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.

Park, B. Hyle et al., "Real-Time Multi-Functional Optical Coherence Tomography," *Optics Express*, vol. 11, No. 7, Apr. 7, 2003, pp. 782-793.

Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.

Somervell, A.R.D. et al., "Direct Measurement of Fringe Amplitude and Phase Using a Heterodyne Interferometer Operating in Broadband Light," *Elsevier, Optics Communications*, Oct. 2003.

Stifter, D. et al., "Polarisation-Sensitive Optical Coherence Tomography for Material Characterisation and Strain-Field Mapping," Applied Physics A 76, Materials Science & Processing, Jan. 2003, pp. 947-951.

(56) References Cited

OTHER PUBLICATIONS

Davé, Digant P. et al., "Polarization-Maintaining Fiber-Based Optical Low-Coherence Reflectometer for Characterization and Ranging of Birefringence," *Optics Letters*, vol. 28, No. 19, Oct. 1, 2003, pp. 1775-1777.

Yang, Ying et al., "Observations of Birefringence in Tissues from Optic-Fibre-Based Optical Coherence Tomography," *Measurement Science and Technology*, Nov. 2002, pp. 41-46.

Yun, S.H. et al., "High-Speed Optical Frequency-Domain Imaging," *Optics Express*, vol. 11, No. 22, Nov. 3, 2003, pp. 2953-2963.

Yun, S.H. et al., "High-Speed Spectral-Domain Optical Coherence Tomography at 1.3 µm Wavelength," *Optics Express*, vol. 11, No. 26, Dec. 29, 2003, pp. 3598-3604.

Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.

Pircher, Michael et al., "Three Dimensional Polarization Sensitive OCT of Human Skin In Vivo," 2004, *Optical Society of America*.

Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.

Guo, Shuguang et al., "Depth-Resolved Birefringence and Differential Optical Axis Orientation Measurements with Finer-based Polarization-Sensitive Optical Coherence Tomography," *Optics Letters*, vol. 29, No. 17, Sep. 1, 2004, pp. 2025-2027.

Huang, Xiang-Run et al., "Variation of Peripapillary Retinal Nerve Fiber Layer Birefringence in Normal Human Subjects," *Investigative Ophthalmology & Visual Science*, vol. 45, No. 9, Sep. 2004, pp. 3073-3080.

Matcher, Stephen J. et al., "The Collagen Structure of Bovine Intervertebral Disc Studied Using Polarization-Sensitive Optical Coherence Tomography," *Physics in Medicine and Biology*, 2004, pp. 1295-1306.

Nassif, Nader et al., "In Vivo Human Retinal Imaging by Ultrahigh-Speed Spectral Domain Optical Coherence Tomography," *Optics Letters*, vol. 29, No. 5, Mar. 1, 2004, pp. 480-482.

Nassif, N.A. et al., "In Vivo High-Resolution Video-Rate Spectral-Domain Optical Coherence Tomography of the Human Retina and Optic Nerve," *Optics Express*, vol. 12, No. 3, Feb. 9, 2004, pp. 367-376.

Park, B. Hyle et al., "Comment on Optical-Fiber-Based Mueller Optical Coherence Tomography," *Optics Letters*, vol. 29, No. 24, Dec. 15, 2004, pp. 2873-2874.

Park, B. Hyle et al., "Jones Matrix Analysis for a Polarization-Sensitive Optical Coherence Tomography System Using Fiber-Optic Components," *Optics Letters*, vol. 29, No. 21, Nov. 1, 2004, pp. 2512-2514.

Pierce, Mark C. et al., "Collagen Denaturation can be Quantified in Burned Human Skin Using Polarization-Sensitive Optical Coherence Tomography," *Elsevier, Burns*, 2004, pp. 511-517.

Pierce, Mark C. et al., "Advances in Optical Coherence Tomography Imaging for Dermatology," *The Society for Investigative Dermatology, Inc.* 2004, pp. 458-463.

Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.

Cense, Barry et al., "In Vivo Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125.

Pircher, Michael et al., "Imaging of Polarization Properties of Human Retina in Vivo with Phase Resolved Transversal PS-OCT," *Optics Express*, vol. 12, No. 24, Nov. 29, 2004 pp. 5940-5951.

Pircher, Michael et al., "Transversal Phase Resolved Polarization Sensitive Optical Coherence Tomography," *Physics in Medicine & Biology*, 2004, pp. 1257-1263.

Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.

Strasswimmer, John et al., "Polarization-Sensitive Optical Coherence Tomography of Invasive Basal Cell Carcinoma," *Journal of Biomedical Optics*, vol. 9, No. 2, Mar./Apr. 2004, pp. 292-298.

Todorovio, Milog et al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404

Yasuno, Yoshiaki et al., "Polarization-Sensitive Complex Fourier Domain Optical Coherence Tomography for Jones Matrix Imaging of Biological Samples," *Applied Physics Letters*, vol. 85, No. 15, Oct. 11, 2004, pp. 3023-3025.

Acioli, L. H., M. Ulman, et al. (1991). "Femtosecond Temporal Encoding in Barium-Titanate." *Optics Letters* 16(24): 1984-1986.

Aigouy, L., A. Lahrech, et al. (1999). "Polarization effects in apertureless scanning near-field optical microscopy: an experimental study." *Optics Letters* 24(4): 187-189.

Akiba, M., K. P. Chan, et al. (2003). "Full-field optical coherence tomography by two-dimensional heterodyne detection with a pair of CCD cameras." *Optics Letters* 28(10): 816-818.

Akkin, T., D. P. Dave, et al. (2004). "Detection of neural activity using phase-sensitive optical low-coherence reflectometry." *Optics Express* 12(11): 2377-2386.

Akkin, T., D. P. Dave, et al. (2003). "Surface analysis using phase sensitive optical low coherence reflectometry." *Lasers in Surgery and Medicine*: 4-4.

Akkin, T., D. P. Dave, et al. (2003). "Imaging tissue response to electrical and photothermal stimulation with nanometer sensitivity." *Lasers in Surgery and Medicine* 33(4): 219-225.

Akkin, T., T. E. Milner, et al. (2002). "Phase-sensitive measurement of birefringence change as an indication of neural functionality and diseases." *Lasers in Surgery and Medicine*: 6-6.

Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." *Proceedings of SPIE—The International Society for Optical Engineering* 3567: pp. 78-87.

Antcliff, R. J., T. J. ffytche, et al. (2000). "Optical coherence tomography of melanocytoma." *American Journal of Ophthalmology* 130(6): 845-7.

Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.

Anvari, B., T. E. Milner, et al. (1995). "Selective Cooling of Biological Tissues—Application for Thermally Mediated Therapeutic Procedures." *Physics in Medicine and Biology* 40(2): 241-252.

Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." *Physics in Medicine and Biology* 40(9): 1451-1465.

Arend, O., M. Ruffer, et al. (2000). "Macular circulation in patients with diabetes mellitus with and without arterial hypertension." *British Journal of Ophthalmology* 84(12): 1392-1396.

Arimoto, H. and Y. Ohtsuka (1997). "Measurements of the complex degree of spectral coherence by use of a wave-front-folded interferometer." *Optics Letters* 22(13): 958-960.

Azzolini, C., F. Patelli, et al. (2001). "Correlation between optical coherence tomography data and biomicroscopic interpretation of idiopathic macular hole." *American Journal of Ophthalmology* 132(3): 348-55.

Baba, T., K. Ohno-Matsui, et al. (2002). "Optical coherence tomography of choroidal neovascularization in high myopia." *Acta Ophthalmoloqica Scandinavica* 80(1): 82-7.

Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." *Proc. SPIE*, 2925: p. 298-303.

Baney, D. M. and W. V. Sorin (1993). "Extended-Range Optical Low-Coherence Reflectometry Using a Recirculating Delay Technique." *Ieee Photonics Technology Letters* 5(9): 1109-1112.

(56) References Cited

OTHER PUBLICATIONS

Baney, D. M., B. Szafraniec, et al. (2002). "Coherent optical spectrum analyzer." *Ieee Photonics Technology Letters* 14(3): 355-357.

Barakat, R. (1981). "Bilinear Constraints between Elements of the 4by4 Mueller-Jones Transfer-Matrix of Polarization Theory." *Optics Communications* 38(3): 159-161.

Barakat, R. (1993). "Analytic Proofs of the Arago-Fresnel Laws for the Interference of Polarized-Light." *Journal of the Optical Society of America a-Optics Image Science and Vision* 10(1): 180-185.

Barbastathis, G. and D. J. Brady (1999). "Multidimensional tomographic imaging using volume holography." *Proceedings of the Ieee* 87(12): 2098-2120.

Bardal, S., A. Kamal, et al. (1992). "Photoinduced Birefringence in Optical Fibers—a Comparative-Study of Low-Birefringence and High-Birefringence Fibers." *Optics Letters* 17(6): 411-413.

Barsky, S. H., S. Rosen, et al. (1980). "Nature and Evolution of Port Wine Stains—Computer-Assisted Study." *Journal of Investigative Dermatology* 74(3): 154-157.

Barton, J. K., J. A. Izatt, et al. (1999). "Three-dimensional reconstruction of blood vessels from in vivo color Doppler optical coherence tomography images." *Dermatology* 198(4): 355-361.

Barton, J. K., A. Rollins, et al. (2001). "Photothermal coagulation of blood vessels: a comparison of high-speed optical coherence tomography and numerical modelling." *Physics in Medicine and Biology* 46.

Barton, J. K., A. J. Welch, et al. (1998). "Investigating pulsed dye laser-blood vessel interaction with color Doppler optical coherence tomography." *Optics Express* 3.

Bashkansky, M., M. D. Duncan, et al. (1997). "Subsurface defect detection in ceramics by highspeed high-resolution optical coherent tomography." *Optics Letters* 22 (1): 61-63.

Bashkansky, M. and J. Reintjes (2000). "Statistics and reduction of speckle in optical coherence tomography." *Optics Letters* 25(8): 545-547.

Baumgartner, A., S. Dichtl, et al. (2000). "Polarization-sensitive optical coherence tomography of dental structures." *Caries Research* 34(1): 59-69.

Baumgartner, A., C. K. Hitzenberger, et al. (2000). "Resolution-improved dual-beam and standard optical coherence tomography: a comparison." *Graefes Archive for Clinical and Experimental Ophthalmology* 23 8(5): 385-392.

Baumgartner, A., C. K. Hitzenberger, et al. (1998). "Signal and resolution enhancements in dual beam optical coherence tomography of the human eye." *Journal of Biomedical Optics* 3(1): 45-54.

Beaurepaire, E., P. Gleyzes, et at. (1998). *Optical coherence microscopy for the in-depth study of biological structures: System based on a parallel detection scheme*, Proceedings of SPIE—The International Society for Optical Engineering.

Beaurepaire, E., L. Moreaux, et al. (1999). "Combined scanning optical coherence and two-photonexcited fluorescence microscopy." *Optics Letters* 24(14): 969-971.

Bechara, F. G., T. Gambichler, et al. (2004). "Histomorphologic correlation with routine histology and optical coherence tomography." *Skin Research and Technology* 10 (3): 169-173.

Bechmann, M., M. J. Thiel, et al. (2000). "Central corneal thickness determined with optical coherence tomography in various types of glaucoma. [see comments]." *British Journal of Ophthalmology* 84(11): 1233-7.

Bek, T. and M. Kandi (2000). "Quantitative anomaloscopy and optical coherence tomography scanning in central serous chorioretinopathy." *Acta Ophthalmologica Scandinavica* 78(6): 632-7.

Benoit, A. M., K. Naoun, et al. (2001). "Linear dichroism of the retinal nerve fiber layer expressed with Mueller matrices." *Applied Optics* 40(4): 565-569.

Bicout, D., C. Brosseau, et al. (1994). "Depolarization of Multiply Scattered Waves by Spherical Diffusers—Influence of the Size Parameter." *Physical Review* E 49(2): 1767-1770.

Blanchot, L., M. Lebec, et al. (1997). *Low-coherence in depth microscopy for biological tissues imaging: Design of a real time control system*. Proceedings of SPIE—The International Society for Optical Engineering.

Blumenthal, E. Z. and R. N. Weinreb (2001). "Assessment of the retinal nerve fiber layer in clinical trials of glaucoma neuroprotection. [Review] [36 refs]." *Survey of Ophthalmology* 45(Suppl 3): S305-12; discussion S332-4.

Blumenthal, E. Z., J. M. Williams, et al. (2000). "Reproducibility of nerve fiber layer thickness measurements by use of optical coherence tomography." *Ophthalmology* 107(12): 2278-82.

Boppart, S. A., B. E. Bouma, et al. (1996). "Imaging developing neural morphology using optical coherence tomography." *Journal of Neuroscience Methods* 70.

Boppart, S. A., B. E. Bouma, et al. (1997). "Forward-imaging instruments for optical coherence tomography." *Optics Letters* 22.

Boppart, S. A., B. E. Bouma, et al. (1998). "Intraoperative assessment of microsurgery with three-dimensional optical coherence tomography." *Radiology* 208: 81-86.

Boppart, S. A., J. Herrmann, et al. (1999). "High-resolution optical coherence tomography-guided laser ablation of surgical tissue." *Journal of Surgical Research* 82(2): 275-84.

Bouma, B. E. and J. G. Fujimoto (1996). "Compact Kerr-lens mode-locked resonators." *Optics Letters* 21. 134-136.

Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3. 76-79.

Bouma, B. E., M. Ramaswamy-Paye, et al. (1997). "Compact resonator designs for mode-locked solid-state lasers." *Applied Physics B (Lasers and Optics)* B65. 213-220.

Bouma, B. E. and G. J. Tearney (2002). "Clinical imaging with optical coherence tomography." *Academic Radiology* 9(8): 942-953.

Bouma, B. E., G. J. Tearney, et al. (1996). "Self-phase-modulated Kerr-lens mode-locked Cr:forsterite laser source for optical coherence tomography." *Optics Letters* 21(22): 1839.

Bouma, B. E., G. J. Tearney, et al. (2000). "High-resolution imaging of the human esophagus and stomach in vivo using optical coherence tomography." *Gastrointestinal Endoscopy* 51(4): 467-474.

Bouma, B. E., G. J. Tearney, et al. (2003). "Evaluation of intracoronary stenting by intravascular optical coherence tomography." *Heart* 89(3): 317-320.

Bourquin, S., V. Monterosso, et al. (2000). "Video-rate optical low-coherence reflectometry based on a linear smart detector array." *Optics Letters* 25(2): 102-104.

Bourquin, S., P. Seitz, et al. (2001). "Optical coherence topography based on a two-dimensional smart detector array." *Optics Letters* 26(8): 512-514.

Bouzid, A., M. A. G. Abushagur, et al. "Fiber-optic four-detector polarimeter." *Optics Communications* 118(3-4): 329-334. (1995).

Bowd, C., R. N. Weinreb, et al. (2000). "The retinal nerve fiber layer thickness in ocular hypertensive, normal, and glaucomatous eyes with optical coherence tomography." *Archives of Ophthalmology* 118(1): 22-6.

Bowd, C., L. M. Zangwill, et al. (2001). "Detecting early glaucoma by assessment of retinal nerve fiber layer thickness and visual function." *Investigative Ophthalmology & Visual Science* 42(9): 1993-2003.

Bowd, C., L. M. Zangwill, et al. (2002). "Imaging of the optic disc and retinal nerve fiber layer: the effects of age, optic disc area, refractive error, and gender." *Journal of the Optical Society of America, A, Optics, Image Science, & Vision* 19(1): 197-207.

Brand, S., J. M. Poneros, et al. (2000). "Optical coherence tomography in the gastrointestinal tract." *Endoscopy* 32(10): 796-803.

Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.

Brezinski, M. E., G. J. Tearney, et al. (1996). "Imaging of coronary artery microstructure (in vitro) with optical coherence tomography." *American Journal of Cardiology* 77 (1): 92-93.

(56) References Cited

OTHER PUBLICATIONS

Brezinski, M. E., G. J. Tearney, et al. (1996). "Optical coherence tomography for optical biopsy—Properties and demonstration of vascular pathology." *Circulation* 93(6): 1206-1213.

Brezinski, M. E., G. J. Tearney, et al. (1997). "Assessing atherosclerotic plaque morphology: Comparison of optical coherence tomography and high frequency intravascular ultrasound." *Heart* 77(5): 397-403.

Brink, H. B. K. and G. J. Vanblokland (1988). "Birefringence of the Human Foveal Area Assessed Invivo with Mueller-Matrix Ellipsometry." *Journal of the Optical of America a-optics Image Science and Vision* 5(1): 49-57.

Brosseau, C. and D. Bicout (1994). "Entropy Production in Multiple-Scattering of Light by a Spatially Random Medium." *Physical Review* E 50(6): 4997-5005.

Burgoyne, C. F., D. E. Mercante, et al. (2002). "Change detection in regional and volumetric disc parameters using longitudinal confocal scanning laser tomography." *Ophthalmology* 109(3): 455-66.

Candido, R. and T. J. Allen (2002). "Haemodynamics in microvascular complications in type 1 diabetes." *Diabetes-Metabolism Research and Reviews* 18(4): 286-304.

Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.

Cense, B., N. Nassif, et al. (2004). "Ultrahigh-Resolution High-Speed Retinal Imaging Using Spectral-Domain Optical Coherence Tomography." *Optics Express* 12(11): 2435-2447.

Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.

Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.

Chartier, T., A. Hideur, et al. (2001). "Measurement of the elliptical birefringence of single-mode optical fibers." *Applied Optics* 40(30): 5343-5353.

Chauhan, B. C., J. W. Blanchard, et al. (2000). "Technique for Detecting Serial Topographic Changes in the Optic Disc and Peripapillary Retina Using Scanning Laser Tomograph." *Invest Ophthalmol Vis Sci* 41: 775-782.

Chen, Z. P., T. E. Milner, et al. (1997). "Optical Doppler tomographic imaging of fluid flow velocity in highly scattering media." *Optics Letters* 22(1): 64-66.

Chen, Z. P., T. E. Milner, et al. (1997). "Noninvasive imaging of in vivo blood flow velocity using optical Doppler tomography." *Optics Letters* 22(14): 1119-1121.

Chen, Z. P., Y. H. Zhao, et al. (1999). "Optical Doppler tomography." *Ieee Journal of Selected Topics in Quantum Electronics* 5(4): 1134-1142.

Cheong, W. F., S. A. Prahl, et al. (1990). "A Review of the Optical-Properties of Biological Tissues." *Ieee Journal of Quantum Electronics* 26(12): 2166-2185.

Chernikov, S. V., Y. Zhu, et al. (1997). "Supercontinuum self-Q-switched ytterbium fiber laser." *Optics Letters* 22(5): 298-300.

Cho, S. H., B. E. Bouma, et al. (1999). "Low-repetition-rate high-peak-power Kerr-lens mode-locked Ti:Al/sub 2/0/sub 3/ laser with a multiple-pass cavity." *Optics Letters* 24(6): 417-419.

Choma, M. A., M. V. Sarunic, et al. (2003). "Sensitivity advantage of swept source and Fourier domain optical coherence tomography." *Optics Express* 11(18): 2183-2189.

Choma, M. A., C. H. Yang, et al. (2003). "Instantaneous quadrature low-coherence interferometry with 3 × 3 fiber-optic couplers." *Optics Letters* 28(22): 2162-2164.

Choplin, N. T. and D. C. Lundy (2001). "The sensitivity and specificity of scanning laser polarimetry in the detection of glaucoma in a clinical setting." *Ophthalmology* 108 (5): 899-904.

Christens Barry, W. A., W. J. Green, et al. (1996). "Spatial mapping of polarized light transmission in the central rabbit cornea." *Experimental Eye Research* 62(6): 651-662.

Chvapil, M., D. P. Speer, et al. (1984). "Identification of the depth of burn injury by collagen stainability." *Plastic & Reconstructive Surgery* 73(3): 438-41.

Cioffi, G. A. (2001). "Three common of assumptions about ocular blood flow and glaucoma." *Survey Ophthalmology* 45: S325-S331.

Coleman, A. L. (1999). "Glaucoma." *Lancet* 354(9192): 1803-10.

Collaborative Normal-Tension Glaucoma Study Group (1998). "comparison of Glaucomatous Progression Between Untreated Patients With Normal Tension Glaucoma and Patients with Therapeutically Reduced Intraocular Pressures." *Am J Ophthalmol* 126: 487-97.

Collaborative Normal-Tension Glaucoma Study Group (1998). "The effectiveness of intraocular pressure reduction in the treatment of normal-tension glaucoma." *Am J Ophthalmol* 126: 498-505.

Collaborative Normal-Tension Glaucoma Study Group (2001). "Natural History of Normal-Tension Glaucoma." *Ophthalmology* 108: 247-253.

Colston, B. W., M. J. Everett, et al. (1998). "Imaging of hard- and soft-tissue structure in the oral cavity by optical coherence tomography." *Applied Optics* 37(16): 3582-3585.

Colston, B. W., U. S. Sathyam, et al. (1998). "Dental OCT." *Optics Express* 3(6): 230-238.

Congdon, N. G., D. S. Friedman, et al. (2003). "Important causes of visual impairment in the world today." *Jama-Journal of the American Medical Association* 290(15): 2057-2060.

Cregan, R. F., B. J. Mangan, et al. (1999). "Single-mode photonic band gap guidance of light in air." *Science* 285(5433): 1537-1539.

DalMolin, M., A. Galtarossa, et al. (1997). "Experimental investigation of linear polarization in high-birefringence single-mode fibers." *Applied Optics* 36(12): 2526-2528.

Danielson, B. L. and C. D. Whittenberg (1987). "Guided-Wave Reflectometry with Micrometer Resolution." *Applied Optics* 26(14): 2836-2842.

Dave, D. P. and T. E. Milner (2000). "Doppler-angle measurement in highly scattering media." *Optics Letters* 25(20): 1523-1525.

de Boer, J. F., T. E. Milner, et al. (1998). *Two dimensional birefringence imaging in biological tissue using phase and polarization sensitive optical coherence tomography*. Trends in Optics and Photonics (TOPS): Advances in Optical Imaging and Photon Migration, Orlando, USA, Optical Society of America, Washington, DC 1998.

de Boer, J. F., C. E. Saxer, et al. (2001). "Stable carrier generation and phase-resolved digital data processing in optical coherence tomography." *Applied Optics* 40(31): 5787-5790.

Degroot, P. and L. Deck (1993). "3-Dimensional Imaging by Sub-Nyquist Sampling of White-Light Interferograms." *Optics Letters* 18(17): 1462-1464.

Denk, W., J. H. Strickler, et al. (1990). "2-Photon Laser Scanning Fluorescence Microscopy." *Science* 248(4951): 73-76.

Descour, M. R., A. H. O. Karkkainen, et al. (2002). "Toward the development of miniaturized Imaging systems for detection of precancer." *Ieee Journal of Quantum Electronics* 38(2): 122-130.

Dettwiller, L. (1997). "Polarization state interference: A general investigation." *Pure and Applied Optics* 6(1): 41-53.

DiCarlo, C. D., W. P. Roach, et al. (1999). "Comparison of optical coherence tomography imaging of cataracts with histopathology." *Journal of Biomedical Optics* 4.

Ding, Z., Y. Zhao, et al. (2002). "Real-time phase-resolved optical coherence tomography and optical Doppler tomography." *Optics Express* 10(5): 236-245.

Dobrin, P. B. (1996). "Effect of histologic preparation on the cross-sectional area of arterial rings." *Journal of Surgical Research* 61(2): 413-5.

Donohue, D. J., B. J. Stoyanov, et al. (1995). "Numerical Modeling of the Corneas Lamellar Structure and Birefringence Properties." *Journal of the Optical Society of America a-Optics Image Science and Vision* 12(7): 1425-1438.

(56) References Cited

OTHER PUBLICATIONS

Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.

Drexler, W., A. Baumgartner, et al. (1997). "Biometric investigation of changes in the anterior eye segment during accommodation." *Vision Research* 37(19): 2789-2800.

Drexler, W., A. Baumgartner, et al. (1997). "Submicrometer precision biometry of the anterior segment of the human eye." *Investigative Ophthalmology & Visual Science* 38(7): 1304-1313.

Drexler, W., A. Baumgartner, et al. (1998). "Dual beam optical coherence tomography: signal identification for ophthalmologic diagnosis." 9*Journal of Biomedical Optics* 3 (1): 55-65.

Drexler, W., O. Findl, et al. (1998). "Partial coherence interferometry: a novel approach to biometry in cataract surgery." *American Journal of Ophthalmology* 126(4): 524-534.

Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.

Drexler, W., C. K. Hitzenberger, et al. (1998). "Investigation of dispersion effects in ocular media by multiple wavelength partial coherence interferometry." *Experimental Eye Research* 66(1): 25-33.

Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.

Drexler, W., C. K. Hitzenberger, et al. (1995). "Measurement of the Thickness of Fundus Layers by Partial Coherence Tomography." *Optical Engineering* 34(3): 701-710.

Drexler, W., U. Morgner, et al. (2001). "Ultrahigh-resolution ophthalmic optical coherence tomography." *Nature Medicine* 7(4): 502-507.

Drexler, W., U. Morgner, et al. (2001). "Ultrahigh-resolution ophthalmic optical coherence tomography. [erratum appears in Nat Med May 2001;7(5):636.]." *Nature Medicine* 7(4): 502-7.

Drexler, W., H. Sattmann, et al. (2003). "Enhanced visualization of macular pathology with the use of ultrahigh-resolution optical coherence tomography." *Archives of Ophthalmology* 121(5): 695-706.

Drexler, W., D. Stamper, et al. (2001). "Correlation of collagen organization with polarization sensitive imaging of in vitro cartilage: implications for osteoarthritis." *Journal of Rheumatology* 28(6): 1311-8.

Droog, E. J., W. Steenbergen, et al. (2001). "Measurement of depth of burns by laser Doppler perfusion imaging." *Burns* 27(6): 561-8.

Dubois, A., K. Grieve, et al. (2004). "Ultrahigh-resolution full-field optical coherence tomography." *Applied Optics* 43(14): 2874-2883.

Dubois, A., L. Vabre, et al. (2002). "High-resolution full-field optical coherence tomography with a Linnik microscope." *Applied Optics* 41(4): 805-812.

Ducros, M., M. Laubscher, et al. (2002). "Parallel optical coherence tomography in scattering samples using a two-dimensional smart-pixel detector array." *Optics Communications* 202(1-3): 29-35.

Ducros, M. G., J. D. Marsack, et al. (2001). "Primate retina imaging with polarization-sensitive optical coherence tomography." *Journal of the Optical Society of America a-Optics Image Science and Vision* 18(12): 2945-2956.

Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.

Eigensee, A., G. Haeusler, et al. (1996). "New method of short-coherence interferometry in human skin (in vivo) and in solid volume scatterers." *Proceedings of SPIE—The International Society for Optical Engineering* 2925: 169-178.

Eisenbeiss, W., J. Marotz, et al. (1999). "Reflection-optical multispectral imaging method for objective determination of burn depth." *Burns* 25(8): 697-704.

Elbaum, M., M. King, et al. (1972). "Wavelength-Diversity Technique for Reduction of Speckle Size." *Journal of the Optical Society of America* 62(5): 732-&.

Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

Essenpreis, M., C. E. Elwell, et al. (1993). "Spectral Dependence of Temporal Point Spread Functions in Human Tissues." *Applied Optics* 32(4): 418-425.

Eun, H. C. (1995). "Evaluation of skin blood flow by laser Doppler flowmetry. [Review] [151 refs]." *Clinics in Dermatology* 13(4): 337-47.

Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.

Feldchtein, F. I., G. V. Gelikonov, et al. (1998). "In vivo OCT imaging of hard and soft tissue of the oral cavity." *Optics Express* 3(6): 239-250.

Feldchtein, F. I., G. V. Gelikonov, et al. (1998). "Endoscopic applications of optical coherence tomography." *Optics Express* 3(6): 257-270.

Fercher, A. F., W. Drexler, et al. (1997). "Optical ocular tomography." *Neuro-Ophthalmology* 18(2): 39-49.

Fercher, A. F., W. Drexler, et al. (1994). *Measurement of optical distances by optical spectrum modulation*. Proceedings of SPIE—The International Society for Optical Engineering.

Fercher, A. F., W. Drexler, et al. (2003). "Optical coherence tomography—principles and applications." *Reports on Progress in Physics* 66(2): 239-303.

Fercher, A. F., C. Hitzenberger, et al. (1991). "Measurement of Intraocular Optical Distances Using Partially Coherent Laser-Light." *Journal of Modern Optics* 38(7): 1327-1333.

Fercher, A. F., C. K. Hitzenberger, et al. (1996). *Ocular partial coherence interferometry*, Proceedings of SPIE—The International Society for Optical Engineering.

Fercher, A. F., C. K. Hitzenberger, et al. (1993). "In-Vivo Optical Coherence Tomography." *American Journal of Ophthalmology* 116(1): 113-115.

Fercher, A. F., C. K. Hitzenberger, et al. (1994). *In-vivo dual-beam optical coherence tomography*, Proceedings of SPIE—The International Society for Optical Engineering.

Fercher, A. F., C. K. Hitzenberger, et al. (1995). "Measurement of Intraocular Distances by Backscattering Spectral Interferometry." *Optics Communications* 117(1-2): 43-48.

Fercher, A. F., C. K. Hitzenberger, et al. (2000). "A thermal light source technique for optical coherence tomography." *Optics Communications* 185(1-3): 57-64.

Fercher, A. F., C. K. Hitzenberger, et al. (2001). "Numerical dispersion compensation for Partial Coherence Coherence Interferometry and Optical Tomography." *Optics Express* 9(12): 610-615.

Fercher, A. F., C. K. Hitzenberger, et al. (2002). "Dispersion compensation for optical coherence tomography depth- scan signals by a numerical technique." *Optics Communications* 204(1-6): 67-74.

Fercher, A. F., H. C. Li, et al. (1993). "Slit Lamp Laser-Doppler Interferometer." *Lasers in Surgery and Medicine* 13(4): 447-452.

Fercher, A. F., K. Mengedoht, et at. (1988). "Eye-Length Measurement by Interferometry with Partially Coherent-Light." *Optics Letters* 13(3): 186-188.

Ferro, P., M. Haelterman, et al. (1991). "All-Optical Polarization Switch with Long Low-Birefringence Fiber." *Electronics Letters* 27(16): 1407-1408.

Fetterman, M. R., D. Goswami, et al. (1998). "Ultrafast pulse shaping: amplification and characterization." *Optics Express* 3(10): 366-375.

Findl, O., W. Drexler, et al. (2001). "Improved prediction of intraocular lens power using partial coherence interferometry." *Journal of Cataract and Refractive Surgery* 27 (6): 861-867.

Fork, R. L., C. H. B. Cruz, et al. (1987). "Compression of Optical Pulses to 6 Femtoseconds by Using Cubic Phase Compensation." *Optics Letters* 12(7): 483-485.

(56) References Cited

OTHER PUBLICATIONS

Foschini, G. J. and C. D. Poole (1991). "Statistical-Theory of Polarization Dispersion in Single-Mode Fibers." *Journal of Lightwave Technology* 9(11): 1439-1456.
Francia, C., F. Bruyere, et al. (1998). "PMD second-order effects on pulse propagation in single-mode optical fibers." *Ieee Photonics Technology Letters* 10(12): 1739-1741.
Fried, D., R. E. Glena, et al. (1995). "Nature of Light-Scattering in Dental Enamel and Dentin at Visible and near-Infrared Wavelengths." *Applied Optics* 34(7): 1278-1285.
Fujimoto, J. G., M. E. Brezinski, et al. (1995). "Optical Biopsy and Imaging Using Optical Coherence Tomography." *Nature Medicine* 1(9): 970-972.
Fukasawa, A. and H. Iijima (2002). "Optical coherence tomography of choroidal osteoma." *American Journal of Ophthalmology* 133(3): 419-21.
Fymat, A. L. (1981). "High-Resolution Interferometric Spectrophotopolarimetry." *Engineering Optical* 20(1): 25-30.
Galtarossa, A., L. Palmieri, et al. (2000). "Statistical characterization of fiber random birefringence." *Optics Letters* 25(18): 1322-1324.
Galtarossa, A., L. Palmieri, et al. (2000). "Measurements of beat length and perturbation length in long single-mode fibers." *Optics Letters* 25(6): 384-386.
Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.
Garcia, N. and M. Nieto-Vesperinas (2002). "Left-handed materials do not make a perfect lens." *Physical Review Letters* 88(20).
Gelikonov, V. M., G. V. Gelikonov, et al. (1995). "Coherent Optical Tomography of Microscopic Inhomogeneities in Biological Tissues." *Jetp Letters* 61(2): 158-162.
George, N. and A. Jain (1973). "Speckle Reduction Using Multiple Tones of Illumination." *Applied Optics* 12(6): 1202-1212.
Gibson, G. N., R. Klank, et al. (1996). "Electro-optically cavity-dumped ultrashort-pulse Ti:sapphire oscillator." *Optics Letters* 21(14): 1055.
Gil, J. J. (2000). "Characteristic properties of Mueller matrices." *Journal of the Optical Society of America a-Optics Image Science and Vision* 17(2): 328-334.
Gil, J. J. and E. Bernabeu (1987). "Obtainment of the Polarizing and Retardation Parameters of a Nondepolarizing Optical-System from the Polar Decomposition of Its Mueller Matrix." *Optik* 76(2):67-71.
Gladkova, N. D., G. A. Petrova, et al. (2000). "In vivo optical coherence tomography imaging of human skin: norm and pathology." *Skin Research and Technology* 6 (1): 6-16.
Glaessl, A., A. G. Schreyer, et al. (2001). "Laser surgical planning with magnetic resonance imaging-based 3-dimensional reconstructions for intralesional Nd : YAG laser therapy of a venous malformation of the neck." *Archives of Dermatology* 137(10): 1331-1335.
Gloesmann, M., B. Hermann, et al. (2003). "Histologix correlation of pig retina radial stratification with ultrahigh-resolution optical coherence tomography." *Investigative Ophthalmology & Visual Science* 44(4): 1696-1703.
Goldberg, L. and D. Mehuys (1994). "High-Power Superluminescent Diode Source." *Electronics Letters* 30(20): 1682-1684.
Goldsmith, J. A., Y. Li, et al. (2005). "Anterior chamber width measurement by high speed optical coherence tomography." *Ophthalmology* 112(2): 238-244.
Goldstein, L. E., J. A. Muffat, et al. (2003). "Cytosolic beta-amyloid deposition and supranuclear cataracts in lenses from people with Alzheimer's disease." *Lancet* 361(9365): 1258-1265.
Golubovic, B., B. E. Bouma, et al. (1996). "Thin crystal, room-temperature Cr/sup 4 +/:forstefite laser using near-infrared pumping." *Optics Letters* 21(24): 1993-1995.
Gonzalez, S. and Z. Tannous (2002). "Real-time, in vivo confocal reflectance microscopy of basal cell carcinoma." *Journal of the American Academy of Dermatology* 47(6): 869-874.

Gordon, M. O. and M. A. Kass (1999). "The Ocular Hypertension Treatment Study: design and baseline description of the participants." *Archives of Ophthalmology* 117(5): 573-83.
Grayson, T. P., J. R. Torgerson, et al. (1994). "Observation of a Nonlocal Pancharatnam Phase-Shift in the Process of Induced Coherence without Induced Emission." *Physical Review* A 49(1): 626-628.
Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.
Greenfield, D. S., H. Bagga, et al. (2003). "Macular thickness changes in glaucomatous optic neuropathy detected using optical coherence tomography." *Archives of Ophthalmology* 121(1): 41-46.
Greenfield, D. S., R. W. Knighton, et al. (2000). "Effect of corneal polarization axis on assessment of retinal nerve fiber layer thickness by scanning laser polarimetry." *American Journal of Ophthalmology* 129(6): 715-722.
Griffin, R. A., D. D. Sampson, et al. (1995). "Coherence Coding for Photonic Code-Division Multiple-Access Networks." *Journal of Lightwave Technology* 13(9): 1826-1837.
Guedes, V., J. S. Schuman, et al. (2003). "Optical coherence tomography measurement of macular and nerve fiber layer thickness in normal and glaucomatous human eyes." *Ophthalmology* 110(1): 177-189.
Gueugniaud, P. Y., H. Carsin, et al. (2000). "Current advances in the initial management of major thermal burns. [Review] [76 refs]." *Intensive Care Medicine* 26(7): 848-56.
Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.
Gurses-Ozden, R., H. Ishikawa, et al. (1999). "Increasing sampling density improves reproducibility of optical coherence tomography measurements." *Journal of Glaucoma* 8(4): 238-41.
Guzzi, R. (1998). "Scattering Theory from Homogeneous and Coated Spheres." 1-11.
Haberland, U. B., Vladimir; Schmitt, Hans J. (1996). "Optical coherent tomography of scattering media using electrically tunable near-infrared semiconductor laser." *Applied Optics* Draft Copy.
Haberland, U. R., Walter; Blazek, Vladimir; Schmitt, Hans J. (1995). "Investigation of highly scattering media using near-infrared continuous wave tunable semiconductor laser." *Proc. SPIE*, 2389: 503-512.
Hale, G. M. and M. R. Querry (1973). "Optical-Constants of Water in 200-Nm to 200-Mum Wavelength Region." *Applied Optics* 12(3): 555-563.
Hammer, D. X., R. D. Ferguson, et al. (2002). "Image stabilization for scanning laser ophthalmoscopy." *Optics Express* 10(26): 1542.
Hara, T., Y. Ooi, et al. (1989). "Transfer Characteristics of the Microchannel Spatial Light-Modulator." *Applied Optics* 28(22): 4781-4786.
Harland, C. C., S. G. Kale, et al. (2000). "Differentiation of common benign pigmented skin lesions from melanoma by high-resolution ultrasound." *British Journal of Dermatology* 143(2): 281-289.
Hartl, I., X. D. Li, et al. (2001). "Ultrahigh-resolution optical coherence tomography using continuum generation in an air-silica microstructure optical fiber." *Optics Letters* 26(9): 608-610.
Hassenstein, A., A. A. Bialasiewicz, et al. (2000). "Optical coherence tomography in uveitis patients." *American Journal of Ophthalmoloqv* 130(5): 669-70.
Hattenhauer, M. G., D. H. Johnson, et al. (1998). "The probability of blindness from open-angle glaucoma. [see comments]." *Ophthalmology* 105(11): 2099-104.
Hausler, G., J. M. Herrmann, et al. (1996). "Observation of light propagation in vol. scatterers with 10(11)-fold slow motion." *Optics Letters* 21(14): 1087-1089.
Hazebroek, H. F. and A. A. Holscher (1973). "Interferometric Ellipsometry." *Journal of Physics E-Scientific Instruments* 6(9): 822-826.
Hazebroek, H. F. and W. M. Visser (1983). "Automated Laser Interferometric Ellipsometry and Precision Reflectometry." *Journal of Physics E-Scientific Instruments* 16(7): 654-661.

(56) References Cited

OTHER PUBLICATIONS

He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.

Hee, M. R., J. A. Izatt, et al. (1993). "Femtosecond Transillumination Optical Coherence Tomography." *Optics Letters* 18(12): 950-952.

Hee, M. R., J. A. Izatt, et al. (1995). "Optical coherence tomography of the human retina." *Archives of Ophthalmology* 113(3): 325-32.

Hee, M. R., C. A. Puliafito, et al. (1998). "Topography of diabetic edema with optical macular coherence tomography." *Ophthalmology* 105(2): 360-70.

Hee, M. R., C. A. Puliafito, et al. (1995). "Quantitative assessment of macular edema with optical coherence tomography." *Archives of Ophthalmology* 113(8): 1019-29.

Hellmuth, T. and M. Welle (1998). "Simultaneous measurement of dispersion, spectrum, and distance with a fourier transform spectrometer." *Journal of Biomedical Optics* 3(1): 7-11.

Hemenger, R. P. (1989). "Birefringence of a medium of tenuous parallel cylinders." *Applied Optics* 28(18): 4030-4034.

Henry, M. (1981). "Fresnel-Arago Laws for Interference in Polarized-Light—Demonstration Experiment." *American Journal of Physics* 49(7): 690-691.

Herz, P. R., Y. Chen, et al. (2004). "Micromotor endoscope catheter for in vivo, ultrahigh-resolution optical coherence tomography." *Optics Letters* 29(19): 2261-2263.

Hirakawa, H., H. Iijima, et al. (1999). "Optical coherence tomography of cystoid macular edema associated with retinitis pigmentosa." *American Journal of Ophthalmology* 128(2): 185-91.

Hitzenberger, C. K., A. Baumgartner, et al. (1994). "Interferometric Measurement of Corneal Thickness with Micrometer Precision." *American Journal of Ophthalmology* 118(4): 468-476.

Hitzenberger, C. K., A. Baumgartner, et al. (1999). "Dispersion effects in partial coherence interferometry: Implications for intraocular ranging." *Journal of Biomedical Optics* 4(1): 144-151.

Hitzenberger, C. K., A. Baumgartner, et al. (1998). "Dispersion induced multiple signal peak splitting in partial coherence interferometry." *Optics Communications* 154 (4): 179-185.

Hitzenberger, C. K., M. Danner, et al. (1999). "Measurement of the spatial coherence of superluminescent diodes." *Journal of Modern Optics* 46(12): 1763-1774.

Hitzenberger, C. K. and A. F. Fercher (1999). "Differential phase contrast in optical coherence tomography." *Optics Letters* 24(9): 622-624.

Hitzenberger, C. K., M. Sticker, et al. (2001). "Differential phase measurements in low-coherence interferometry without 2 pi ambiguity." *Optics Letters* 26(23): 1864-1866.

Hoeling, B. M., A. D. Fernandez, et al. (2000). "An optical coherence microscope for 3-dimensional imaging in developmental biology." *Optics Express* 6(7): 136-146.

Hoerauf, H., C. Scholz, et al. (2002). "Transscleral optical coherence tomography: a new imaging method for the anterior segment of the eye." *Archives of Ophthalmology* 120(6): 816-9.

Hoffmann, K. M. Happe, et al. (1998). "Optical coherence tomography (OCT) in dermatology." *Journal of Investigative Dermatology* 110(4): 583-583.

Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.

Hohenleutner, U., M. Hilbert, et al. (1995). "Epidermal Damage and Limited Coagulation Depth with the Flashlamp-Pumped Pulsed Dye-Laser—A Histochemical-Study." *Journal of Investigative Dermatology* 104(5): 798-802.

Holland, A. J. A., H. C. 0. Martin, et al. (2002). "Laser Doppler imaging prediction of burn wound outcome in children." *Burns* 28(1): 11-17.

Hotate, K. and T. Okugawa (1994). "Optical Information-Processing by Synthesis of the Coherence Function." *Journal of Lightwave Technology* 12(7): 1247-1255.

Hourdakis, C. J. and A. Perris (1995). "A Monte-Carlo Estimation of Tissue Optical-Properties for Use in Laser Dosimetry." *Physics in Medicine and Biology* 40(3): 351-364.

Hu, Z., F. Li, et al. (2000). "Wavelength-tunable narrow-linewidth semiconductor fiber-ring laser." *IEEE Photonics Technology Letters* 12(8): 977-979.

Huang, F., W. Yang, et al. (2001). "Quadrature spectral interferometric detection and pulse shaping." *Optics Letters* 26(6): 382-384.

Huang, X. R. and R. W. Knighton (2002). "Linear birefringence of the retinal nerve fiber layer measured in vitro with a multispectral imaging micropolarimeter." *Journal of Biomedical Optics* 7(2): 199-204.

Huber, R., M. Wojtkowski, et al. (2005). "Amplified, frequency swept lasers for frequency domain reflectometry and Oct imaging: design and scaling principles." *Optics Express* 13(9): 3513-3528.

Hunter, D. G., J. C. Sandruck, et al. (1999). "Mathematical modeling of retinal birefringence scanning." *Journal of the Optical Society of America a-Optics Image Science and Vision* 16(9): 2103-2111.

Hurwitz, H. H. and R. C. Jones (1941). "A new calculus for the treatment of optical systems II. Proof of three general equivalence theorems." *Journal of the Optical Society of America* 31(7): 493-499.

Huttner, B., C. De Barros, et al. (1999). "Polarization-induced pulse spreading in birefringent optical fibers with zero differential group delay." *Optics Letters* 24(6): 370-372.

Huttner, B., B. Gisin, et al. (1999). "Distributed Pmd measurement with a polarization-OTDR in optical fibers." *Journal of Lightwave Technology* 17(10): 1843-1848.

Huttner, B., J. Reecht, et al. (1998). "Local birefringence measurements in single-mode fibers with coherent optical frequency-domain reflectometry." *Ieee Photonics Technology Letters* 10(10): 1458-1460.

Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.

Hyde, S. C. W., N. P. Barry, et al. (1995). "Depth-Resolved Holographic Imaging through Scattering Media by Photorefraction." *Optics Letters* 20(11): 1331-1333.

Iftimia, N. V., B. E. Bouma, et al. (2004). "Adaptive ranging for optical coherence tomography." *Optics Express* 12(17): 4025-4034.

Iida, T., N. Hagimura, et al. (2000). "Evaluation of central serous chorioretinopathy with optical coherence tomography." *American Journal of Ophthalmology* 129(1): 16-20.

Imai, M., H. Iijima, et al. (2001). "Optical coherence tomography of tractional macular elevations in eyes with proliferative diabetic retinopathy. [republished in Am J Ophthalmol. Sep. 2001;132(3):458-61 ; 11530091.]." *American Journal of Ophthalmology* 132(1): 81-4.

Indebetouw, G. and P. Klysubun (2000). "Imaging through scattering media with depth resolution by use of low-coherence gating in spatiotemporal digital holography." *Optics Letters* 25(4): 212-214.

Ip, M. S., B. J. Baker, et al. (2002). "Anatomical outcomes of surgery for idiopathic macular hole as determined by optical coherence tomography." *Archives of Ophthalmology* 120(1): 29-35.

Ismail, R., V. Tanner, et al. (2002). "Optical coherence tomography imaging of severe commotio retinae and associated macular hole." *British Journal of Ophthalmology* 86(4): 473-4.

Izatt, J. A., M. R. Hee, et al. (1994). "Optical Coherence Microscopy in Scattering Media." *Optics Letters* 19(8): 590-592.

Izatt, J. A., M. R. Hee, et al. (1994). "Micrometer-scale resolution imaging of the anterior eye in vivo with optical coherence tomography." *Archives of Ophthalmology* 112 (12): 1584-9.

Izatt, J. A., M. D. Kulkami, et al. (1997). "in vivo bidirectional color Doppler flow imaging of picoliter blood volumes using optical coherence tomography." *Optics Letters* 22(18): 1439-1441.

Izatt, J. A., M. D. Kulkarni, et al. (1996). "Optical coherence tomography and microscopy in gastrointestinal tissues." *IEEE Journal of Selected Topics in Quantum Electronics* 2(4): 1017.

Jacques, S. L., J. S. Nelson, et al. (1993). "Pulsed Photothermal Radiometry of Port-Wine-Stain Lesions." *Applied Optics* 32(13): 2439-2446.

(56) References Cited

OTHER PUBLICATIONS

Jacques, S. L., J. R. Roman, et al. (2000). "Imaging superficial tissues with polarized light." *Lasers In Surgery and Medicine* 26(2): 119-129.

Jang, I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.

Jang, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl. S,.

Jang, I. K., G. J. Tearney, et al. (2000). "Comparison of optical coherence tomography and intravascular ultrasound for detection of coronary plaques with large lipid-core in living patients." *Circulation* 102(18): 509-509.

Jeng, J. C., A. Bridgeman, et al. (2003). "Laser Doppler imaging determines need for excision and grafting in advance of clinical judgment: a prospective blinded trial." *Burns* 29(7): 665-670.

Jesser, C. A., S. A. Boppart, et al. (1999). "High resolution imaging of transitional cell carcinoma with optical coherence tomography: feasibility for the evaluation of bladder pathology." *British Journal of Radiology* 72: 1170-1176.

Johnson, C. A., J. L. Keltner, et al. (2002). "Baseline visual field characteristics in the ocular hypertension treatment study." *Ophthalmology* 109(3): 432-7.

Jones, R. C. (1941). "A new calculus for the treatment of optical systems III. The Sohncke theory of optical activity." *Journal of the Optical Society of America* 31 (7): 500-503.

Jones, R. C. (1941). "A new calculus for the treatment of optical systems I. Description and discussion of the calculus." *Journal of the Optical Society of America* 31(7): 488-493.

Jones, R. C. (1942). "A new calculus for the treatment of optical systems. IV." *ournal of the Optical Society of America* 32(8): 486-493.

Jones, R. C. (1947). "A New Calculus for the Treatment of Optical Systems .6. Experimental Determination of the Matrix." *Journal of the Optical Society of America* 37(2): 110-112.

Jones, R. C. (1947). "A New Calculus for the Treatment of Optical Systems .5. A More General Formulation, and Description of Another Calculus." *Journal of the Optical Society of America* 37(2): 107-110.

Jones, R. C. (1948). "A New Calculus for the Treatment of Optical Systems .7. Properties of the N-Matrices." *Journal of the Optical Society of America* 38(8): 671-685.

Jones, R. C. (1956). "New Calculus for the Treatment of Optical Systems .8. Electromagnetic Theory." *Journal of the Optical Society of America* 46(2): 126-131.

Jopson, R. MThe ., L. E. Nelson, et al. (1999). "Measurement of second-order polarization-mode dispersion vectors in optical fibers." *Ieee Photonics Technology Letters* 11 (9): 1153-1155.

Jost, B. M., A. V. Sergienko, et al. (1998). "Spatial correlations of spontaneously down-converted photon pairs detected with a single-photon-sensitive CCD camera." *Optics Express* 3(2): 81-88.

Kaplan, B., E. Compain, et al. (2000). "Phase-modulated Mueller ellipsometry characterization of scattering by latex sphere suspensions." *Applied Optics* 39 (4): 629-636.

Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.

Kasuga, Y., J. Arai, et al. (2000). "Optical coherence tomograhy to confirm early closure of macular holes." *American Journal of Ophthalmology* 130(5): 675-6.

Kaufman, T., S. N. Lusthaus, et al. (1990). "Deep Partial Skin Thickness Burns—a Reproducible Animal-Model to Study Burn Wound-Healing." *Burns* 16(1): 13-16.

Kemp, N. J., J. Park, et al. (2005). "High-sensitivity determination of birefringence in turbid media with enhanced polarization-sensitive optical coherence tomography." *Journal of the Optical Society of America a-Optics Image Science and Vision* 22(3): 552-560.

Kerrigan-Baumrind, L. A., H. A. Quigley, et al. (2000). "Number of ganglion cells in glaucoma eyes compared with threshold visual field tests in the same persons." *Investigative Ophthalmology & Visual Science* 41(3): 741-8.

Kesen, M. R., G. L. Spaeth, et al. (2002). "The Heidelberg Retina Tomograph vs clinical impression in the diagnosis of glaucoma." *American Journal of Ophthalmology* 133(5): 613-6.

Kienle, A. and R. Hibst (1995). "A New Optimal Wavelength for Treatment of Port-Wine Stains." *Physics in Medicine and Biology* 40(10): 1559-1576.

Kienle, A., L. Lilge, et al. (1996). "Spatially resolved absolute diffuse reflectance measurements for noninvasive determination of the optical scattering and absorption coefficients of biological tissue." *Applied Optics* 35(13): 2304-2314.

Kim, B. Y. and S. S. Choi (1981). "Analysis and Measurement of Birefringence in Single-Mode Fibers Using the Backscattering Method." *Optics Letters* 6(11): 578-580.

Kimel, S., L. O. Svaasand, et al. (1994). "Differential Vascular-Response to Laser Photothermolysis." *Journal of Investigative Dermatology* 103(5): 693-700.

Kloppenberg, F. W. H., G. Beerthuizen, et al. (2001). "Perfusion of burn wounds assessed by Laser and Doppler Imaging is related to burn depth healing time." *Burns* 27(4): 359-363.

Knighton, R. W. and X. R. Huang (2002). "Analytical methods for scanning laser polarimetry." *Optics Express* 10(21): 1179-1189.

Knighton, R. W., X. R. Huang, et al. (2002). "Analytical model of scanning laser polarimetry for retinal nerve fiber layer assessment." *Investigative Ophthalmology & Visual Science* 43(2): 383-392.

Knuettel, A. R. S., Joseph M.: Shay, M.; Knutson, Jay R. (1994). "Stationary low-coherence light imaging and spectroscopy using a CCD camera." *Proc. SPIE*, vol. 2135: p. 239-250.

Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.

Knuttel, A. and J. M. Schmitt (1993). "Stationary Depth-Profiling Reflectometer Based on Low-Coherence Interferometry." *Optics Communications* 102(3-4): 193-198.

Knuttel, A., J. M. Schmitt, et al. (1994). "Low-Coherence Reflectometry for Stationary Lateral and Depth Profiling with Acoustooptic Deflectors and a CCD Camera." *Optics Letters* 19(4): 302-304.

Kobayashi, M., H. Hanafusa, et al. (1991). "Polarization-Independent Interferometric Optical-Time-Domain Reflectometer." *Journal of Lightwave Technology* 9(5): 623-628.

Kolios, M. C., M. D. Sherar, et al. (1995). "Large Blood-Vessel Cooling in Heated Tissues—A Numerical Study." *Physics in Medicine and Biology* 40(4): 477-494.

Koozekanani, D., K. Boyer, et al. (2001). "Retinal thickness measurements from optical coherence tomography using a Markov boundary model." *Ieee Transactions on Medical Imaging* 20(9): 900-916.

Kop, R. H. J. and R. Sprik (1995). "Phase-sensitive interferometry with ultrashort optical pulses." *Review of Scientific Instruments* 66(12): 5459-5463.

Kramer, R. Z., J. Bella, et al. (1999). "Sequence dependent conformational variations of collagen triple-helical structure." *Nature Structural Biology* 6(5): 454-7.

Kulkarni, M. D., T. G. van Leeuwen, et al. (1998). "Velocity-estimation accuracy and frame-rate limitations in color Doppler optical coherence tomography." *Optics Letters* 23(13): 1057-1059.

Kwon, Y. H., C. S. Kim, et al. (2001). "Rate of visual field loss and long-term visual outcome in primary open-angle glaucoma." *American Journal of Ophthalmology* 132(1): 47-56.

Kwong, K. F., D. Yankelevich, et al. (1993). "400-Hz Mechanical Scanning Optical Delay-Line." *Optics Letters* 18(7): 558-560.

Landers, J., I. Goldberg, et al. (2002). "Analysis of risk factors that may be associated with progression from ocular hypertension to primary open angle glaucoma." *Clin Experiment Ophthalmogy* 30(4): 242-7.

(56) References Cited

OTHER PUBLICATIONS

Laszlo, A. and A. Venetianer (1998). Heat resistance in mammalian cells: Lessons and challenges. *Stress of Life*. 851: 169-178.

Laszlo, A. and A. Venetianer (1998). "Heat resistance in mammalian cells: lessons and challenges. [Review] [52 refs]." *Annals of the New York Academy of Sciences* 851: 169-78.

Laufer, J., R. Simpson, et al. (1998). "Effect of temperature on the optical properties of ex vivo human dermis and subdermis." *Physics in Medicine and Biology* 43(9): 2479-2489.

Lederer, D. E., J. S. Schuman, et al. (2003). "Analysis of macular volume in normal and glaucomatous eyes using optical coherence tomography." *American Journal of Ophthalmology* 135(6): 838-843.

Lee, P. P., Z. W. Feldman, et al. (2003). "Longitudinal prevalence of major eye diseases." *Archives of Ophthalmology* 121(9): 1303-1310.

Lehrer, M. S., T. T. Sun, et al. (1998). "Strategies of epithelial repair: modulation of stem cell and transit amplifying cell proliferation." *Journal of Cell Science* 111(Pt 19): 2867-75.

Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.

Leitgeb, R., C. K. Hitzenberger, et al. (2003). "Performance of fourier domain vs. time domain optical coherence tomography." *Optics Express* 11(8): 889-894.

Leitgeb, R., L. F. Schmetterer, et al. (2002). "Flow velocity measurements by frequency domain short coherence interferometry." *Proc. SPIE* 4619: 16-21.

Leitgeb, R. A., W. Drexler, et al. (2004). "Ultrahigh resolution Fourier domain optical coherence tomography." *Optics Express* 12(10): 2156-2165.

Leitgeb, R. A., C. K. Hitzenberger, et al. (2003). "Phase-shifting algorithm to achieve high-speed long-depth-range probing by frequency-domain optical coherence tomography." *Optics Letters* 28(22): 2201-2203.

Leitgeb, R. A., L. Schmetterer, et al. (2003). "Real-time assessment of retinal blood flow with ultrafast acquisition by color Doppler Fourier domain optical coherence tomography." *Optics Express* 11(23): 3116-3121.

Leitgeb, R. A., L. Schmetterer, et al. (2004). "Real-time measurement of in vitro flow by Fourier-domain color Doppler optical coherence tomography." *Optics Letters* 29 (2): 171-173.

LeRoyBrehonnet, F. and B. LeJeune (1997). "Utilization of Mueller matrix formalism to obtain optical targets depolarization and polarization properties." *Progress in Quantum Electronics* 21(2): 109-151.

Leske, M. C., A. M. Connell, et al. (1995). "Risk factors for open-angle glaucoma. The Barbados Eye Study. [see comments]." *Archives of Ophthalmology* 113(7): 918-24.

Leske, M. C., A. M. Connell, et al. (2001). "Incidence of open-angle glaucoma: the Barbados Eye Studies. The Barbados Eye Studies Group. [see comments]." *Archives of Ophthalmology* 119(1): 89-95.

Leske, M. C., A. Heijl, et al. (1999). "Early Manifest Glaucoma Trial. Design and Baseline Data." *Ophthalmology* 106(11): 2144-2153.

Lewis, S. E., J. R. DeBoer, et al. (2005). "Sensitive, selective, and analytical improvements to a porous silicon gas sensor." *Sensors and Actuators B: Chemical* 110(1): 54-65.

Lexer, F., C. K. Hitzenberger, et al. (1999). "Dynamic coherent focus OCT with depth- independent transversal resolution." *Journal of Modern Optics* 46(3): 541-553.

Li, X., C. Chudoba, et al. (2000). "Imaging needle for optical coherence tomography." *Optics Letters* 25: 1520-1522.

Li, X., T. H. Ko, et al. (2001). "Intraluminal fiber-optic Doppler imaging catheter for structural and functional optical coherence tomography." *Optics Letters* 26: 1906-1908.

Liddington, M. I. and P. G. Shakespeare (1996). "Timing of the thermographic assessment of burns." *Burns* 22(1): 26-8.

Lindmo, T., D. J. Smithies, et al. (1998). "Accuracy and noise in optical Doppler tomography studied by Monte Carlo simulation." *Physics in Medicine and Biology* 43(10): 3045-3064.

Liu, J., X. Chen, et al. (1999). "New thermal wave aspects on burn evaluation of skin subjected to instantaneous heating." *IEEE Transactions on Biomedical Engineering* 46(4): 420-8.

Luke, D. G., R. McBride, et al. (1995). "Polarization mode dispersion minimization in fiber-wound piezoelectric cylinders." *Optics Letters* 20(24): 2550-2552.

MacNeill, B. D., I. K. Jang, et al, (2004). "Focal and multi-focal plaque distributions in patients with macrophage acute and stable presentations of coronary artery disease." *Journal of the American College of Cardiology* 44(5): 972-979.

Mahgerefteh, D. and C. R. Menyuk (1999). "Effect of first-order PMD compensation on the statistics of pulse broadening in a fiber with randomly varying birefringence." *Ieee Photonics Technology Letters* 11(3): 340-342.

Maitland, D. J. and J. T. Walsh, Jr. (1997). "Quantitative measurements of linear birefringence during heating of native collagen." *Lasers in Surgery & Medicine* 20 (3): 310-8.

Majaron, B., S. M. Srinivas, et al. (2000). "Deep coagulation of dermal collagen with repetitive Er : YAG laser irradiation." *Lasers in Surgery and Medicine* 26(2): 215-222.

Mansuripur, M. (1991). "Effects of High-Numerical-Aperture Focusing on the State of Polarization in Optical and Magnetooptic Data-Storage Systems." *Applied Optics* 30(22): 3154-3162.

Marshall, G. W., S. J. Marshall, et al. (1997). "The dentin substrate: structure and properties related to bonding." *Journal of Dentistry* 25(6): 441-458.

Martin, P. (1997). "Wound healing—Aiming for perfect skin regeneration." *Science* 276 (5309): 75-81.

Martinez, O. E. (1987). "3000 Times Grating Compressor with Positive Group-Velocity Dispersion—Application to Fiber Compensation in 1.3-1.6 Mu-M Region." *Ieee Journal of Quantum Electronics* 23(1): 59-64.

Martinez, O. E., J. P. Gordon, et al. (1984). "Negative Group-Velocity Dispersion Using Refraction." *Journal of the Optical Society of America a-Optics Image Science and Vision* 1(10): 1003-1006.

McKinney, J. D., M. A. Webster, et al. (2000). "Characterization and imaging in optically scattering media by use of laser speckle and a variable-coherence source." *Optics Letters* 25(1): 4-6.

Miglior, S., M. Casula, et al. (2001). "Clinical ability of Heidelberg retinal tomograph examination to detect glaucomatous visual field changes." *Ophthalmology* 108 (9): 1621-7.

Milner, T. E., D. M. Goodman, et al. (1996). "Imaging laser heated subsurface chromophores in biological materials: Determination of lateral physical dimensions." *Physics in Medicine and Biology* 41(1): 31-44.

Milner, T. E., D. M. Goodman, et al. (1995). "Depth Profiling of Laser-Heated Chromophores in Biological Tissues by Pulsed Photothermal Radiometry." *Journal of the Optical Society of America a-Optics Image Science and Vision* 12 (7): 1479-1488.

Milner, T. E., D. J. Smithies, et al. (1996). "Depth determination of chromophores in human skin by pulsed photothermal radiometry." *Applied Optics* 35(19): 3379-3385.

Mishchenko, M. I. and J. W. Hovenier (1995). "Depolarization of Light Backscattered by Randomly Oriented Nonspherical Particles." *Optics Letters* 20(12): 1356-&.

Mistlberger, A., J. M. Liebmann, et al. (1999). "Heidelberg retina tomography and optical coherence tomography in normal, ocular-hypertensive, and glaucomatous eyes." *Ophthalmology* 106(10): 2027-32.

Mitsui, T. (1999). "High-speed detection of ballistic photons propagating through suspensions using spectral interferometry." *Japanese Journal of Applied Physics* Part 1-Regular Papers Short Notes & Review Papers 38(5A): 2978-2982.

Molteno, A. C., N. J. Bosma, et al. (1999). "Otago glaucoma surgery outcome study: long-term results of trabeculectomy—1976 to 1995." *Ophthalmology* 106(9): 1742-50.

Morgner, U., W. Drexler, et al. (2000). "Spectroscopic optical coherence tomography." *Optics Letters* 25(2): 111-113.

Morgner, U., F. X. Kartner, et al. (1999). "Sub-two-cycle pulses from a Kerr-lens mode-locked Ti : sapphire laser (vol. 24, p. 411, 1999)." *Optics Letters* 24(13): 920-920.

(56) References Cited

OTHER PUBLICATIONS

Mourant, J. R., A. H. Hielscher, et al. (1998). "Evidence of intrinsic differences in the light scattering properties of tumorigenic and nontumorigenic cells." *Cancer Cytopathology* 84(6): 366-374.
Muller, M., J. Squier, et al. (1998). "Dispersion pre-compensation of 15 femtosecond optical pulses for high-numerical-aperture objectives." *Journal of Microscopy-Oxford* 191: 141-150.
Muscat, S., N. McKay, et al. (2002). "Repeatability and reproducibility of corneal thickness measurements by optical coherence tomography." *Investigative Ophthalmology & Visual Science* 43(6): 1791-5.
Musch, D. C., P. R. Lichter, et al. (1999). "The Collaborative Initial Glaucoma Treatment Study. Study Design, MethodsR, and Baseline Characteristics of Enrolled Patients." *Ophthalmology* 106: 653-662.
Neerken, S., Lucassen, G.W., Bisschop, M.A., Lenderink, E., Nuijs, T.A.M. (2004). "Characterization of age-related effects In human skin: A comparative study that applies confocal laser scanning microscopy and optical coherence tomography." *Journal of Biomedical Optics* 9(2): 274-281.
Nelson, J. S., K. M. Kelly, et al. (2001). "Imaging blood flow in human port-wine stain in situ and in real time using optical Doppler tomography." *Archives of Dermatology* 137(6): 741-744.
Newson, T. P., F. Farahi, et al. (1988). "Combined Interferometric and Polarimetric Fiber Optic Temperature Sensor with a Short Coherence Length Source." *Optics Communications* 68(3): 161-165.
Nov., L. J. (1993). "Recovery of the Matrix Operators in the Similarity and Congruency Transformations—Applications in Polarimetry." *Journal of the Optical Society of America a-Optics Image Science and Vision* 10(4): 719-739.
Oh, W. Y., S. H. Yun, et al. (2005). "Wide tuning range wavelength-swept laser with two semiconductor optical amplifiers." *Ieee Photonics Technology Letters* 17(3): 678- 680.
Oka, K. and T. Kato (1999). "Spectroscopic polarimetry with a channeled spectrum." *Optics Letters* 24(21): 1475-1477.
Okugawa, T. and K. Rotate (1996). "Real-time optical image processing by synthesis of the coherence function using real-time holography." *Ieee Photonics Technology Letters* 8(2): 257-259.
Oshima, M., R. Torii, et al. (2001). "Finite element simulation of blood flow in the cerebral artery." *Computer Methods in Applied Mechanics and Engineering* 191 (6-7): 661-671.
Pan, Y. T., H. K. Xie, et al. (2001). "Endoscopic optical coherence tomography based on a microelectromechanical mirror." *Optics Letters* 26(24): 1966-1968.
Parisi, V., G. Manni, et al. (2001). "Correlation between optical coherence tomography, pattern electroretinogram, and visual evoked potentials in open-angle glaucoma patients." *Ophthalmology* 108(5): 905-12.
Park, B. H., M. C. Pierce, et al. (2005). "Real-time fiber-based multifunctional spectral-domain optical coherence tomography at 1.3 mu m." *Optics Express* 13(11): 3931-3944.
Park, D. H., J. W. Hwang, et al. (1998). "Use of laser Doppler flowmetry for estimation of the depth of burns." *Plastic and Reconstructive Surgery* 101(6): 1516-1523.
Pendry, J. B., A. J. Holden, et al. (1999). "Magnetism from conductors and enhanced nonlinear phenomena." *Ieee Transactions on Microwave Theory and Techniques* 47(11): 2075-2084.
Penninckx, D. and V. Morenas (1999). "Jones matrix of polarization mode dispersion." *Optics Letters* 24(13): 875-877.
Pierce, M. C., M. Shishkov, et al. (2005). "Effects of sample arm motion in endoscopic polarization-sensitive optical coherence tomography." *Optics Express* 13(15): 5739-5749.
Pircher, M., E. Gotzinger, et al. (2003). "Measurement and imaging of water concentration in human cornea with differential absorption optical coherence tomography." *Optics Express* 11(18): 2190-2197.
Pircher, M., E. Gotzinger, et al. (2003). "Speckle reduction in optical coherence tomography by frequency compounding." *Journal of Biomedical Optics* 8(3): 565-569.
Podoleanu, A. G., G. M. Dobre, et al. (1998). "En-face coherence imaging using galvanometer scanner modulation." *Optics Letters* 23(3): 147-149.
Podoleanu, A. G. and D. A. Jackson (1999). "Noise analysis of a combined optical coherence tomograph and a confocal scanning ophthalmoscope." *Applied Optics* 38(10): 2116-2127.
Podoleanu, A. G., J. A. Rogers, et al. (2000). "Three dimensional OCT images from retina and skin." *Optics Express* 7(9): 292-298.
Podoleanu, A. G., M. Seeger, et al. (1998). "Transversal and longitudinal images from the retina of the living eye using low coherence reflectometry." *Journal of Biomedical Optics* 3(1): 12-20.
Poole, C. D. (1988). "Statistical Treatment of Polarization Dispersion in Single-Mode Fiber." *Optics Letters* 13(8): 687-689.
Povazay, B., K. Bizheva, et al. (2002). "Submicrometer axial resolution optical coherence tomography." *Optics Letters* 27(20): 1800-1802.
Qi, B., A. P. Himmer, et al. (2004). "Dynamic focus control in high-speed optical coherence tomography based on a microelectromechanical mirror." *Optics Communications* 232(1-6): 123-128.
Radhakrishnan, S., A. M. Rollins, et al. (2001). "Real-time optical coherence tomography of the anterior segment at 1310 nm." *Archives of Ophthalmology* 119(8): 1179-1185.
Rogers, A. J. (1981). "Polarization-Optical Time Domain Reflectometry—a Technique for the Measurement of Field Distributions." Applied Optics 20(6): 1060-1074.
Rollins, A. M. and J. A. Izatt (1999). "Optimal interferometer designs for optical coherence tomography." *Optics Letters* 24(21): 1484-1486.
Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.
Rollins, A. M., S. Yazdanfar, et al. (2002). "Real-time in vivo colors Doppler optical coherence tomography." *Journal of Biomedical Optics* 7(1): 123-129.
Rollins, A. M., S. Yazdanfar, et al. (2000). "Imaging of human retinal hemodynamics using color Doppler optical coherence tomography." *Investigative Ophthalmology & Visual Science* 41(4): S548-S548.
Sandoz, P. (1997). "Wavelet transform as a processing tool in white-light interferometry." *Optics Letters* 22(14): 1065-1067.
Sankaran, V., M. J. Everett, et al. (1999). "Comparison of polarized-light propagation in biological tissue and phantoms." *Optics Letters* 24(15): 1044-1046.
Sankaran, V., J. T. Walsh, et al. (2000). "Polarized light propagation through tissue phanto, ehms containing densely packed scatterers." *Optics Letters* 25(4): 239-241.
Sarunic, M. V., M. A. Choma, et al. (2005). "Instantaneous complex conjugate resolved spectral domain and swept-source Oct using 3×x3 fiber couplers." *Optics Express* 13(3): 957-967.
Sathyam, U. S., B. W. Colston, et al. (1999). "Evaluation of optical coherence quantitation of analytes in turbid media by use of two wavelengths." *Applied Optics* 38(10): 2097-2104.
Schmitt, J. M. (1997). "Array detection for speckle reduction in optical coherence microscopy." *Physics in Medicine and Biology* 42(7): 1427-1439.
Schmitt, J. M. (1999). "Optical coherence tomography (OCT): A review." *Ieee Journal of Selected Topics in Quantum Electronics* 5(4): 1205-1215.
Schmitt, J. M. and A. Knuttel (1997). "Model of optical coherence tomography of heterogeneous tissue." *Journal of the Optical Society of America a-Optics Image Science and Vision* 14(6): 1231-1242.
Schmitt, J. M., S. L. Lee, et al. (1997). "An optical coherence microscope with enhanced resolving power in thick tissue." *Optics Communications* 142(4-6): 203-207.
Schmitt, J. M., S. H. Xiang, et al. (1998). "Differential absorption imaging with optical coherence tomography." *Journal of the Optical Society of America a-Optics Image Science and Vision* 15(9): 2288-2296.
Schmitt, J. M., S. H. Xiang, et al. (1999). "Speckle in optical coherence tomography." *Journal of.Biomedical Optics* 4(1): 95-105.
Schmitt, J. M., M. J. Yadlowsky, et al. (1995). "Subsurface Imaging of Living Skin with Optical Coherence Microscopy." *Dermatology* 191(2): 93-98.

(56) References Cited

OTHER PUBLICATIONS

Shi, H., J. Finlay, et al. (1997). "Multiwavelength 10-GHz picosecond pulse generation from a single-stripe semiconductor diode laser." *Ieee Photonics Technology Letters* 9(11): 1439-1441.

Shi, H., I. Nitta, et al. (1999). "Demonstration of phase correlation in multiwavelength mode-locked semiconductor diode lasers." *Optics Letters* 24(4): 238-240.

Simon, R. (1982). "The Connection between Mueller and Jones Matrices of Polarization Optics." *Optics Communications* 42(5): 293-297.

Smith, P. J. M., (2000) "Variable-Focus Microlenses as a Potential Technology for Endoscopy." SPIE (vol. 3919), USA pp. 187-192.

Smithies, D. J., T. Lindmo, et al. (1998). "Signal attenuation and localization in optical coherence tomography studied by Monte Carlo simulation." *Physics in Medicine and Biology* 43(10): 3025-3044.

Sorin, W. V. and D. F. Gray (1992). "Simultaneous Thickness and Group Index Measurement Using Optical Low-Coherence Reflectometry." *Ieee Photonics Technology Letters* 4(1): 105-107.

Sticker, M., C. K. Hitzenberger, et al. (2001). "Quantitative differential phase measurement and imaging in transparent and turbid media by optical coherence tomography." *Optics Lettes* 26(8): 518-520.

Sticker, M., M. Pircher, et al. (2002). "En face imaging of single cell layers by differential phase-contrast optical coherence microscopy." *Optics Letters* 27(13): 1126-1128.

Stoller, P., B. M. Kim, et al. (2002). "Polarization-dependent optical second-harmonic imaging of a rat-tail tendon." *Journal of Biomedical Optics* 7(2): 205-214.

Sun, C. S. (2003). "Multiplexing of fiber-optic acoustic sensors in a Michelson interferometer configuration." *Optics Letters* 28(12): 1001-1003.

Swanson, E. A., J. A. Izatt, et al. (1993). "In-Vivo Retinal Imaging by Optical Coherence Tomography." *Optics Letters* 18(21): 1864-1866.

Takada, K., A. Himeno, et al. (1991). "Phase-Noise and Shot-Noise Limited Operations of Low Coherence Optical-Time Domain reflectometry." *Applied Physics Letters* 59(20): 2483-2485.

Takenaka, H. (1973). "Unified Formalism for Polarization Optics by Using Group-Theory I (Theory)." *Japanese Journal of Applied Physics* 12(2): 226-231.

Tanno, N., T. Ichimura, et al. (1994). "Optical Multimode Frequency-Domain Reflectometer." *Optics Letters* 19(8): 587-589.

Tan-no, N., T. Ichimura, et al. (1994). "Optical Multimode Frequency-Domain Reflectometer." *Optics Letters* 19(8): 587-589.

Targowski, P., M. Wojtkowski, et al. (2004). "Complex spectral OCT in human eye imaging in vivo." *Optics Communications* 229(1-6): 79-84.

Tearney, G. J., S. A. Boppart, et al. (1996). "Scanning single-mode fiber optic catheter- endoscope for optical coherence tomography (vol. 21, pg. 543, 1996)." *Optics Letters* 21(12): 912-912.

Tearney, G. J., B. E. Bouma, et al. (1996). "Rapid acquisition of in vivo biological images by use of optical coherence tomography." *Optics Letters* 21(17): 1408-1410.

Tearney, G. J., B. E. Bouma, et al. (1997). "In vivo endoscopic optical biopsy with optical coherence tomography." *Science* 276(5321): 2037-2039.

Tearney, G. J., M. E. Brezinski, et al. (1996). "Catheter-based optical imaging of a human coronary artery." *Circulation* 94(11): 3013-3013.

Tearney, G. J., M. E. Brezinski, et al. (1997). "In vivo endoscopic optical biopsy with optical coherence tomography." *Science* 276(5321): 2037-9.

Tearney, G. J., M. E. Brezinski, et al. (1997). "Optical biopsy in human gastrointestinal tissue using optical coherence tomography." *American Journal of Gastroenterology* .92(10): 1800-1804.

Tearney, G. J., M. E. Brezinski, et al. (1995). "Determination of the refractive index of highly scattering human tissue by optical coherence tomography." *Optics Letters* 20(21): 2258-2260.

Tearney, G. J., I. K. Jong, et al. (2000). "Porcine coronary imaging in vivo by optical coherence tomography." *Acta Cardiologica* 55(4): 233-237.

Tearney, G. J., R. H. Webb, et al. (1998). "Spectrally encoded confocal microscopy." *Optics Letters* 23(15): 1152-1154.

Tearney, G. J., H. Yabushita, et al. (2003). "Quantification of macrophage content in atherosclerotic plaques by optical coherence tomography." *Circulation* 107(1): 113-119.

Tower, T. T. and R. T. Tranquillo (2001). "Alignment maps of tissues: I. Microscopic elliptical polarimetry." *Biophysical Journal* 81(5): 2954-2963.

Tower, T. T. and R. T. Tranquillo (2001). "Alignment maps of tissues: II. Fast harmonic analysis for imaging." *Biophysical Journal* 81(5): 2964-2971.

Troy, T. L. and S. N. Thennadil (2001). "Optical properties of human skin in the near infrared wavelength range of 1000 to 2200 nm." *Journal of Biomedical Optics* 6 (2): 167-176.

Vabre, L., A. Dubois, et al. (2002). "Thermal-light full-field optical coherence tomography." *Optics Letters* 27(7): 530-532.

Vakhtin, A. B., D. J. Kane, et al. (2003). "Common-path interferometer for frequency-domain optical coherence tomography." *Applied Optics* 42(34): 6953-6958.

Vakhtin, A. B., K. A. Peterson, et al. (2003). "Differential spectral interferometry: an imaging technique for biomedical applications." *Optics Letters* 28(15): 1332-1334.

Vakoc, B. J., S. H. Yun, et al. (2005). "Phase-resolved optical frequency domain imaging." *Optics Express* 13(14): 5483-5493.

van Leeuwen, T. G., M. D. Kulkarni, et al. (1999). "High-flow-velocity and shear-rate imaging by use of color Doppler optical coherence tomography." *Optics Letters* 24(22): 1584-1586.

Vansteenkiste, N., P. Vignolo, et al. (1993). "Optical Reversibility Theorems for Polarization—Application to Remote-Control of Polarization." *Journal of the Optical Society of America a-Optics Image Science and Vision* 10(10): 2240-2245.

Vargas, O., E. K. Chan, et al. (1999). "Use of an agent to reduce scattering in skin." *Lasers in Surgery and Medicine* 24(2): 133-141.

Wang, R. K. (1999). "Resolution improved optical coherence-gated tomography for imaging through biological tissues." *Journal of Modern Optics* 46(13): 1905-1912.

Wang, X. J., T. E. Milner, et al. (1997). "Measurement of fluid-flow velocity profile in turbid media by the use of optical Doppler tomography." *Applied Optics* 36(1): 144-149.

Wang, X. J., T. E. Milner, et al. (1995). "Characterization of Fluid-Flow Velocity by Optical Doppler Tomography." *Optics Letters* 20(11): 1337-1339.

Wang, Y. M., J. S. Nelson, et al. (2003). "Optimal wavelength for ultrahigh-resolution optical coherence tomography." *Optics Express* 11(12): 1411-1417.

Wang, Y. M., Y. H. Zhao, et al. (2003). "Ultrahigh-resolution optical coherence tomography by broadband continuum generation from a photonic crystal fiber." *Optics Letters* 28(3): 182-184.

Watkins, L. R., S. M. Tan, et al. (1999). "Determination of interferometer phase distributions by use of wavelets." *Optics Letters* 24(13): 905-907.

Wetzel, J. (2001). "Optical coherence tomography in dermatology: a review." *Skin Research and Technology* 7(1): 1-9.

Wentworth, R. H. (1989). "Theoretical Noise Performance of Coherence-Multiplexed Interferometric Sensors." *Journal of Lightwave Technology* 7(6): 941-956.

Westphal, V., A. M. Rollins, et al. (2002). "Correction of geometric and refractive image distortions in optical coherence tomography applying Fermat's principle." *Optics Express* 10(9): 397-404.

Westphal, V., S. Yazdanfar, et al. (2002). "Real-time, high velocity-resolution color Doppler optical coherence tomography." *Optics Letters* 27(1): 34-36.

Williams, P. A. (1999). "Rotating-wave-plate Stokes polarimeter for differential group delay measurements of polarization-mode dispersion." *Applied Optics* 38(31): 6508-6515.

Wojtkowski, M., T. Bajraszewski, et al. (2003). "Real-time in vivo imaging by high-speed spectral optical coherence tomography." *Optics Letters* 28(19): 1745-1747.

Wojtkowski, M., A. Kowalczyk, et al. (2002). "Full range complex spectral optical coherence tomography technique in eye imaging." *Optics Letters* 27(16): 1415-1417.

(56) References Cited

OTHER PUBLICATIONS

Wojtkowski, M., R. Leitgeb, et al. (2002). "In vivo human retinal imaging by Fourier domain optical coherence tomography." *Journal of Biomedical Optics* 7(3): 457-463.
Wojtkowski, M., R. Leitgeb, et al. (2002). "Fourier domain OCT imaging of the human eye in vivo." *Proc. SPIE* 4619: 230-236.
Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.
Wong, B. J. F., Y. H. Zhao, et al. (2004). "Imaging the internal structure of the rat cochlea using optical coherence tomography at 0.827 mu m and 1.3 mum." *Otolaryngology-Head and Neck Surgery* 130(3): 334-338.
Yabushita, H. B., et al. (2002) "Measurement of Thin Fibrous Caps in Atherosclerotic Plaques by Optical Coherence Tomography." American Heart Association, Inc, Circulation 2002;106;1640.
Yang, C., A. Wax, et al. (2001). "Phase-dispersion 688. optical tomography." *Optics Letters* 26(10): 686-688.
Yang, C., A. Wax, et al. (2001). "Phase-referenced sensitivity applied to the study of cell interferometer with subwavelength and subhertz membrane dynamics." *Optics Letters* 26(16): 1271-1273.
Yang, C. H., A. Wax, et al. (2001). "Phase-dispersion optical tomography." *Optics Letters* 26(10): 686-688.
Yang, C. H., A. Wax, et al. (2000). "Interferometric phase-dispersion microscopy." *Optics Letters* 25(20): 1526-1528.
Yang, V. X. D., M. L. Gordon, et al. (2002). "Improved phase-resolved optical Doppler tomography using the Kasai velocity estimator and histogram segmentation." *Optics Communications* 208(4-6): 209-214.
Yang, V. X. D., M. L. Gordon, et al. (2003). "High speed, wide velocity dynamic range Doppler optical coherence tomography (Part I): System design, signal processing, and performance." *Optics Express* 11(7): 794-809.
Yang, V. X. D., M. L. Gordon, et al. (2003). "High speed, wide velocity dynamic range Doppler optical coherence tomography (Part II): Imaging in vivo cardiac dynamics of Xenopus laevis." *Optics Express* 11(14): 1650-1658.
Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.
Yang, V. X. D., B. Qi, et al. (2003). "In vivo feasibility of endoscopic catheter-based Doppler optical coherence tomography." *Gastroenterology* 124(4): A49-A50.
Yao, G. and L. H. V. Wang (2000). "Theoretical and experimental studies of ultrasound-modulated optical tomography in biological tissue." *Applied Optics* 39(4): 659-664.
Yazdanfar, S. and J. A. Izatt (2002). "Self-referenced Doppler optical coherence tomography." *Optics Letters* 27(23): 2085-2087.
Yazdanfar, S., M. D. Kulkarni, et al. (1997). "High resolution imaging of in vivo cardiac dynamics using color Doppler optical coherence tomography." *Optics Express* 1 (13) : 424-431.
Yazdanfar, S., A. M. Rollins, et al. (2000). "Imaging and velocimetry of the human retinal circulation with color Doppler optical coherence tomography." *Optics Letters* 25(19): 1448-1450.
Yazdanfar, S., A. M. Rollins, et al. (2000). "Noninvasive imaging and velocimetry of human retinal blood flow using color Doppler optical coherence tomography." *Investigative Ophthalmology & Visual Science* 41(4): S548-S548.
Yazdanfar, S., A. M. Rollins, et al. (2003). "In vivo imaging of human retinal flow dynamics by color Doppler optical coherence tomography." *Archives of Ophthalmology* 121(2): 235-239.
Yazdanfar, S., C. H. Yang, et al. (2005). "Frequency estimation precision in Doppler optical coherence tomography using the Cramer-Rao lower bound." *Optics Express* 13(2): 410-416.
Yun, S. H., C. Boudoux, et al. (2004). "Extended-cavity semiconductor wavelength- swept laser for biomedical imaging." *Ieee Photonics Technology Letters* 16(1): 293-295.
Yun, S. H., C. Boudoux, et al. (2003). "High-speed wavelength-swept semiconductor laser with a polygon-scanner-based wavelength filter." *Optics Letters* 28(20): 1981-1983.
Yun, S. H., G. J. Tearney, et al. (2004). "Pulsed-source and swept-source spectral- domain optical coherence tomography with reduced motion artifacts." *Optics Express* 12(23): 5614-5624.
Yun, S. H., G. J. Tearney, et al. (2004). "Removing the depth-degeneracy in optical frequency domain imaging with frequency shifting." *Optics Express* 12(20): 4822-4828.
Yun, S. H., G. J. Tearney, et al. (2004). "Motion artifacts in optical coherence tomography with frequency-domain ranging." *Optics Express* 12(13): 2977-2998.
Zhang, J., J. S. Nelson, et al. (2005). "Removal of a mirror image and enhancement of the signal-to-noise ratio in Fourier-domain optical coherence tomography using an electro-optic phase modulator." *Optics Letters* 30(2): 147-149.
Zhang, Y., M. Sato, et al. (2001). "Numerical investigations of optimal synthesis of several low coherence sources for resolution improvement." *Optics Communications* 192(3-6): 183-192.
Zhang, Y., M. Sato, et al. (2001). "Resolution improvement in optical coherence tomography by optimal synthesis of light-emitting diodes." *Optics Letters* 26(4): 205-207.
Zhao, Y., Z. Chen, et al. (2002). "Real-time phase-resolved functional optical coherence tomography by use of optical Hilbert transformation." *Optics Letters* 27(2): 98-100.
Zhao, Y. H., Z. P. Chen, et al. (2000). "Doppler standard deviation imaging for clinical monitoring of in vivo human skin blood flow." *Optics Letters* 25(18): 1358-1360.
Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.
Zhou, D., P. R. Prucnal, et al. (1998). "A widely tunable narrow linewidth semiconductor fiber ring laser." *IEEE Photonics Technology Letters* 10(6): 781-783.
Zuluaga, a. F. And R. Richards-Kortum (1999). "Spatially resolved spectral interferometry for determination of subsurface structure." *Optics Letters* 24(8): 519-521.
Zvyagin, a. V., J. B. FitzGerald, et al. (2000). "Real-time detection technique for Doppler optical coherence tomography." *Optics Letters* 25(22): 1645-1647.
Marc Nikles et al., "Brillouin gain spectrum characterization in single-mode optical fibers", *Journal of Lightwave Technology* 1997, 15 (10): 1842-1851.
Tsuyoshi Sonehara et al., "Forced Brillouin Spectroscopy Using Frequency-Tunable Continuous-Wave Lasers", *Physical Review Letters* 1995, 75 (23): 4234-4237.
Hajime Tanaka et al., "New Method of Superheterodyne Light Beating Spectroscopy for BrillouinScattering Using Frequency-Tunable Lasers", *Physical Review Letters* 1995, 74 (9): 1609-1612.
Webb RH et al. "Confocal Scanning Laser Ophthalmoscope", *Applied Optics* 1987, 26 (8): 1492-1499.
Andreas Zumbusch et al. "Three-dimensional vibrational imaging by coherent anti-Stokes Raman scattering", *Physical Review Letters* 1999, 82 (20): 4142-4145.
Katrin Kneipp et al., "Single molecule detection using surface-enhanced Raman scattering (SERS)", *Physical Review Letters* 1997, 78 (9): 1667-1670.
K.J. Koski et al., "Brillouin imaging" *Applied Physics Letters* 87, 2005.
Boas et al., "Diffusing temporal light correlation for burn diagnosis", *SPIE*, 1999, 2979:468-477.
David J. Briers, "Speckle fluctuations and biomedical optics: implications and applications", *Optical Engineering*, 1993, 32(2):277-283.
Clark et al., "Tracking Speckle Patterns with Optical Correlation", *SPIE*, 1992, 1772:77-87.
Facchini et al., "An endoscopic system for DSPI", *Optik*, 1993, 95(1):27-30.
Hrabovsky, M., "Theory of speckle dispacement and decorrelation: application in mechanics", *SPIE*, 1998, 3479:345-354.

(56) References Cited

OTHER PUBLICATIONS

Sean J. Kirkpatrick et al., "Micromechanical behavior of cortical bone as inferred from laser speckle data", *Journal of Biomedical Materials Research*, 1998, 39(3):373-379.
Sean J. Kirkpatrick et al., "Laser speckle microstrain measurements in vascular tissue", *SPIE*, 1999, 3598:121-129.
Loree et al., "Mechanical Properties of Model Atherosclerotic Lesion Lipid Pools", *Arteriosclerosis and Thrombosis*, 1994, 14(2):230-234.
Podbielska, H. "Interferometric Methods and Biomedical Research", *SPIE*, 1999, 2732:134-141.
Richards-Kortum et al., "Spectral diagnosis of atherosclerosis using an optical fiber laser catheter", *American Heart Journal*, 1989, 118(2):381-391.
Ruth, B. "blood flow determination by the laser speckle method", *Int J Microcirc: Clin Exp*, 1990, 9:21-45.
Shapo et al., "Intravascular strain imaging: Experiments on an Inhomogeneous Phantom", *IEEE Ultrasonics Symposium* 1996, 2:1177-1180.
Shapo et al., "Ultrasonic displacement and strain imaging of coronary arteries with a catheter array", *IEEE Ultrasonics Symposium* 1995, 2:1511-1514.
Thompson et al., "Imaging in scattering media by use of laser speckle", *Opt. Soc. Am. A.*, 1997, 14(9):2269-2277.
Thompson et al., "Diffusive media characterization with laser speckle", *Applied Optics*, 1997, 36(16):3726-3734.
Tuchin, Valery V., "Coherent Optical Techniques for the Analysis of Tissue Structure and Dynamics," *Journal of Biomedical Optics*, 1999, 4(1):106-124.
M. Wussling et al., "Laser diffraction and speckling studies in skeletal and heart muscle", *Biomed, Biochim, Acta*, 1986, 45(1/2):S 23-S 27.
T. Yoshimura et al., "Statistical properties of dynamic speckles", *J. Opt. Soc. Am A.* 1986, 3(7):1032-1054.
Zimnyakov et al., "Spatial speckle correlometry in applications to tissue structure monitoring", *Applied Optics* 1997, 36(22): 5594-5607.
Zimnyakov et al., "A study of statistical to the diagnosis of structural changes in properties of partially developed speckle fields as applied human skin", *Optics and Spectroscopy*, 1994, 76(5): 747-753.
Zimnyakov et al., "Speckle patterns polarization analysis as an approach to turbid tissue structure monitoring", *SPIE* 1999, 2981:172-180.
Ramasamy Manoharan et al., "Biochemical analysis and mapping of atherosclerotic human artery using Ft-Ir microspectroscopy", *Atherosclerosis*, May 1993, 181-1930.
N.V. Salunke et al., "Biomechanics of Atherosclerotic Plaque" *Critical Reviews™ in Biomedical Engineering* 1997, 25(3):243-285.
D. Fu et al., "Non-invasive quantitative reconstruction of tissue elasticity using an iterative forward approach", Phys. Med. Biol. 2000 (45): 1495-1509.
S.B. Adams Jr. et al., "The use of polarization sensitive optical coherence tomography and elastography to assess connective tissue", Optical Soc. Of American Washington 2002, p. 3.
International Search Report for International Patent application No. PCT/US2005/039740 published Feb. 21, 2006.
International Written Opinion for International Patent application No. PCT/US2005/039740 published Feb. 21, 2006.
International Search Report for International Patent application No. PCT/US2005/030294 published Aug. 22, 2006.
International Written Opinion for International Patent application No. PCT/US2005/043951 published Apr. 6, 2006.
International Search Report for International Patent application No. PCT/US2005/043951 published Apr. 6, 2006.
Erdelyi et al. "Generation of diffraction-free beams for applications in optical microlithography", J. Vac. Sci. Technol. B 15 (12), Mar./Apr. 1997, pp. 287-292.
International Search Report for International Patent application No. PCT/US2005/023664 published Oct. 12, 2005.
International Written Opinion for International Patent application No. PCT/US2005/023664 published Oct. 12, 2005.
Tearney et al., "Spectrally encoded miniature endoscopy" Optical Society of America; Optical Letters vol. 27, No. 6, Mar. 15, 2002; pp. 412-414.
Yelin et al., "Double-clad Fiber for Endoscopy" Optical Society of America; Optical Letters vol. 29, No. 20, Oct. 16, 2005; pp. 2408-2410.
International Search Report for International Patent application No. PCT/US2001/049704 published Dec. 10, 2002.
International Search Report for International Patent application No. PCT/US2004/039454 published May 11, 2005.
International Written Opinion for International Patent application No. PCT/US2004/039454 published May 11, 2005.
PCT International Preliminary Report on Patentability for International Application No. PCT/US2004/038404 dated Jun. 2, 2006.
Notice of Reasons for Rejection and English translation for Japanese Patent Application No. 2002-538830 dated May 12, 2008.
Office Action dated Aug. 24, 2006 for U.S. Appl. No. 10/137,749.
Barry Cense et al., "Spectral-domain polarization-sensitive optical coherence tomography at 850nm", Coherence Domain Optical Methods and Optical Coherence Tomography in Biomedicine IX, 2005, pp. 159-162.
A. Ymeti et al., "Integration of microfluidics with a four-channel integrated optical Young interferometer immunosensor", Biosensors and Bioelectronics, Elsevier Science Publishers, 2005, pp. 1417-1421.
PCT International Search Report for Application No. PCT/US2006/018865 filed May 5, 2006.
International Written Opinion for International Patent application No. PCT/US2006/018865 filed May 5, 2006.
John M. Poneros, "Diagnosis of Barrett's esophagus using optical coherence tomography", Gastrointestinal Endoscopy clinics of North America, 14 (2004) pp. 573-588.
P.F. Escobar et al., "Diagnostic efficacy of optical coherence tomography in the management of preinvasive and invasive cancer of uterine cervix and vulva", Int. Journal of Gynecological Cancer 2004, 14, pp. 470-474.
Ko T et al., "Ultrahigh resolution in vivo versus ex vivo OCT imaging and tissue preservation", Conference on Lasers and electro-optics, 2001, pp. 252-253.
Paul M. Ripley et al., "A comparison of Artificial Intelligence techniques for spectral classification in the diagnosis of human pathologies based upon optical biopsy", Journal of Optical Society of America, 2000, pp. 217-219.
Wolfgang Drexler et al., "Ultrahigh-resolution optical coherence tomography", Journal of Biomedical Optics SPIE USA, 2004, pp. 47-74.
PCT International Search Report for Application No. PCT/US2006/016677 filed Apr. 28, 2006.
International Written Opinion for International Patent application No. PCT/US2006/016677 filed Apr. 28, 2006.
Office Action dated Nov. 13, 2006 for U.S. Appl. No. 10/501,268.
Office Action dated Nov. 20, 2006 for U.S. Appl. No. 09/709,162.
PCT International Search Report and Written Opinion for Application No. PCT/US2004/023585 filed Jul. 23, 2004.
Office Action dated Dec. 6, 2006 for U.S. Appl. No. 10/997,789.
Elliott, K. H. "The use of commercial CCD cameras as linear detectors in the physics undergraduate teaching laboratory", European Journal of Physics, 1998, pp. 107-117.
Lauer, V. "New approach to optical diffraction tomography yielding a vector equation of diffraction tomography and a novel tomographic microscope", Journal of Microscopy vol. 205, Issue 2, 2002, pp. 165-176.
Yu, P. et al. "Imaging of tumor necroses using full-frame optical coherence imaging", Proceedings of SPIE vol. 4956, 2003, pp. 34-41.
Zhao, Y. et al. "Three-dimensional reconstruction of in vivo blood vessels in human skin using phase-resolved optical Doppler tomography", IEEE Journal of Selected Topics in Quantum Electronics 7.6 (2001): 931-935.
Office Action dated Dec. 18, 2006 for U.S. Appl. No. 10/501,276.

(56) References Cited

OTHER PUBLICATIONS

Devesa, Susan S. et al. (1998) "Changing Patterns in the Incidence of Esophegeal and Gastric Carcinoma in the United States." *American Cancer Society* vol. 83, No. 10 pp. 2049-2053.
Barr, H et al. (2005) "Endoscopic Therapy for Barrett's Oesophaugs" *Gut* vol. 54:875-884.
Johnston, Mark H.(2005) "Technology Insight: Ablative Techniques for Barrett's Esophagus—Current and Emerging Trends" www.Nature.com/clinicalpractice/gasthep.
Falk, Gary W. et al. (1997) "Surveillance of Patients with Barrett's Esophagus for Dysplasia and Cancer with Ballon Cytology" *Gastrorenterology* vol. 112, pp. 1787-1797.
Sepchler, Stuart Jon. (1997) "Barrett's Esophagus: Should We Brush off this Balloning Problem?" *Gastroenterology* vol. 112, pp. 2138-2152.
Froehly, J. et al. (2003) "Multiplexed 3D Imaging Using Wavelength Encoded Spectral Interferometry: A Proof of Principle" *Optics Communications* vol. 222, pp. 127-136.
Kubba A.K. et al. (1999) "Role of p53 Assessment in Management of Barrett's Esophagus" *Digestive Disease and Sciences* vol. 44, No. 4. pp. 659-667.
Reid, Brian J. (2001) "p53 and Neoplastic Progression in Barrett's Esophagus" *The American Journal of Gastroenterology* vol. 96, No. 5, pp. 1321-1323.
Sharma, P. et al.(2003) "Magnification Chromoendoscopy for the Detection of Intestinal Metaplasia and Dysplasia in Barrett's Oesophagus" *Gut* vol. 52, pp. 24-27.
Kuipers Ej et al. (2005) "Diagnostic and Therapeutic Endoscopy" *Journal of Surgical Oncology* vol. 92, pp. 203-209.
Georgakoudi, Irene et al. (2001) "Fluorescence, Reflectance, and Light-Scattering Spectroscopy for Evaluating Dysplasia in Patients with Barrett's Esophagus" *Gastroenterology* vol. 120, pp. 1620-1629.
Adrain, Alyn L. et al. (1997) "High-Resolution Endoluminal Sonography is a Sensitive Modality for the Identification of Barrett's Meaplasia" *Gastrointestinal Endoscopy* vol. 46, No. 2, pp. 147-151.
Canto, Marcia Irene et al (1999) "Vital Staining and Barrett's Esophagus" 9*Gastrointestinal Endoscopy* vol. 49, No. 3, part 2, pp. 12-16.
Evans, John A. et al. (2006) "Optical Coherence Tomography to Identify Intramucosal Carcinoma and High-Grade Dysplasia in Barrett's Esophagus" *Clinical Gastroenterology and Hepatology* vol. 4, pp. 38-3.
Poneros, John M. et al. (2001) "Diagnosis of Specialized Intestinal Metaplasia by Optical Coherence Tomography" *Gastroenterology* vol. 120, pp. 7-12.
Ho, W. Y. et al. (2005) "115 KHz Tuning Repetition Rate Ultrahigh-Speed Wavelength-Swept Semiconductor Laser" *Optics Letters* col. 30, No. 23, pp. 3159-3161.
Brown, Stanley B. et al. (2004) "The Present and Future Role of Photodynamic Therapy in Cancer Treatment" *The Lancet Oncology* vol. 5, pp. 497-508.
Boogert, Jolanda Van Den et al. (1999) "Endoscopic Ablation Therapy for Barrett's Esophagua with High-Grade Dysplasia: A Review" *The American Journal of Gastroenterology* vol. 94, No. 5, pp. 1153-1160.
Sampliner, Richard E. et al. (1996) "Reversal Multipolar Electrocoagulation: Preliminary pp. 532-535 of Barrett's Esophagus with Acid Suppression and Results" *Gastrointestinal Endoscopy* vol. 44, No. 5,.
Sampliner, Richard E. (2004) "Endoscopic Ablative Therapy for Barrett's Esophagus: Current Status" *Gastrointestinal Endoscopy* vol. 59, No. 1, pp. 66-69.
Soetikno, Roy M. et al. (2003) "Endoscopic Mucosal resection" *Gastrointestinal Endoscopy* vol. 57, No. 4, pp. 567-579.
Ganz, Robert A. et al. (2004) "Complete Ablation of Esophageal Epithelium with a Balloon-based Bipolar Electrode: A Phased Evaluation in the Porcine and in the Human Esophagus" *Gastrointestinal Endoscopy* vol. 60, No. 6, pp. 1002-1010.
Pfefer, Jorje at al. (2006) "Performance of the Aer-O-Scope, a Pneumatic, Self Propelling, Self Navigating Colonoscope in Animal Experiments" *Gastrointestinal Endoscopy* vol. 63, No. 5, pp. AB223.
Overholt, Bergein F. et al. (1999) "Photodynamic Therapy for Barrett's Esophagus: Follow-Up in 100 Patients" *Gastrointestinal Endoscopy* vol. 49, No. 1, pp. 1-7
Vogel, Alfred et al. (2003) "Mechanisms of Pulsed Laser Ablation of Biological Tissues" *American Chemical Society* vol. 103, pp. 577-644
McKenzie, a. L. (1990) "Physics of Thermal Processes in Laser-Tissue Interaction" *Phys. Med. Biol* vol. 35, No. 9, pp. 1175-1209.
Anderson, R. Rox et al. (1983) "Selective Photothermolysis Precise Microsurgery by Selective Absorption of Pulsed Radiation" *Science* vol. 220, No. 4596, pp. 524-527.
Jacques, Steven L. (1993) "Role of Tissue Optics and Pulse Duration on Tissue Effects During High-Power Laser Irradiation" *Applied Optics* vol. 32, No. 13, pp. 2447-2454.
Nahen, Kester et al. (1999) "Investigations on Acosustic On-Line Monitoring of IR Laser Ablation of burned Skin" *Lasers in Surgery and Medicine* vol. 25, pp. 69-78.
Jerath, Maya R. et al. (1993) "Calibrated Real-Time Control of Lesion Size Based on Reflectance Images" *Applied Optics* vol. 32, No. 7, pp. 1200-1209.
Jerath, Maya R. et al (1992) "Dynamic Optical Property Changes: Implications for Reflectance Feedback Control of Photocoagulation" *Journal of Photochemical,.Photobiology. B: Biol* vol. 16, pp. 113-126.
Deckelbaum, Lawrence I. (1994) "Coronary Laser Angioplasty" *Lasers in Surgery and Medicine* vol. 14, pp. 101-110.
Kim, B.M. et al. (1998) "Optical Feedback Signal for Ultrashort Laser Pulse Ablation of Tissue" *Applied Surface Science* vol. 127-129, pp. 857-862.
Brinkman, Ralf et al. (1996)"Analysis of Cavitation Dynamics During Pulsed Laser Tissue Ablation by Optical On-Line Monitoring" *IEEE Journal of Selected Topics in Quantum Electronics* vol. 2, No. 4, pp. 826-835.
Whelan, W.M. et al. (2005) "A novel Strategy for Monitoring Laser Thermal Therapy Based on Changes in Optothermal Properties of Heated Tissues" International *Journal of Thermophysics* vol.26., No. 1, pp. 233-241
Thomsen, Sharon et al. (1990) "Microscopic Correlates of Macroscopic Optical Property Changes During Thermal Coagulation of Myocardium" *SPIE* vol. 1202, pp. 2-11.
Khan, Misban Huzaira et al. (2005) "Intradermally Focused Infrared Laser Pulses: Thermal Effects at Defined Tissue Depths" *Lasers in Surgery and Medicine* vol. 36, pp. 270-280.
Neumann, R.A. et al. (1991) "Enzyme Histochemical Analysis of Cell Viability After Argon Laser-Induced Coagulation Necrosis of the Skin" *Journal of the American Academy of Dermatology* vol. 25, No. 6, pp. 991-998.
Nadkarni, Seemantini K. et al (2005) "Charaterization of Atherosclerotic Plaques by Laser Speckle Imaging" *Circulation* vol. 112, pp. 885-892.
Zimnyakov, Dmitry A. et al (2002) "Speckle-Contrast Monitoring of Tissue Thermal Modification" *Applied Optics* vol. 41, No. 28, pp. 5989-5996.
Morelli, J.G., et al (1986) "Tunable Dye Laser (577 nm) Treatment of Port Wine Stains" *Lasers in Surgery and Medicine* vol. 6, pp. 94-99.
French, P.M.W. et al. (1993) "Continuous-wave Mode-Locked $Cr^{4+}$: YAG Laser" *Optics Letters* vol. 18, No. 1, pp. 39-41.
Sennaroglu, Alphan at al. (1995) "Efficient Continuous-Wave Chromium-Doped Yag Laser" *Journal of Optical Society of America* vol. 12, No. 5, pp. 930-937.
Bouma, B et al. (1994) "Hybrid Mode Locking of a Flash-Lamp-Pumped Ti: $Al_2O_3$ Laser" *Optics Letters* vol. 19, No. 22, pp. 1858-1860.
Bouma, B et al. (1995) "High Resolution Optical Coherence Tomography Imaging Using a Mode-Locked Ti: $Al_2O_3$ Laser Source" *Optics Letters* vol. 20, No. 13, pp. 1486-1488.
Fernandez, Cabrera Delia et al. "Automated detection of retinal layer structures on optical coherence tomography images", *Optics Express* vol. 13, No. 25, Oct. 4, 2005, pp. 10200-10216.

(56) References Cited

OTHER PUBLICATIONS

Ishikawa, Hiroshi et al. "Macular Segmentation with optical coherence tomography", Investigative Ophthalmology & Visual Science, vol. 46, No. 6, Jun. 2005, pp. 2012-2017.
Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.
PCT International Search Report and Written Opinion for Application No. PCT/US2006/031905 dated May 3, 2007.
PCT International Search Report and Written Opinion for Application No. PCT/US2007/060481 dated May 23, 2007.
PCT International Search Report and Written Opinion for Application No. PCT/US2007/060717 dated May 24, 2007.
PCT International Search Report and Written Opinion for Application No. PCT/US2007/060319 dated Jun. 6, 2007.
D. Yelin et al., "Three-dimensional imaging using spectral encoding heterodyne interferometry", Optics Letters, Jul. 15, 2005, vol. 30, No. 14, pp. 1794-1796.
Akiba, Masahiro et al. "En-face optical coherence imaging for three-dimensional microscopy", Spie, 2002, pp. 8-15.
Office Action dated Aug. 10, 2007 for U.S. Appl. No. 10/997,789.
Office Action dated Feb. 2, 2007 for U.S. Appl. No. 11/174,425.
PCT International Search Report and Written Opinion for Application No. PCT/US2007/060657 dated Aug. 13, 2007.
Lewis, Neil E. et al., (2006) "Applications of Fourier Transform Infrared Imaging Microscopy in Neurotoxicity", Annals New York Academy of Sciences, Dec. 17, 2006, vol. 820, pp. 234-246.
Joo, Chulmin et al., Spectral-domain optical coherence phase microscopy for quantitative phase-contrast imaging, Optics Letters, Aug. 15, 2005, vol. 30, No. 16, pp. 2131-2133.
Guo, Bujin et al., "Laser-based mid-infrared reflectance imaging of biological tissues", Optics Express, Jan. 12, 2004, vol. 12, No. 1, pp. 208-219.
Office Action dated Mar. 28, 2007 for U.S. Appl. No. 11/241,907.
Office Action dated May 23, 2007 for U.S. Appl. No. 10/406,751.
Office Action dated May 23, 2007 for U.S. Appl. No. 10/551,735.
PCT International Search Report and Written Opinion for Application No. PCT/US2007/061815 dated Aug. 2, 2007.
Sir Randall, John et al., "Brillouin scattering in systems of biological significance", Phil. Trans. R. Soc. Lond. A 293, 1979, pp. 341-348.
Takagi, Yasunari, "Application of a microscope to Brillouin scattering spectroscopy", Review of Scientific Instruments, No. 12, Dec. 1992, pp. 5552-5555.
Lees, S. et al., "Studies of Compact Hard Tissues and Collagen by Means of Brillouin Light Scattering", Connective Tissue Research, 1990, vol. 24, pp. 187-205.
Berovic, N. "Observation of Brillion scattering from single muscle fibers", European Biophysics Journal, 1989, vol. 17, pp. 69-74.
PCT International Search Report and Written Opinion for Application No. PCT/US2007/062465 dated Aug. 8, 2007.
Pythila John W. et al., "Rapid, depth-resolved light scattering measurements using Fourier domain, angle-resolved low coherence interferometry", Optics Society of America, 2004.
Pyhtila John W. et al., "Determining nuclear morphology using an improved angle-resolved low coherence interferometry system", Optics Express, Dec. 15, 2003, vol. 11, No. 25, pp. 3473-3484.
Desjardins A.E., et al., "Speckle reduction in Oct using massively-parallel detection and frequency-domain ranging", Optics Express, May 15, 2006, vol. 14, No. 11, pp. 4736-4745.
Nadkarni, Seemantini K., et al., "Measurement of fibrous cap thickness in atherosclerotic plaques by spatiotemporal analysis of laser speckle images", Journal of Biomedical Optics, vol. 11 Marsh/Apr. 2006, pp. 021006-1-8.
PCT International Search Report and Written Opinion for Application No. PCT/US2007/066017 dated Aug. 30, 2007.
Yamanari M. et al., "Polarization sensitive Fourier domain optical coherence tomography with continuous polarization modulation", Proc. Of SPIE, vol. 6079, 2006.
Zhang Jun et al., "Full range polarization-sensitive Fourier domain optical coherence tomography", Optics Express, Nov. 29, 2004, vol. 12, No. 24, pp. 6033-6039.
European Patent Office Search report for Application No. 01991092.6-2305 dated Jan. 12, 2006.
PCT International Search Report and Written Opinion for Application No. PCT/US2007/060670 dated Sep. 21, 2007.
J. M. Schmitt et al., (1999) "Speckle in Optical Coherence Tomography: An Overview", SPIE vol. 3726, pp. 450-461.
Office Action dated Oct. 11, 2007 for U.S. Appl. No. 11/534,095.
Office Action dated Oct. 9, 2007 for U.S. Appl. No. 09/709,162.
Notice of Allowance dated Oct. 3, 2007 for U.S. Appl. No. 11/225,840.
Siavash Yazdanfar et al., "In Vivo imaging in blood flow in human retinal vessels using color Doppler optical coherence tomography", SPIE, 1999 vol. 3598, pp. 177-184.
Office Action dated Oct. 30, 2007 for U.S. Appl. No. 11/670,069.
Tang C. L. et al., "Wide-band electro-optical tuning of semiconductor lasers", Applied Physics Letters, vol. 30, No. 2, Jan. 15, 1977, pp. 113-116.
Tang C. L. et al., "Transient effects in wavelength-modulated dye lasers", Applied Physics Letters, vol. 26, No. 9, May 1, 1975, pp. 534-537.
Telle M. John, et al., "Very rapid tuning of cw dye laser", Applied Physics Letters, vol. 26, No. 10, May 15, 1975, pp. 572-574.
Telle M. John, et al., "New method for electro-optical tuning of tunable lasers", Applied Physics Letters, vol. 24, No. 2, Jan. 15, 1974, pp. 85-87.
Schmitt M. Joseph et al. "Oct elastography: imaging microscopic deformation and strain of tissue", Optics Express, vol. 3, No. 6, Sep. 14, 1998, pp. 199-211.
M. Gualini Muddassir et al., "Recent Advancements of Optical Interferometry Applied to Medicine", IEEE Transactions on Medical Imaging, vol. 23, No. 2, Feb. 2004, pp. 205-212.
Maurice L. Roch et al. "Noninvasive Vascular Elastography: Theoretical Framework", IEEE Transactions on Medical Imaging, vol. 23, No. 2, Feb. 2004, pp. 164-180.
Kirkpatrick J. Sean et al. "Optical Assessment of Tissue Mechanical Properties", Proceedings of the SPIE—the International Society for Optical Engineering Spie - vol. 4001, 2000, pp. 92-101.
Lisauskas B. Jennifer et al., "Investigation of Plaque Biomechanics from Intravascular Ultrasound Images using Finite Element Modeling", Proceedings of the 19th International Conference—IEEE Oct. 30-Nov. 2, 1997, pp. 887-888.
Parker K. J. et al., "Techniques for Elastic Imaging: A Review", IEEE Engineering in Medicine and Biology, Nov./Dec. 1996, pp. 52-59.
European Patent Office Search Report dated Nov. 20, 2007 for European Application No. 05791226.3.
Dubois Arnaud et al., "Ultrahigh-resolution Oct using white-light interference microscopy", Proceedings of Spie, 2003, vol. 4956, pp. 14-21 44.
Office Action dated Jan. 3, 2008 for U.S. Appl. No. 10/997,789.
Office Action dated Dec. 21, 2007 for U.S. Appl. No. 11/264,655.
Office Action dated Dec. 18, 2007 for U.S. Appl. No. 11/288,994.
Office Action dated Jan. 10, 2008 for U.S. Appl. No. 11/435,228.
Office Action dated Jan. 10, 2008 for U.S. Appl. No. 11/410,937.
Office Action dated Jan. 11, 2008 for U.S. Appl. No. 11/445,990.
Office Action dated Feb. 4, 2008 for U.S. Appl. No. 10/861,179.
PCT International Search Report and Written Opinion for Application No. PCT/US2007/061463 dated Jan. 23, 2008.
PCT International Search Report and Written Opinion for Application No. PCT/US2007/061481 dated Mar. 17, 2008.
PCT International Search Report and Written Opinion for Application No. PCT/US2007/078254 dated Mar. 28, 2008.
Sadhwani, Ajay et al., "Determination of Teflon thickness with laser speckle I. Potential for burn depth diagnosis", Optical Society of America, 1996, vol. 35, No. 28, pp. 5727-5735.
C.J. Stewart et al., "A comparison of two laser-based methods for determination of burn scar perfusion: Laser Doppler versus laser speckle imaging", Elsevier Ltd., 2005, vol. 31, pp. 744-752.
G. J. Tearney et al., "Atherosclerotic plaque characterization by spatial and temporal speckle pattern analysis", CLEO 2001, vol. 56, pp. 307-307.

(56) References Cited

OTHER PUBLICATIONS

PCT International Search Report for Application No. PCT/US2007/068233 dated Feb. 21, 2008.

PCT International Search Report for Application No. PCT/US2007/060787 dated Mar. 18, 2008.

Statement under Article 19 and Reply to PCT Written Opinion for PCT International Application No. PCT/US2005/043951 dated Jun. 6, 2006.

PCT International Preliminary Report on Patentability for Application No. PCT/US2005/043951 dated Jun. 7, 2007.

* cited by examiner

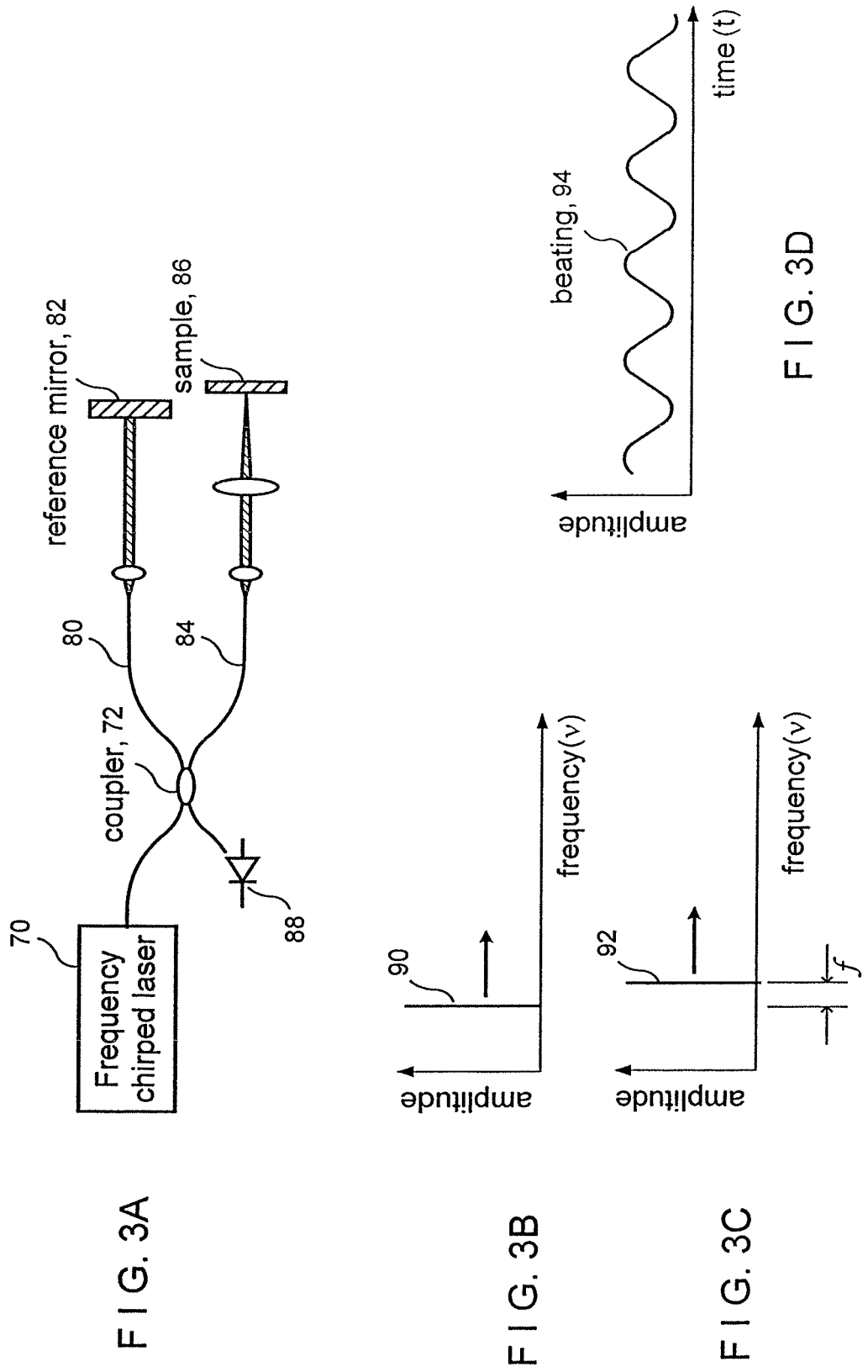

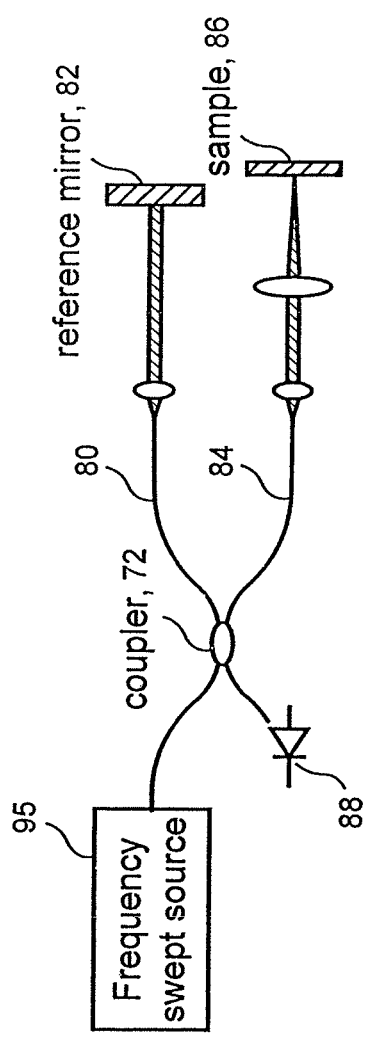
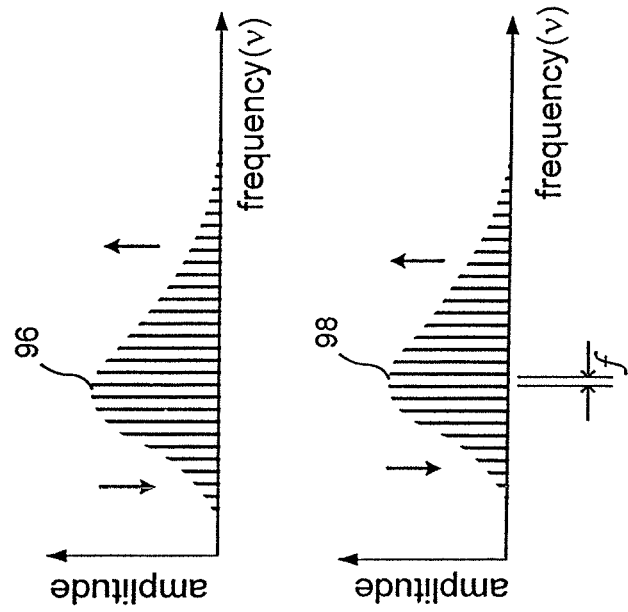
FIG. 4A
FIG. 4B
FIG. 4C
FIG. 4D

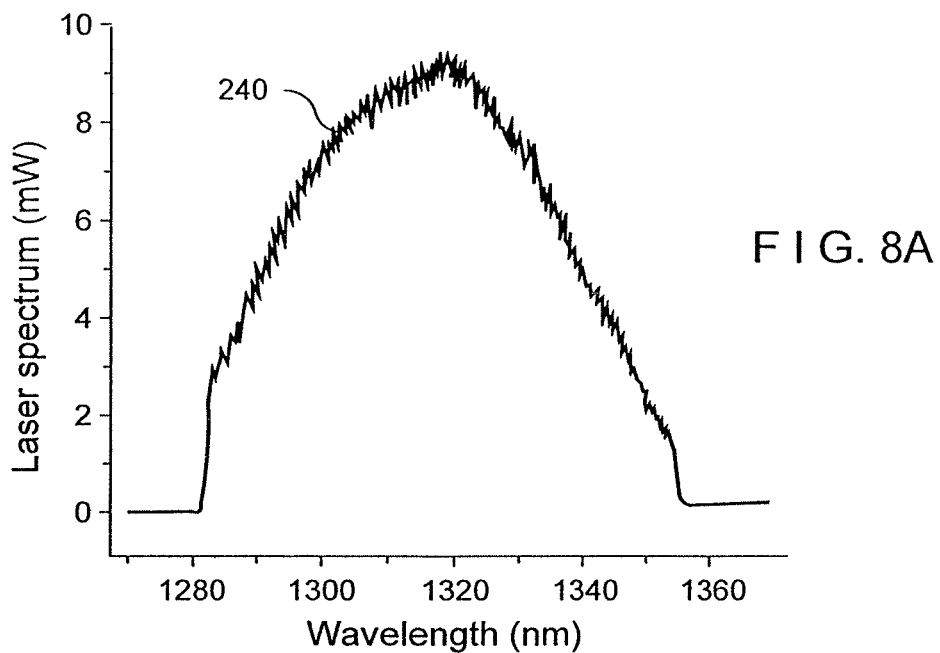
F I G. 8A
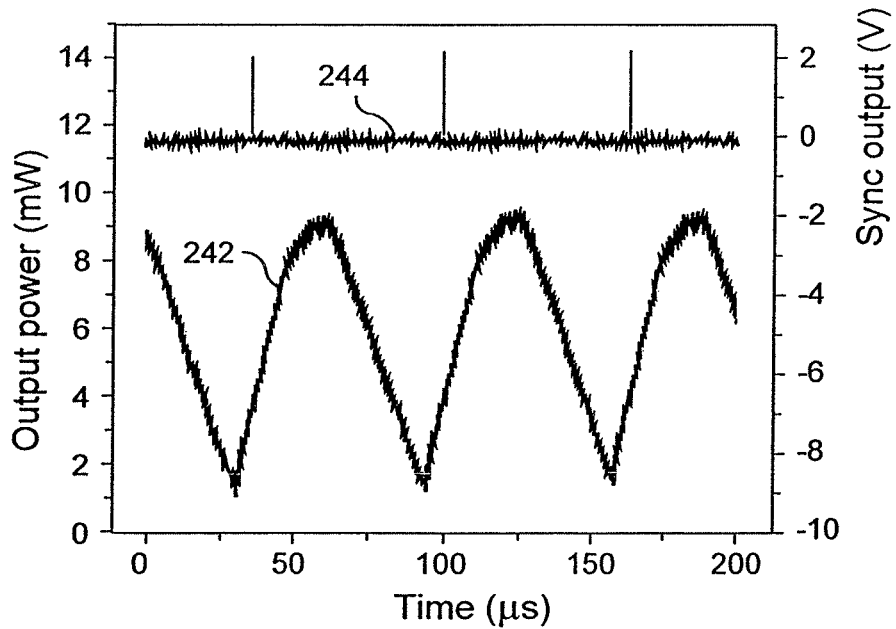
F I G. 8B

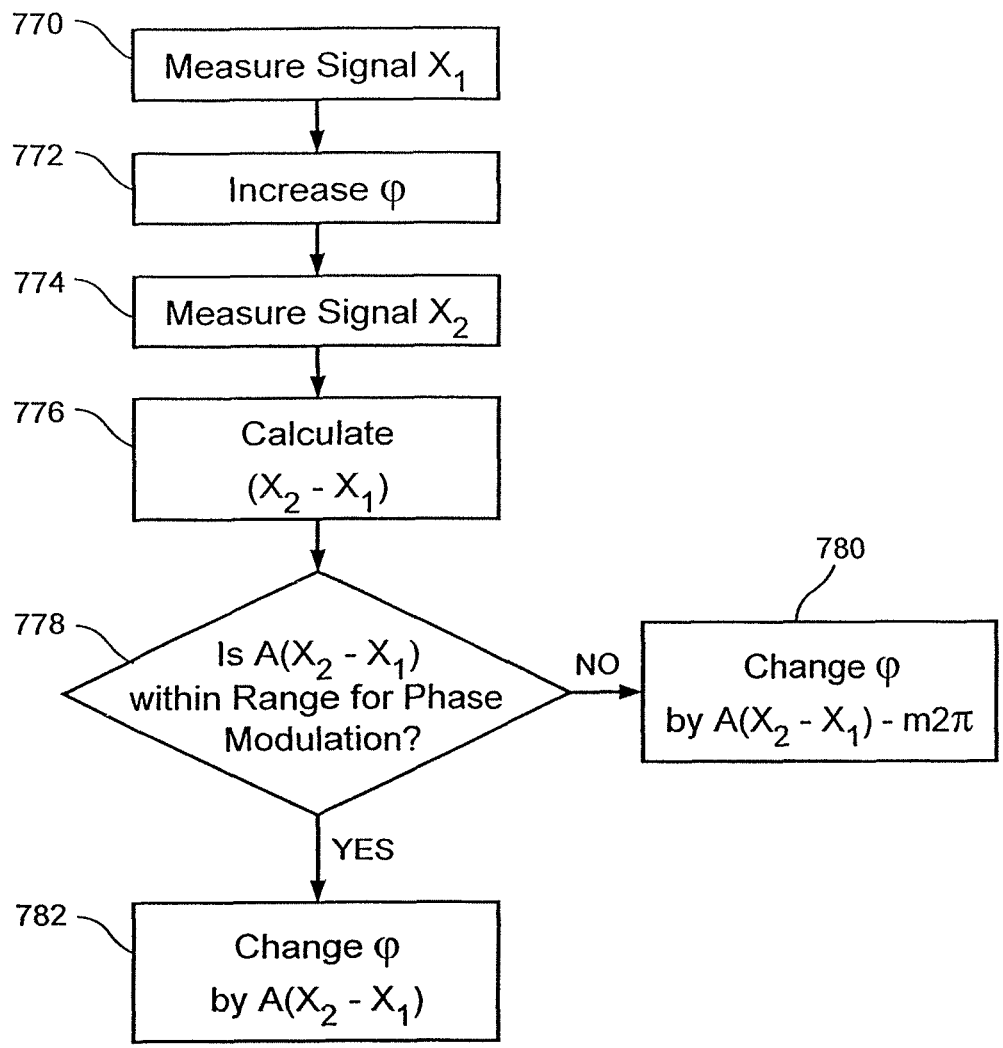
F I G. 14C

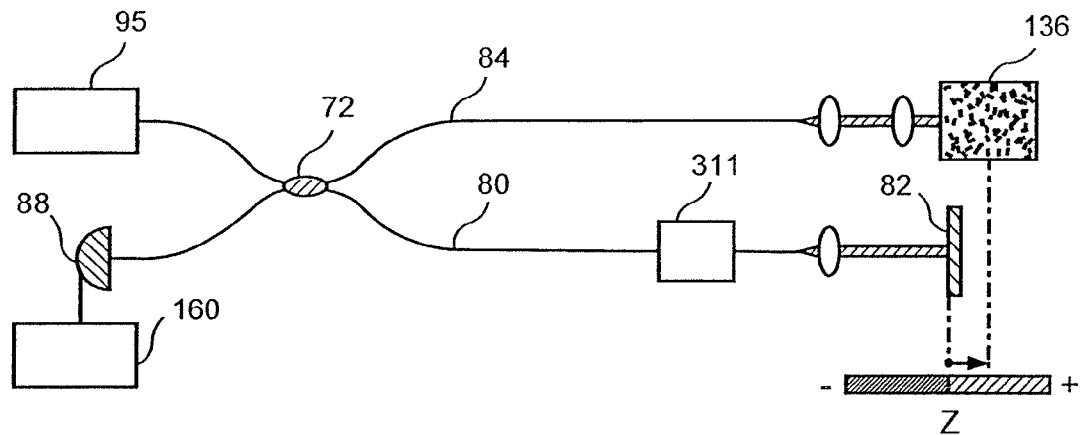
F I G. 15
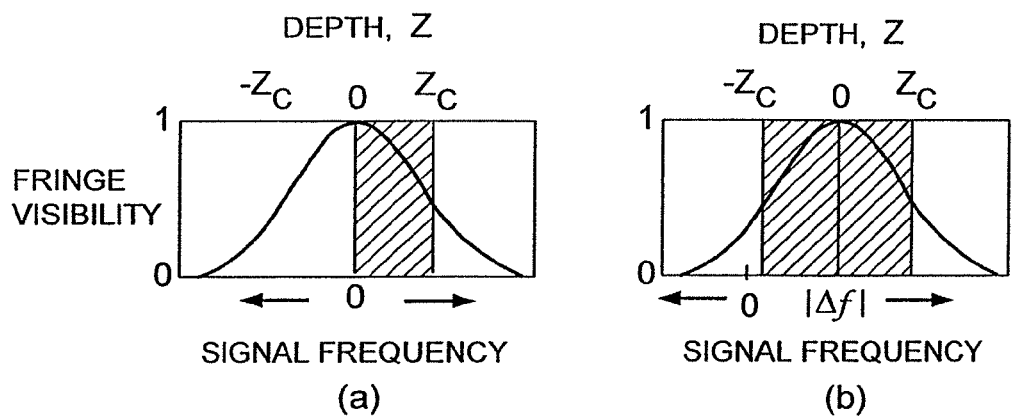
F I G. 16

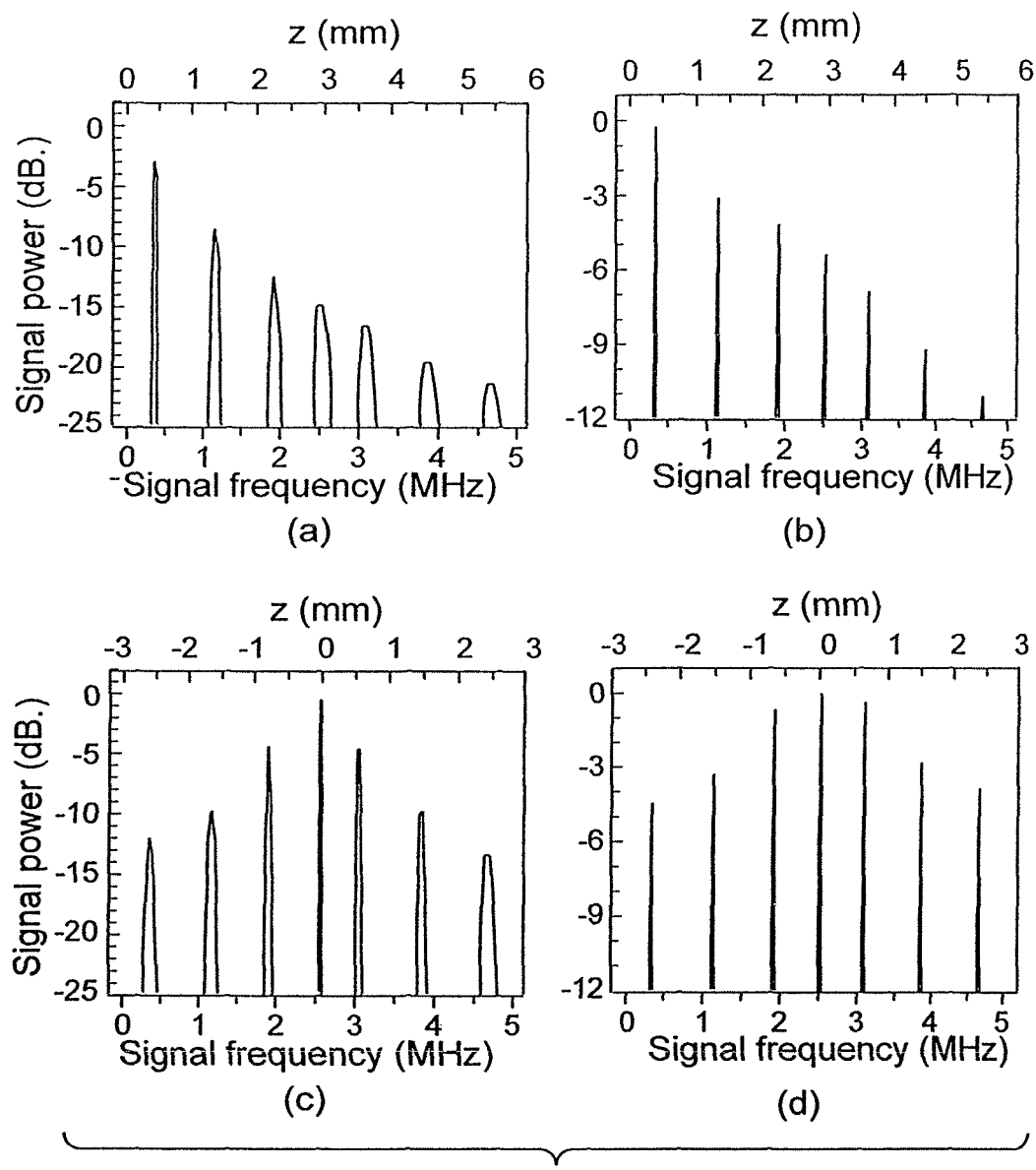
F I G. 18

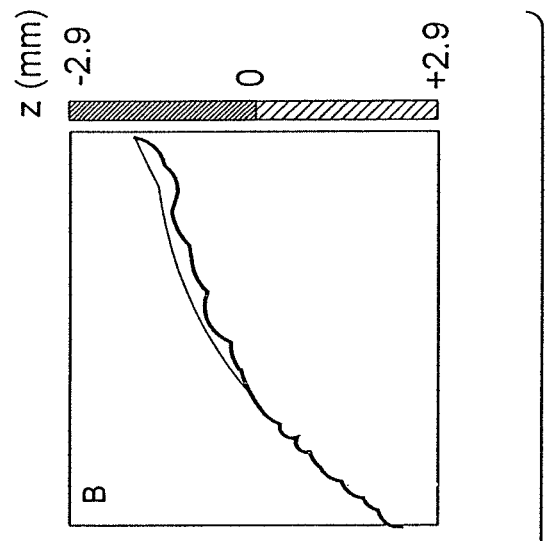
FIG. 19A
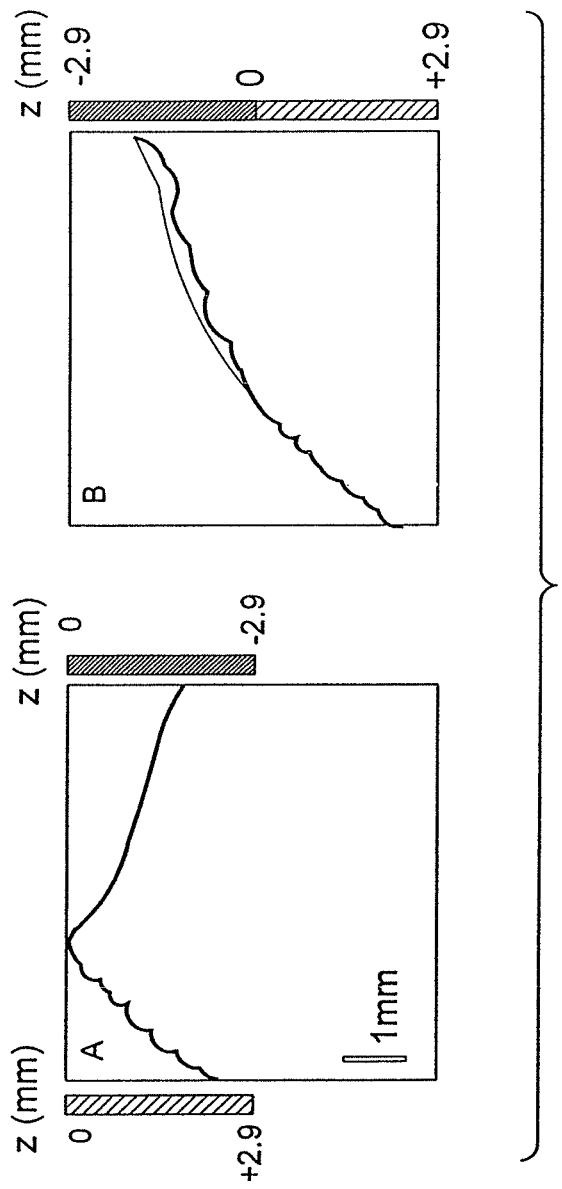
FIG. 19B
FIG. 19

METHOD AND APPARATUS FOR PERFORMING OPTICAL IMAGING USING FREQUENCY-DOMAIN INTERFEROMETRY

CROSS REFERENCE TO RELATED APPLICATION(S)

The present application is a continuation of U.S. patent application Ser. No. 13/191,885 filed on Jul. 27, 2011, which is a continuation of U.S. patent application Ser. No. 12/795,529 filed on Jun. 7, 2010, which is a continuation of U.S. patent application Ser. No. 10/577,562 filed Apr. 27, 2006, which issued as U.S. Pat. No. 7,733,497 issued on Jun. 8, 2010, which is a national phase of PCT/US2004/029148 filed on Sep. 8, 2004, the entire disclosures of which are incorporated herein by reference. This application also claims priority from U.S. Provisional Patent Application Ser. No. 60/514,769 filed on Oct. 27, 2003, the entire disclosure of which is incorporated herein by reference.

FIELD OF THE INVENTION

The present invention relates generally optical imaging, and more particularly to method and apparatus for performing optical imaging using frequency-domain interferometry.

BACKGROUND OF THE INVENTION

As is known in the art, optical interferometric reflectometry is a powerful tool for performing non-invasive, high-resolution (~10 µm), cross-sectional imaging of a biological or other sample, to visualize micro-structural optical properties such as reflection, absorption, scattering, attenuation, birefringence, and spectroscopic analysis. There are a number of interferometric imaging techniques that are known in the art. These techniques in general can be divided into two major categories: (i) time-domain technique, and (ii) frequency-domain technique.

Low coherence interferometry ("LCI") is one of the time-domain techniques. This technique uses a scanning system to vary the reference arm length and acquire the interference signal at a detector. Then, the fringe pattern is demodulated to obtain the coherence envelope of the source cross correlation function. Optical coherence tomography ("OCT") is a technique for obtaining two- or three-dimensional images using LCI. OCT is described in U.S. Pat. No. 5,321,501 issued to Swanson et al. Multiple variants of the OCT techniques have been described, but many suffer from less than optimal signal to noise ratio ("SNR"), resulting in non-optimal resolution, low imaging frame rates, and poor depth of penetration. Power usage is a factor in such imaging techniques. For example in ophthalmic uses, only a certain number of milliwatts of power are tolerable before thermal damage can occur. Thus, boosting power is not feasible to increase SNR in such environments. Nevertheless, it would be desirable to have an imaging method with superior SNR without appreciably increasing power requirements.

Insufficient SNR can also prevent the OCT technique from being used at a high frame rate which is important to avoid motion artifacts and overcome the short measurement time window available, for example, for in-vivo vascular imaging. Therefore, a way to improve SNR and imaging speed (e.g., the frame rate) is desired. Spectral interferometry, or spectral radar, is one of the frequency-domain imaging techniques. In spectral radar, the real part of the cross spectral density of sample and reference arm light is measured with a spectrometer. Depth profile information can be encoded on the cross-spectral density modulation.

The use of spectral radar concepts to increase SNR of LCI and OCT has been described previously. This technique uses a charge coupled device ("CCD") with a large number of pixels (an order of 1,000) to reach scan ranges on the order of a millimeter. The fast readout of the CCD device makes high-speed imaging possible.

There are, however, a number of disadvantages associated with using a CCD device. First, CCD devices are relatively expensive compared to a single-element photo-receiver. Secondly, the previously described method uses a single CCD to acquire the data. Since the charge storage capacity is limited, it requires a reduction of the reference arm power to approximately the same level as the sample arm power, giving rise to auto correlation noise on the sample arm light. In addition, since no carrier is generated, the 1/f noise will dominate the noise in this system. Thirdly, even with the short integration times of state of the art CCD technology, phase instabilities in the interferometer reduce fringe visibility of the cross spectral density modulation. This shortcoming makes the technique vulnerable to motion artifacts.

Coherent frequency-modulated continuous-wave reflectometry (C-FMCW) is another frequency domain technique known in the art. U.S. Pat. Nos. 5,956,355 and 6,160,826 issued to Swanson et al. describes an optical imaging method and apparatus using this technique. The previously described imaging method is based on using a continuously-tuned single-frequency laser as an optical source. The tuning wavelength range is required to be several tens of nanometers to achieve ranging resolution of less than 100 microns. The instantaneous linewidth of the laser must be less than approximately 0.1 nm to achieve a detection range on the order of 1.0 mm. The tuning rate should be greater than 10 kHz for high speed (e.g., video-rate) imaging. Although an external-cavity semiconductor laser can be configured to achieve mode-hop-free single-frequency tuning over several tens of nanometer, the tuning rate has been less than 1 Hz due to stringent requirement on mechanical stability. A way to overcome this speed difficulty is preferable.

It would, therefore, be desirable to provide a system and method to overcome the source availability and scan speed shortcomings of conventional LCI and OCT.

SUMMARY OF THE INVENTION

In accordance with exemplary embodiments of the present invention, an exemplary optical frequency domain imaging ("OFDI") system can include a multiple-frequency-mode (or multiple longitudinal or axial-mode) wavelength-swept laser source optically coupled to an interferometer containing a sample under study. The system can further include an arrangement which is configured to produce interferometric signals in quadrature between light reflected from a sample and a reference light and a detector disposed to receive the interferometric signals.

With such exemplary particular arrangement, an OFDI system which can operate with source powers that are relatively low compared with source powers of conventional systems and/or which operate at acquisition rates which are relatively high compared with acquisition rates of conventional systems may be provided. The use of a swept source results in an imaging system having reduced shot noise and other forms of noise which allows for much lower source powers, or much higher acquisition rates than conventional systems. This can lead to an increased detection sensitivity which results in the ability to provide real time imaging. Such imaging speed can assist practitioners in gastrointestinal, ophthalmic and arterial imaging fields, where motion artifacts are a continuing problem. By increasing a frame rate while maintaining or improving the signal to noise ratio such artifacts can be minimized or in some cases eliminated. Exemplary embodiments of the present invention may also enable the screening of large areas of tissues with OFDI and allows enables the use of clinically viable screening protocols.

In one exemplary embodiment of the present invention, the wavelength-swept laser can be provided that may use an optical band-pass scanning filter in the laser cavity to produce a rapidly-swept multiple-frequency-mode output. By using an optical band-pass scanning filter in the laser cavity, it is not necessary to tune the laser cavity length to provide synchronous tuning of the laser spectrum. In other words, it does not require tuning the longitudinal cavity mode of the laser at the same rate as the center wavelength of the laser.

In another exemplary embodiment of the present invention, the detector can be a dual-balanced receiver disposed to accept interferometric signals and to suppress the relative intensity noise in the interferometric signals.

The gain in signal-to-noise ratio ("SNR") according to an exemplary embodiment of the present invention is advantageous over time-domain approaches such as OCT via a performance of the signal processing in the Fourier-domain. The SNR enhancement is by a factor of N, the ratio of the depth range to the spatial resolution. The enhancement factor N can reach a few hundreds to several thousand. This increase in SNR enables the imaging by a factor of N times faster, or alternatively allows imaging at the same speed with a source that has N times lower power. As a result, the exemplary embodiment of the present invention overcomes two important shortcomings of conventional LCI and OCT, e.g., source availability and scan speed. The factor N may reach more than 1,000, and allows construction of OFDI systems that can be more than three orders of magnitude improved from OCT and LCI technology currently in practice.

The gain in SNR is achieved because, e.g., the shot noise has a white noise spectrum. The signal intensity present at the detector at frequency ω (or wavelength λ) contributes only to the signal at frequency ω, but the shot noise is generated at all frequencies. By narrowing the optical band width per detector, the shot noise contribution at each frequency can be reduced, while the signal component remains the same.

Exemplary embodiments according to the present invention improves current data acquisition speeds and availability of sources compared with OCT. Shot noise is due to the statistical fluctuations of the current that are due to the quantized or discrete electric charges. The reduction of shot noise allows for much lower source powers or much higher acquisition rates. Limitations in current data acquisition rates (~4 frames/sec) are imposed by available source power and availability of fast mechanisms for scanning delay. An increase in the sensitivity of the detection by a factor of 8 would allow real time imaging at a speed of about 30 frames per second. An increase of the sensitivity by a factor of about 1,000-2,000 allows for the use of sources with much lower powers and higher spectral bandwidths which are readily available, cheaper to produce, and can generate higher resolution OFDI images.

For ophthalmic applications of OFDI, efficient detection preferably allows for a significant increase of acquisition speed. One limitation in ophthalmic applications is the power that is allowed to enter the eye according to the ANSI standards (approximately 700 microwatts at 830 nm). Current data acquisition speed in ophthalmic applications is approximately 100-500 A-lines per second. The power efficient detection technique of the present invention would allow for A-line acquisition rates on the order of about 100,000 A-lines per second, or video rate imaging at about 3,000 A-lines per image.

To achieve at least some of the goals of the present invention, an apparatus and method according an exemplary embodiment of the present invention are provided. In particular, at least one first electro-magnetic radiation may be provided to a sample and at least one second electro-magnetic radiation can be provided to a non-reflective reference. A frequency of the first and/or second radiations varies over time. An interference is detected between at least one third radiation associated with the first radiation and at least one fourth radiation associated with the second radiation. Alternatively, the first electro-magnetic radiation and/or second electro-magnetic radiation have a spectrum which changes over time. The spectrum may contain multiple frequencies at a particular time. In addition, it is possible to detect the interference signal between the third radiation and the fourth radiation in a first polarization state. Further, it may be preferable to detect a further interference signal between the third and fourth radiations in a second polarization state which is different from the first polarization state. The first and/or second electro-magnetic radiations may have a spectrum whose mean frequency changes substantially continuously over time at a tuning speed that is greater than 100 Tera Hertz per millisecond.

In one exemplary embodiment of the present invention, the third radiation may be a radiation returned from the sample, and the at least one fourth radiation is a radiation returned from the reference. The frequency of the first, second, third and/or fourth radiation may be shifted. An image can be generated based on the detected interference. A probe may be used which scans a transverse location of the sample to generate scanning data, and provides the scanning data to the third arrangement so as to generate the image. The scanning data may include the detected interference obtained at multiple transverse locations on the sample. At least one photodetector and at least one electrical filter may be used which follow a photodetector, which is followed by an electrical filter. The electric filter ma be a bandpass filter having a center frequency that is approximately the same as a magnitude of the frequency shift by the frequency shifting arrangement. A transmission profile of the electrical filter can vary substantially over its passband. The probe may include a rotary junction and a fiber-optic catheter. The catheter can be rotated at a speed higher than 30 revolutions per second. At least one polarization modulator may be provided.

At least one polarization diverse receive and/or a polarization diverse and dual balanced receiver may be used. It is further possible to track the phase difference between:
 the first electromagnetic radiation and the second electromagnetic radiation, and/or
 the third electromagnetic radiation and the fourth electromagnetic radiation.

According to still another exemplary embodiment of the present invention, the first and second electro-magnetic radiations can be emitted, at least one of which has a spectrum whose mean frequency changes substantially continuously over time at a tuning speed that is greater than 100 Tera Hertz per millisecond.

According to still a further exemplary embodiment of the present invention, an apparatus is provided. Such apparatus includes at least one first arrangement providing at least one first electro-magnetic radiation to a sample and at least one second electro-magnetic radiation to a reference. The apparatus also includes t least one second arrangement adapted for shifting the frequency of the first electro-magnetic radiation and the second electromagnetic radiation, and an interferometer interfering the first and second electro-magnetic radiations to produce an interference signal. Further, the apparatus includes > at least one second arrangement detecting the interference between the first and second electro-magnetic radiations.

Further, according to another exemplary embodiment of the present invention, a system, method, software arrangement and storage medium are provided for determining particular data associated with at least one of a structure and composition of a tissue. In particular, information associated with an interferometric signal is received which is formed from at least one first electro-magnetic radiation obtained from a sample and at least one second electro-magnetic radiation obtained from a reference. The first and/or second electro-magnetic radiations is/are frequency-shifted. The information is sampled to generate sampled data in a first format. Further, the sampled data is transformed into the particular data that is in a second format, the first and second format being different from one another.

BRIEF DESCRIPTION OF THE DRAWINGS

For a more complete understanding of the present invention and its advantages, reference is now made to the following description, taken in conjunction with the accompanying drawings, in which:

FIG. 3A is a block diagram of a system which performs frequency-domain imaging using a coherent single-frequency tuning source according to one exemplary embodiment of the present invention;

FIGS. 3B and 3C are graphs of wavelength versus amplitude which taken together illustrate the occurrence of a frequency shift generated by the system of FIG. 3A;

FIG. 3D is a graph of a beat signal generated by the system of FIG. 3A;

FIG. 4A is a block diagram of a system which performs frequency-domain imaging using a multiple-longitudinal-mode wavelength-swept source according to another exemplary embodiment of the present invention;

FIGS. 4B and 4C are graphs of a wavelength spectrum which taken together illustrate the occurrence of a shift in the spectrum generated by the system of FIG. 4A;

FIG. 4D is a graph of a beat signal generated by the system of FIG. 4A;

FIG. 8A is an exemplary graph of a laser output spectrum as measured at an output of the wavelength-swept laser arrangement of FIG. 7;

FIG. 8B is an exemplary graph of a laser output as measured at an output of the wavelength-swept laser of FIG. 7;

FIGS. 14A-14C are flow diagrams which illustrate an exemplary technique for a phase tracker operation according to the present invention;

FIG. 15 is a simplified diagram of the OFDI system according to another exemplary embodiment of the present invention;

FIGS. 16(a) and 16(b) are graphs of effects of a frequency shift according to the present invention, i.e., depth versus signal frequency;

FIGS. 18(a) and 18(c) are graphs of point spread functions measured without a mapping process according to the present invention;

FIGS. 18(b) and 18(d) are graphs of point spread functions measured with the mapping process according to the present invention; and FIGS. 19A and 19B are exemplary illustrations of images and/or graphs of experimental results obtained using exemplary embodiments of the present invention.

Figure 1:
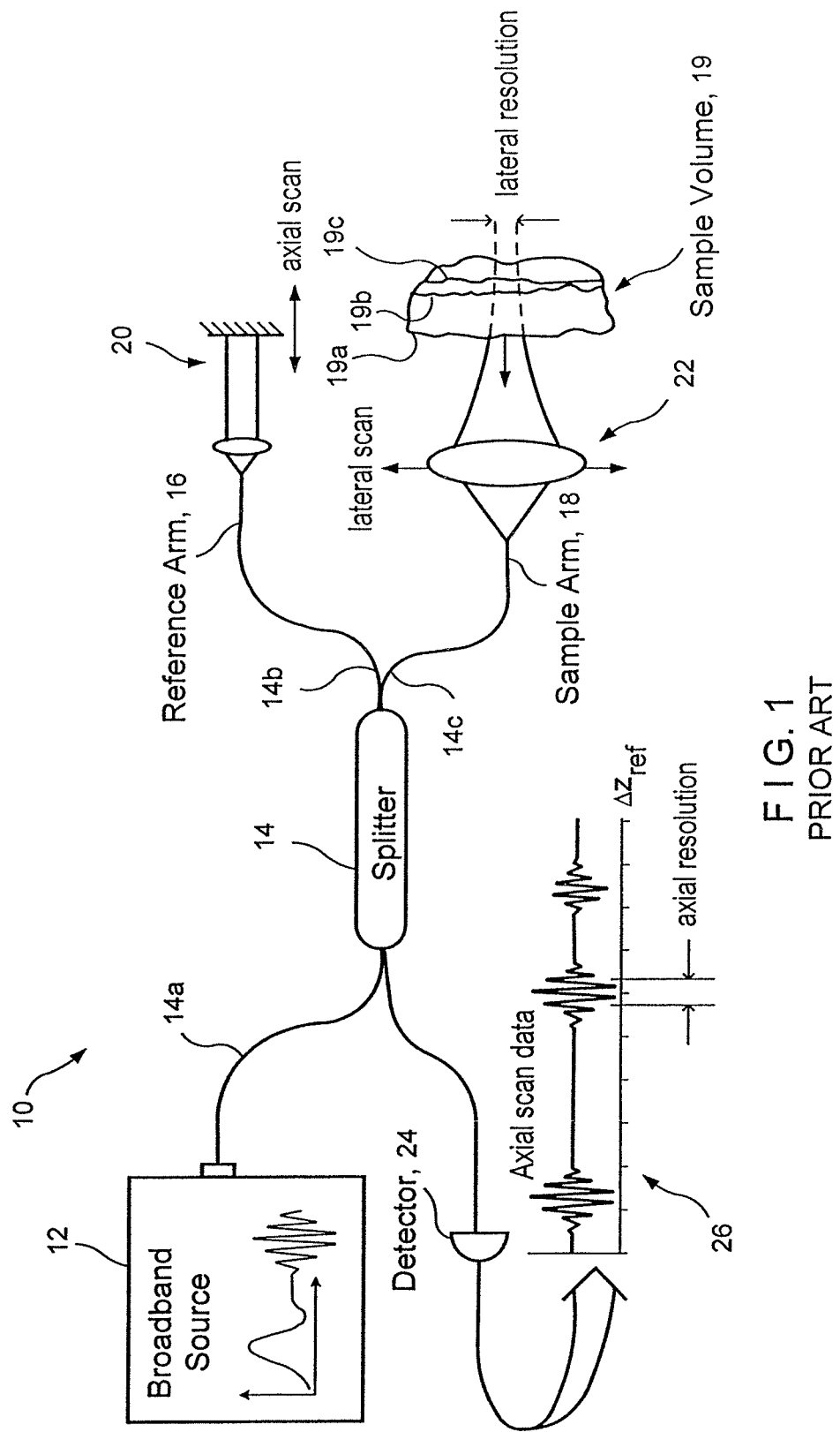
FIG. 1 is a block diagram of a time-domain optical coherence tomography ("OCT") system.

Throughout the drawings, the same reference numerals and characters, unless otherwise stated, are used to denote like features, elements, components, or portions of the illustrated embodiments. Moreover, while the present invention will now be described in detail with reference to the Figures, it is done so in connection with the illustrative embodiments.

DETAILED DESCRIPTION

FIG. 1 shows an exemplary prior art time domain optical coherence tomography ("OCT") system 10 which includes a broadband source 12 that provides a signal to a first aim 14a of two-by-two splitter 14. The splitter divides the signal provided thereto at port 14a, and provides a first portion of the signal at a port 14b coupled to a reference arm 16. The splitter 14 also provides a second portion of the signal at a port 14c coupled to a sample arm 18.

The sample arm 18 terminates at a sample volume 19 and an arrangement 22 for providing a lateral scan of the sample volume is disposed in the sample arm 18 prior to the sample volume 19. The reference arm 16 terminates in an arrangement 20 for providing an axial scan. The arrangements 20 and 22 operate as is generally known in the art.

Signals reflected from the means 20 and sample volume 19 back along the reference and sample arms 16, 18 respectively, are coupled back into respective ports 14b, 14c of the splitter 14 and are coupled to a detector 24 which produces axial scan data 26 as is generally known. U.S. Pat. No. 6,341,036, the entire disclosure of which is incorporated herein by reference, describes systems similar to the one described above and shown in FIG. 1.

In general, on scanning the reference arm path length 16, interference fringes are formed corresponding to positions that match the distance to the three structures 19a, 19b, 19c in the sample volume 19. The single detector 24 is used to detect the interference fringes. By envelope detection of the fringe patterns, an image 26 is constructed that maps tissue reflectivity to a given location.

As will be apparent from certain exemplary embodiments described herein below, an exemplary embodiment of the present invention relates to a system which utilizes a detection principle based upon Spectral Radar concepts (further referred to as Spectral Domain OCT) and/or a hybrid method between Spectral Domain and Time Domain OCT that is preferably more sensitive than current state of the art Time Domain OCT, allowing a substantial increase in the acquisition speed to resolution ratio.

Analysis of the Signal to Noise Ratio ("SNR") in Time Domain OCT has been previously described in related publications. The interference fringe peak amplitude in time domain OCT is given by $$I_{peak} = \sqrt{P_{ref} P_{sample}}, \quad (1)$$

with $P_{ref}$, $P_{sample}$ the reference and sample arm power in Watts, respectively. In terms of electrical power at the detector, the signal in units [A$^2$] is defined as $$S = \eta^2 e^2 P_{ref} P_{sample}/E_v^2, \quad (2)$$

with $\eta$ the quantum efficiency, e the charge quantum and $E_v = hc/\lambda$ the photon energy. The reference and sample arm powers are given by the respective reflected spectral densities, $$P_{ref,sample} = \int S_{ref,sample}(\omega) d\omega. \quad (3)$$

Assuming that the reference and sample spectral densities are equal to the source spectral density $S(\omega)$, where the sample arm spectral density is attenuated by a large factor, i.e., $S_{ref}(\omega) = S(\omega)$, $S_{sample}(\omega) = \alpha S(\omega)$ with $\alpha \ll 1$, and inserting the above expression of reference and sample arm into the original definition of the signal gives, $$S = \eta^2 e^2 \alpha [\int S(\omega) d\omega]^2 / E_v^2. \quad (4)$$

Three contributions to the total noise of OCT signals are: (i) thermal noise, (ii) shot noise and (iii) relative intensity noise. Thermal noise is generated by the feedback resistor, shot noise is related to the finite nature of the charge quantum resulting in statistical fluctuations on the current, and relative intensity noise is related to the temporal fluctuations due to chaotic character of classical light sources. These three contributions to the noise density in units [A$^2$/Hz] are given by, $$N_{noise}(f) = \frac{4kT}{R_{fb}} + \frac{2\eta e^2 P_{ref}}{E_v} + 2\left(\frac{\eta e P_{ref}}{E_v}\right)^2 \tau_{coh}, \quad (5)$$

k is Boltzmann's constant, T the temperature in Kelvin, $R_{fb}$ the value of the feedback resistor, and $\tau_{coh}$ the coherence time of the source. Coherence time is related to the full spectral width at half maximum $\Delta\lambda$ of a Gaussian source by the following relation, $\tau_{coh} = \sqrt{2\ln 2/\pi} \lambda_0^2/(c\Delta\lambda)$. Shot noise limited detection is achieved when the second term in Eq. (5) dominates the other noise contributions.

The signal to noise ratio (SNR) is given by $$SNR = \frac{S}{N_{noise}(f) BW}, \quad (6)$$

with BW the signal bandwidth, and parameters S and $N_{noise}$(f) as described above.

Spectral Domain OCT Using a Spectrometer and CCD Array Detector

The best signal to noise performance of Time Domain OCT systems is obtained when the noise is shot noise limited. Shot noise can be reduced significantly by replacing the single element detector with a multi-element array detector. When the detection arm light is spectrally dispersed on the array detector, each element of the array detects a small wavelength fraction of the spectral width of the source. The shot noise is preferably reduced by a factor equal to the number of elements of the array. The principle of the signal to noise improvement is based on the white noise characteristic of shot noise and the observation that only electromagnetic waves of the same wavelength produce interference fringes.

The shot noise power density $N_{noise}$(f) (in units [W/Hz], [A$^2$/Hz] or [V$^2$/Hz]) is proportional to the current (or equivalently the optical power times the quantum efficiency) generated in the detector. For a monochromatic beam of wavelength $\lambda_1$ entering the interferometer, the fringe frequency or carrier f at the detector is determined by the velocity v of the mirror, $f_1 = 2v/\lambda_1$. The shot noise is proportional to the power (or spectral density $S(\omega)$) at wavelength $\lambda_1$. A second wavelength $\lambda_2$ is preferably coupled into the interferometer. A second fringe frequency or carrier at frequency $f_2 = 2v/\lambda_2$ is simultaneously present. The shot noise at this second frequency is preferably the sum of the shot noise generated by the optical power at wavelength $\lambda_1$ and $\lambda_2$. Also, at frequency $f_1$ the shot noise is the sum of the shot noise generated by the optical power at wavelength $\lambda_1$ and $\lambda_2$. Thus, at both frequencies a cross-shot noise term is generated by the simultaneous presence of both wavelengths at the detector. By spectrally dispersing each wavelength to a separate detector, the cross shot noise term can be eliminated. In this way, Spectral Domain OCT offers a significant improvement of signal to noise ratio over Time Domain OCT systems.

The OCT signal is most easily described in the space domain. For a single object in the sample arm, the interference term of the OCT signal is proportional to the real part of the Fourier transform of the source spectrum $S(\omega)$, $$I(\Delta z) \propto \text{Re} \int \exp(ik\Delta z) S(k) dk, \quad (7)$$

with $\Delta z$ the path length difference between sample and reference arm and k the wave vector. As a function of time, the OCT signal is given by, $$I(t) \propto \text{Re} \int \exp(2i\omega rv/c) S(\omega) d\omega, \quad (8)$$

with v the reference arm mirror velocity. The frequency spectrum of the signal is given by a Fourier transform of the signal in the time domain, resulting in a complex function. The absolute value of this function is equal to the spectral density, $$|I(f)| = |\int I(t) e^{2i\pi ft} dt| = S(\pi f c/v), \quad (9)$$

which shows that the signal bandwidth is directly proportional to the source spectral width and scales linearly with the reference arm mirror velocity, i.e., imaging speed. Eq. (9) also preferably directly relates the absolute value of the frequency spectrum, |I(f)| to the signal S (see Eq. (4)). Eq. (9) also demonstrates that each angular frequency of the light source or equivalently each wavelength of the source is represented at its own frequency in the measured interferometric signal. The depth profile information I(t) can be obtained from the complex cross spectral density, |I(f)| by a Fourier transform.

The complex cross spectral density can also be obtained by splitting the signal I(t) in several spectral bands using a dispersive or interferometric element. At each detector, only part of the complex cross spectral density is determined. Combining the cross spectral densities of each detector, the full spectral density of the signal are retrieved. Thus, the same information can be obtained by separating spectral components to individual detectors. Combining the signal of all detectors in software or hardware would result in the same signal as obtained with a single detector.

In the detection arm, the spectrum can be split into two equal halves, where two detectors each detect one half of the spectrum. According to Eq. (9), the frequency spectra at detectors 1 and 2 are given by $|I_1(f)|=S(\pi fc/v)$ for $f<f_0$, $I_1(f)=0$ for $f>f_0$ and $I_2(f)=0$ for $f<f_0$, $|I_2(f)|=S(\pi fc/v)$ for $f>f_0$, respectively. The frequency spectrum as would be acquired by a single detector in time domain OCT is given by the sum of $I_1(f)$ and $I_2(f)$; $I(f)=I_1(f)+I_2(f)$. Thus, the signal S after combining the spectra is equal, however $I_1(f)=0$ for $f>f_0$ and $I_2(f)=0$ for $f<f_0$, the bandwidth BW per detector can be reduced by a factor of 2.

The noise is determined by the sum of the shot noise contributions at detectors one and two. From Eqs. (5) and (6), the shot noise per detector is proportional to the reference arm power at the detector times the bandwidth for the detector. Since the spectrum was split in equal halves, the reference power at detectors 1 and 2 is, respectively, $$P_{ref}^1=0.5P_{ref}, P_{ref}^2=0.5P_{ref} \quad (10)$$

The sum of the shot noise contribution for the two detectors is, $$N_{noise}^{SD} \propto P_{ref}^1 \times 0.5BW + P_{ref}^2 \times 0.5BW = 0.5P_{ref}BW, \quad (11)$$

which may compared with the shot noise of a single detector in time domain OCT, $$N_{noise}^{TD} \propto P_{ref}BW. \quad (12)$$

Thus, by spectrally dispersing the detection and light over two separate detectors, the signal remains the same, while the noise is reduced by a factor of 2, resulting in a net SNR gain by a factor of 2.

Extending the above analysis, it can be demonstrated that the shot noise contribution is reduced by a factor equal to the number of detectors. The sum of shot noises for N detector elements, where each detector element receives one Nth of the total reference power, is given $$N_{noise} = \frac{2\eta e^2 P_{ref}}{E_v} \frac{BW}{N}. \quad (13)$$

The signal is the same as in Time Domain OCT, and the SNR ratio for Spectral Domain OCT is given by, $$\frac{S}{N_{noise}} = \frac{\eta P_{sample} N}{2 E_v BW}. \quad (14)$$

Thus Spectral Domain OCT enables a SNR improvement over Time Domain OCT of a hundred to a thousand fold, depending on the number of detector elements N. Using a charge coupled array or an integrating device as a detector, such as, but not limited to, a line scan camera, the ratio N/BCW is replaced by the integration time $\tau_i$ of the array, which results in, $$\frac{S}{N_{noise}} = \frac{\eta P_{sample} \tau_i}{2 E_v}. \quad (15)$$

Figure 2:
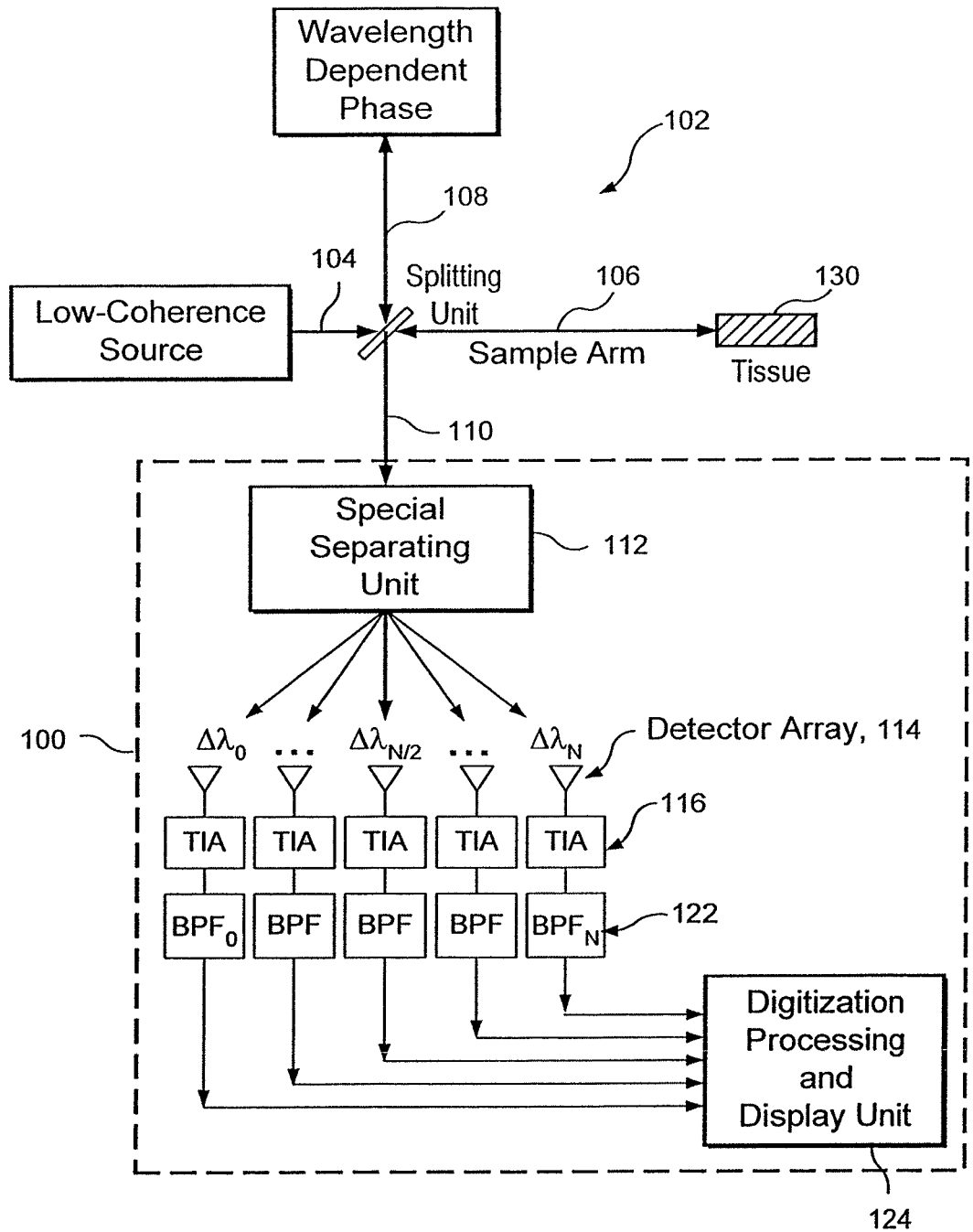
FIG. 2 is a block diagram of a system which performs frequency-domain imaging using a spectral radar technique.

FIG. 2 shows an exemplary Spectral Domain OCT system 100 which includes an interferometer 102 with a source arm 104, a sample arm 106, a reference arm 108, and a detection arm 110 with a spectral separating unit 112, a detector array 114 comprised of a plurality of detectors and a like plurality of amplifiers 116. The amplifiers 116 are coupled through optional analog processing electronics (not shown, but known to those having ordinary skill in the art), and A/D converters (not shown, but known to those skilled in the art) for conversion of signals and through digital band pass filtering ("BPF") units 122 to a processing and display unit 124.

The processing and display unit 124 executes data processing and display techniques, and can optionally include the digital band pass filtering ("BPF") units 122 as well as Digital Fast Fourier Transforms ("DFFTs") circuits (not shown), in order to provide coherent combination of signals and to perform the data processing and display functions. The detector array 114 may be 1×N for simple intensity ranging and imaging and/or Doppler sensitive detection, 2×N for dual balanced detection, 2×N for simple intensity ranging and/or polarization and/or Doppler sensitive detection, or 4×N for combined dual balanced and polarization and/or Doppler sensitive detection. Alternatively, an M×N array may be used for arbitrary number "M" of detectors 114 to allow detection of transverse spatial information on the sample 130.

Electro-magnetic radiation (e.g., light) is transmitted from the source along the source arm 104 to the splitting unit via and is split between the reference arm 108 and the sample arm 106. The light propagates along the sample arm to the tissue sample 130 and through the reference arm 108 to a wavelength dependent phase arrangement. The light is reflected from the sample and the wavelength dependent phase arrangement back toward the splitting unit where at least portions of the reflected light are directed toward the spectral separating unit 112 (which may be provided as a grating for example). The detection arm light is dispersed by the spectral separating unit 112 and the spectrum is imaged onto the detector array 114. By stepping the reference arm 108 length over a distance λ/8, the cross spectral density of reference arm 108 and sample arm 106 light can be determined. The processing and display unit received the signals fed thereto and performs a Fourier transform of the cross spectral density to generate depth profile information.

FIG. 3A shows a block diagram of an exemplary system according to the present invention which illustrates basic principles of a coherent frequency modulated continuous Wave ("C-FMCW") system using a single-frequency tuning source. A monochromatic laser light 70 operable as a frequency chirped laser provides a light signal to an input 72a of a coupler 72. The coupler 72 divides the light signal into a reference arm 80 which terminates in a reference mirror 82 and a sample arm 84 which terminates in a sample 86. The light propagates down paths 80, 84 and reflects from the reference mirror 82 and sample mirror 86 to provide, via coupler 72, interference signals which are detected by a photo-detector 88.

As shown in graphs of FIGS. 3B-3D, when there is an optical delay between two reflected light signals 90 (FIG. 3B) and 92 (FIG. 3C), respectively, a beat signal 94 (see FIG. 3D) having a frequency f may be detected at the photo detector 88. Where there are multiple reflection points in the sample along the axis, the interference consists of beat notes having frequencies which are proportional to the optical delay difference between the reflection (scatter) point in the sample and the reference mirror. The power of each beat frequency component is proportional to the reflectivity of the scatter. Therefore, the image of the sample can be constructed by Fourier transform of the interference data.

Referring now to FIGS. 4A-4D, in which like elements described above and shown in FIGS. 3A-3D are provided having the same reference designations, an optical frequency domain imaging ("OFDI") system according to an exemplary embodiment of the present invention includes a wavelength-swept laser source 95 (also referred to herein as a frequency swept source 95) which provides a laser output spectrum comprised of multiple longitudinal modes to an input of a coupler 72. The coupler 72 divides the signal fed thereto into the reference arm 80 which terminates in the reference mirror 82 and the sample arm 84 which terminates in the sample 86. The optical signals reflect from the reference mirror 82 and the sample 86 to provide, via coupler 72, a spectrum of signals which are detected by a photo-detector 88.

The center (or mean) wavelength of the signal spectrum is tuned in time by the creation of new longitudinal modes at the leading side of the spectrum and the annihilation of the modes at the trailing side of the spectrum.

The same principles described above with reference to FIGS. 3A-3D also apply to the OFDI technique using a wavelength-swept laser source 95. Similar to the case of a C-FMCW system (e.g., the system of FIG. 3A described above), a beat signal 94 can be produced. In the case of the OFDI system that uses a wavelength-swept laser source, the beat signal 94 can be generated having a beat frequency f which corresponds to the difference in the center frequency of the lights, 96 and 98, from the reference and sample, respectively.

The frequency spacing between longitudinal modes should be substantially larger than the detection bandwidth. The mode beat frequency (relative intensity noise peaks) can be removed by a proper electronic filter, such as low pass filter, prior to digitization. The interference signal 94 contains a frequency component that is proportional to the optical delay. Furthermore, the image of the sample can be constructed by Fourier transform of the digitized interference data.

In one exemplary embodiment of the present invention, the wavelength-swept laser 95 can be provided which utilizes an optical band-pass scanning filter in the laser cavity to produce a rapidly-swept multiple-frequency-mode output. Exemplary filters according to the present invention is described below in conjunction with FIGS. 6 and 9A. By using an optical band-pass scanning filter in the laser cavity, it is not necessary to tune the laser cavity length to provide synchronous tuning of the laser spectrum. Indeed, such arrangement does not require tuning the longitudinal cavity mode of the laser at the same rate as the center wavelength of the laser.

Using the OFDI techniques, a single pixel of the image can be constructed from the signal that is recorded as a function of time over the duration of one A-scan through Fourier transform. This is different from the TD OCT where a single pixel is constructed from the data measured at a short period time within one A-scan. The detection bandwidth to acquire the same number of data within the same A-scan period is approximately the same for both TD and FD OCT. However, the Fourier transform used for the OFDI technique effectively improves the signal-to-noise ratio compared to TD OCT by constructing a single image pixel from many data points acquired over the whole A-scan period. This effect can result in an "effective" detection bandwidth that is N-times larger than the actual detection bandwidth. Therefore, the SNR may be improved by N times, where N is the number of (digitized) data points in the Fourier transform. It can be shown that SNR in a shot noise limited case is given by:

$$\frac{S}{N_{noise}} = \frac{\eta P_{sample} N}{2 E_v BW} \quad (16)$$

Due to the narrowband output spectrum of the wavelength-swept source, however, the relative intensity noise (RIN) can be significantly higher than that of a CW broadband light source. For a thermal light, RIN is given by $1/\Delta v$ where $\Delta v = c \cdot \Delta\lambda / \lambda^2$ is the optical bandwidth of the (instantaneous) source output. For a laser light, RIN results from different statistics and therefore has a different value than the thermal light. For FD-OCT, a wavelength-swept laser with a low RIN level is preferred. The laser light with multiple longitudinal modes may have a similar RIN level as the thermal light with the same linewidth. In this case, a means to suppress the RIN is critical to have sufficient SNR, such as the dual balanced detection.

Use of a swept source results in a system having reduced shot noise and other forms of noise which allows for much lower source powers, or much higher acquisition rates than current systems. The increased detection sensitivity allows for real time imaging. Such imaging speed can assist with a problem of motion artifacts, such as in gastrointestinal, ophthalmic and arterial imaging environments. By increasing the frame rate while maintaining or improving the signal to noise ratio such artifacts can be minimized. The present invention also enables one to screen large areas of tissues with the OFDI technique, and allows clinical viable screening protocols using this method.

For ophthalmic applications of OFDI, the efficient detection preferably allows for a significant increase of acquisition speed. A possible limitation in ophthalmic applications is the power that is allowed to enter the eye according to the ANSI standards (approximately 700 microwatts at 830 nm). Current data acquisition speed in ophthalmic applications is approximately 100-500 A-lines per second. The power efficient detection would allow for A-line acquisition rates on the order of about 100,000 A-lines per second, or video rate imaging at about 3,000 A-lines per image.

The gain in SNR is achieved because the shot noise has a white noise spectrum. The signal intensity present at the detector at frequency ω (or wavelength λ) contributes only to the signal at frequency ω, but the shot noise is generated at all frequencies. By narrowing the optical band width per detector, the shot noise contribution at each frequency can be reduced, while the signal component remains the same.

Figure 5:
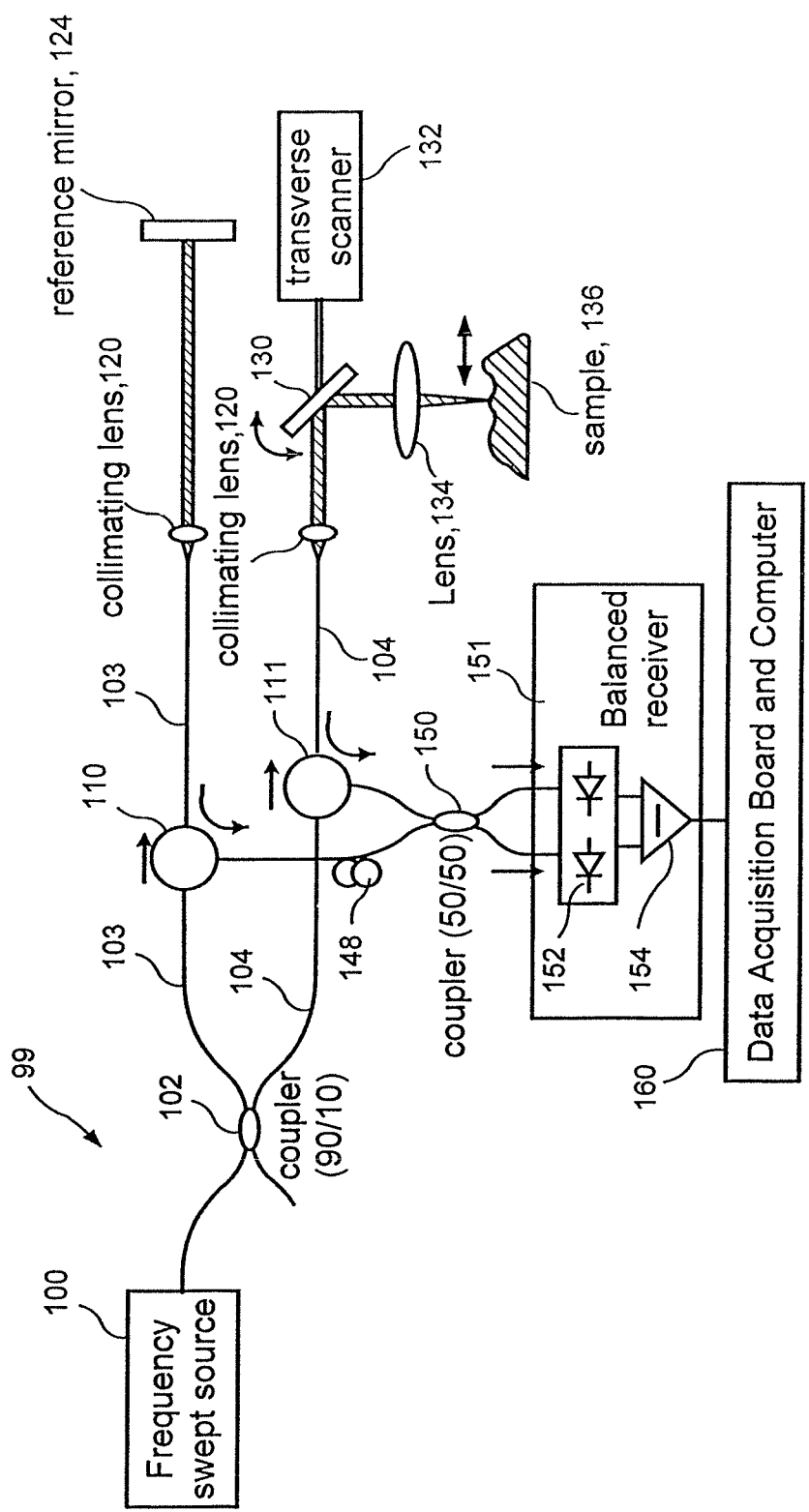
FIG. 5 is a block diagram of a system which performs frequency-domain imaging using a wavelength-swept source according to another exemplary embodiment of the present invention.

FIG. 5 shows an exemplary embodiment of a system 99 for performing optical imaging using frequency-domain interferometry ("OFDI") which includes a frequency swept source 100 that emits a narrowband spectrum of which the center wavelength is tuned continuously and repeatedly in time across the bandwidth of the gain medium in the source. The instantaneous emission spectrum consists of a plurality of frequency modes of the light source. The frequency swept source 100, may be provided in a variety of different ways, some of which are described below. The source 100 may, for example, be provided from various gain media, tunable wavelength filters, cavity configurations. Devices and methods are known in the art to provide a rapidly-tuned wavelength-swept laser source, such as solid-state lasers, active-ion-doped waveguide lasers, and fiber lasers. A wavelength-swept laser in a mode-locked regime can also be used with potential advantage of a lower relative intensity noise (RIN) in a frequency region between harmonics of longitudinal-mode beat frequencies. An optical saturable absorber may be incorporated inside a laser cavity or after the output port of the source to lower RIN level.

The light provided from swept source 100 is directed toward a fiber-optic coupler 102 which divides the light fed thereto into a reference arm 103 and a sample arm 104. In this exemplary embodiment, the coupler 102 has a 90:10 power splitting ratio with 90% of the power being directed toward the sample arm. Those of ordinary skill in the art would understand, however, that other coupling ratios for the coupler 102 may also be used. The particular coupling ratio to use in any particular application should be selected such that an amount of power is provided to both the reference aim and the sample arm to allow for proper operation of the exemplary system according to the present invention.

The power provided to the sample arm passes though a circulator 111, and illuminates a sample 136 to be imaged through a transverse-scanning imaging probe. The reference arm provides preferably a fixed optical delay. The lights reflected from a reference mirror 124 and from within the sample 136 can be directed through the respective circulators 110, 111 toward a fiber-optic beam splitter (or fused coupler) 150 and interfere between each other to produce interference signals.

It is desirable that the combining coupler 150 have an equal splitting ratio with minimal polarization dependence and wavelength dependence over the wavelength tuning range of the source. A deviation from equal splitting results in reduction of common mode rejection ratio ("CMRR") of the dual balanced detection. In one embodiment, the combining coupler 150 is preferably provided as a bulk broadband beam splitter. Those of ordinary skill in the art would understand that other types of couplers (including but not limited to wavelength-flattened fiber fused couplers) may also be used.

The interference signals are received by a dual balanced receiver 151. Output of the receiver 151 is provided to a computing arrangement (e.g., a data acquisition board and computer 160), such that the output is digitized and processed by the computer arrangement to produce an image. The data acquisition, transverse scanning, and wavelength tuning are synchronously controlled.

Figure 6:
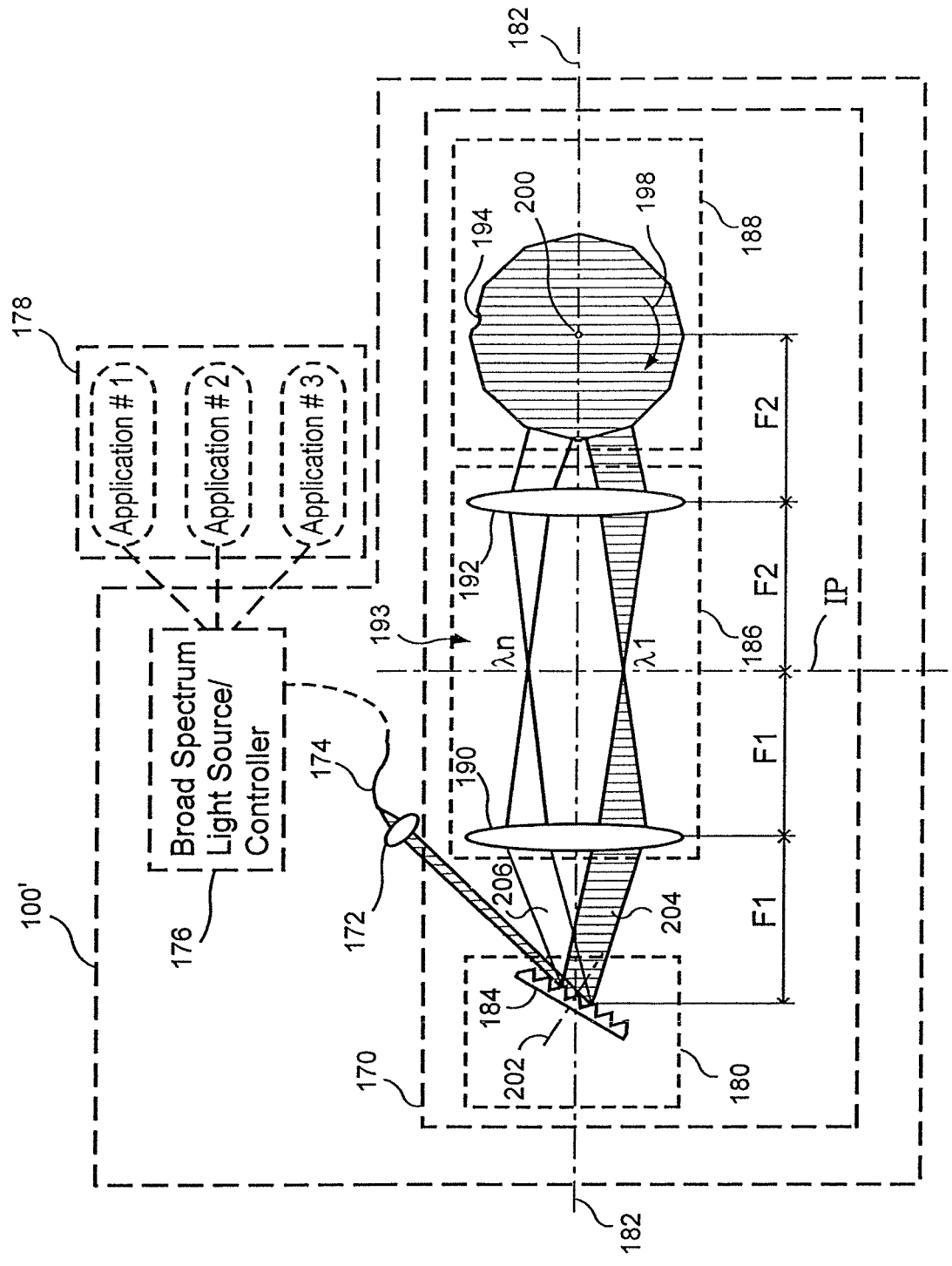
FIG. 6 is a block diagram of an optical wavelength tunable filter arrangement according to an exemplary embodiment of the present invention.

FIG. 6 shows an exemplary light source 100' which may, for example, be adapted for use as a frequency swept source (such as frequency swept source 100 described above with reference to FIG. 5) is provided from an optical filter 170, coupled through a lens 172 and a light path 174 to a light source/controller 176 (hereinafter referred to as "light controller 176"). The light controller 176 may, in turn, be coupled to one or more applications 178. The applications 178 may, for example, correspond to optical imaging processes and/or optical imaging systems, laser machining processes and systems, photolithography and photolithographic systems, laser topography systems, telecommunications processes and systems. Thus, the exemplary light source 100' provided from the filter 170 and the light controller 176 may be used in a wide variety of different applications, certain general examples of which are described herein.

As shall be described in further detail below, the filter 170 allows the light source 100' to operate as a frequency swept source which emits a spectrum of which the center wavelength can be tuned continuously and repeatedly in time across the bandwidth of the light controller 176. Thus, light source 100' may have an instantaneous emission spectrum comprised of a plurality of frequency modes of the light source/controller 176. In this exemplary embodiment, the optical wavelength filter 170 is configured as a reflection-type filter in that the input and output ports are identical. Thus, light path 174 may be provided, for example, as an input/output optical fiber and lens 172 may correspond to a collimating lens. Although the filter 170 in FIG. 6 is shown coupled to one or all of applications 178 through the light controller 176, it is possible to directly couple the filter 170 to one or more of the applications 178. Alternatively, it is possible to couple the filter 170 to one or more of the applications 178 through a device other than a light controller.

In the exemplary embodiment according to the present invention, the light controller 176 can include a number of systems that are specifically adapted to transmit a beam of light (in one embodiment, a collimated beam of light) having a broad frequency (f) spectrum. In particular, the beam of light can include a plurality of wavelengths, within the visible light spectrum (e.g., red, blue, green). The beam of light provided by the light controller can also include a plurality of wavelengths that are defined outside of the visible spectrum (e.g., infrared).

As shall be described in greater detail below with reference to FIG. 7, in one exemplary embodiment of the present invention, the light controller 176 can include a unidirectional light transmission ring. In another exemplary embodiment to be described in detail in conjunction with FIG. 9 below, the light controller 176 can include a linear resonator system. The filter 170 includes a wavelength dispersing element 180 adapted to receive the beam of light from the light controller 176 and to separate the beam of light into a plurality of different wavelengths of light each directed along a light path as is known. The wavelength dispersing element 180 can include one or more elements adapted to receive the beam of light from the light controller 176, and to separate the beam of light into a plurality of wavelengths of light each directed along a light path. The wavelength dispersing element 180 is further operative to direct the plurality of wavelengths of light in a plurality of angular directions or displacements with respect to an optical axis 182. In one exemplary embodiment of the present invention, the wavelength dispersing element 180 can include a light dispersion element, such as a reflection grating 184. The wavelength dispersing element 180 could alternatively be provided as a transmission grating (e.g. a transmission type grating such as Dickson-type holographic grating), a prism, a diffraction grating, an acousto-optic diffraction cell or combinations of one or more of these elements.

The wavelength dispersing element 180 directs light at each wavelength towards a lens system 186 along paths which are at an angle with respect to the optical axis 182. Each angle is determined by the wavelength dispersing element 180. The lens system 186 can include one or more optical elements adapted to receive the separated wavelengths of light from the wavelength dispersing element 180 and to direct or steer and/or focus the wavelengths of light to a predetermined position located on a beam deflection device 188. The beam deflection device 188 can be controlled to receive and selectively redirect one or more discrete wavelengths of light back along the optical axis 182 through the lens system 186 to the wavelength dispersing element 180 and back to the light controller 176. Thereafter, the light controller 176 can selectively direct the received discrete wavelengths of light to anyone or more of the applications 178. The beam deflecting device 188 can be formed and/or arranged in a number of ways. For example, the beam deflecting device 188 can be provided from elements including, but not limited to, a polygonal mirror, a planar minor disposed on a rotating shaft, a minor disposed on a galvanometer, or an acousto-optic modulator.

In the exemplary embodiment shown in FIG. 6, the dispersing element 186 includes a diffraction grating 184, a lens system 186 (which has first and second lenses 190, 192 to form a telescope 193), and the beam deflecting device 188 which is shown as a polygon mirror scanner 194. The telescope 193 is provided from the first and second lenses 190, 192 with 4-f configuration. The first and second lenses 190, 192 of the telescope 193 are each substantially centered on the optical axis 182. The first lens 190 is located at a first distance from the wavelength dispensing element 180 (e.g., diffraction grating 184), which is approximately equal to the focal length F1 of the first lens 190. The second lens 192 is located a second distance from the first lens 190, which is approximately equal to the sum of the focal length F1 of the first lens 190 and the focal length F2 of the second lens 192. In this exemplary arrangement, the first lens 190 can receive the collimated discrete wavelengths of light from the wavelength dispersing element 180, and may effectively perform a Fourier Transform on each one of the collimated one or more discrete wavelengths of light to provide an equal one or more converging beams projected onto an image plane (see designated IP of FIG. 6). The image plane IP is located between the first and second lenses and at a predetermined distance from the first lens, which predetermined distance is defined by the focal length F1 of the first lens. After propagating through the image plane IP, the converging beam(s) form an equal one or more diverging beams that are received by the second lens. The second lens operates to receive the one or more diverging beams and to provide an equal number of collimated beams having predetermined angular displacements with respect to the optical axis 182 for directing or steering the collimated beams to predefined portions of the beam deflection device 188.

The telescope 193 is configured to provide a number of features, as described above, and further to convert diverging angular dispersion from the grating into converging angular dispersion after the second lens 192, which is desired for proper operation of the filter 170. In addition, the telescope 193 provides a useful degree of freedom, which controls the tuning range and reduces the beam size at the polygon mirror 194 to avoid a beam clipping.

As is illustrated in FIG. 6, the polygon mirror 194 reflects back preferably only the spectral component within a narrow passband as a function of the angle of the front mirror facet of the polygon with respect to the optic axis. The reflected narrowband light is diffracted and received by the optical fiber 174.

The orientation of the incident beam with respect to the optic axis and the rotation direction 198 of the polygon mirror 194 determine the direction of wavelength tuning: wavelength up (positive) scan or down (negative) scan. The arrangement in FIG. 6 produces a positive wavelength sweep. It should be understood that while the mirror 194 is shown in FIG. 6 as having twelve facets, fewer or more than twelve facets can also be used. The particular number of facets to use in any application depends upon the desired scanning rate and scanning range for a particular application. Furthermore, the size of the mirror is selected in accordance with the needs of a particular application taking into account factors including, but not limited to, manufacturability and weight of the mirror 194. It should also be appreciated that lenses 190, 192 may be provided having different focal lengths. The lenses 190, 192 should be selected to provide a focal point at approximately the center point 200 of the mirror 194.

Consider a Gaussian beam with a broad optical spectrum incident to the grating from the fiber collimator 172. The well-known grating equation is expressed as $\lambda = p \cdot (\sin \alpha + \sin \beta)$ where $\lambda$ is the optical wavelength, p is the grating pitch, and $\alpha$ and $\beta$ are the incident and diffracted angles of the beam with respect to a nominal axis 202 of the grating, respectively. The center wavelength of tuning range of the filter is given by $\lambda_0 = p \cdot (\sin \alpha + \sin \beta_0)$ where $\lambda_0$ is the angle between the optic axis 38 of the telescope and the grating normal axis. It can be shown that FWHM bandwidth of the filter is given by $(\delta\lambda)_{FWHM}/\lambda_0 = A \cdot (p/m) \cos \alpha /W$ where $A = \sqrt{4\ln 2/\pi}$ for double pass, m is the diffraction order, and W is $1/e^2$-width of the Gaussian been at the fiber collimator. When the real part of the complex spectral density is determined, ranging depth z is defined by $$z = \frac{\lambda_0^2}{4(\delta\lambda)_{FWHM}}.$$

Tuning range of the filter is fundamentally limited by the finite numerical aperture of lens1 20. The acceptance angle of lens1 without beam clipping is given by $\Delta\beta = (D_1 - W \cos \beta_0 / \cos \alpha) / F_1$, where $D_1$ and $F_1$ are the diameter and focal length of lens1. It relates to the filter tuning range via $\Delta\lambda = p \cos \beta_0 \cdot \Delta\beta$. An importance design parameter of the filter, originated from multiple facet nature of the polygon mirror, is the free spectral range, which is described in the following. A spectral component after propagating through lens1 20 and lens2 22 will have a beam propagation axis at an angle $\beta'$ with respect to the optic axis 38: $\beta' = -(\beta - \beta_0) \cdot (F_1/F_2)$ where $F_1$ and $F_2$ are the focal lengths of lens1 and lens2, respectively. The polygon has a facet-to-facet polar angle given by $\theta = 2\pi/N \approx L/R$ where L is the facet width, R is the radius of the polygon, and N is the number of facets. If the range of $\beta'$ of incident spectrum is greater than the facet angle, i.e. $\Delta\beta' = \Delta\beta \cdot (F_1/F_2) > \theta$, the polygon minor could retro-reflect more than one spectral component at a given time. The spacing of the multiple spectral components simultaneously reflected, or the free spectral range, can be shown to be $(\Delta\lambda)_{FSR} = p \cos \beta_0 (F_2/F_1) \cdot \theta$.

In the application as an intracavity scanning filter, the tuning range of the laser cannot exceed the free spectral range if the gain medium has homogenous broadening, since the laser chooses the wavelength of highest gain. The duty cycle of laser tuning by the filter can be, in principle, 100% with no excess loss caused by beam clipping if two necessary conditions are met as follows:

$$W < \frac{\cos\alpha F_1}{\cos\beta_0 F_2} L \qquad (17)$$

and $$W < \frac{\cos\alpha}{\cos\beta_0} (F_2 - S) \cdot \theta$$

The first equation is derived from the condition that the beamwidth after lens 192 should be smaller than the facet width. The second equation is from that the two beams at the lowest and highest wavelengths 204, 206 respectively of the tuning range should not overlap each other at the polygon mirror S in Equation (1) denotes the distance between the lens 192 and the front mirror of the polygon.

In one experiment, optical components with the following parameters were selected: W=1.9 mm, p=1/1200 mm, $\alpha$=1.2 rad, $\beta_0$=0.71 rad, m=1, $D_1$=$D_2$=25 mm, $F_1$=100 mm, $F_2$=45 mm, N=24, R=25 mm, L=6.54, S=5 mm, $\theta$=0.26 rad, $\lambda_0$=1320 nm. From the parameters, the theoretical FWHM bandwidth, tuning range and free spectral range of the filter could be calculated: $(\delta\lambda)_{FWHM}$=0.09 nm, $\Delta\lambda$=126 nm and $(\Delta\lambda)_{FSR}$=74 nm. Both conditions in (1) are satisfied with margins. The characteristics of the filter were measured using broadband amplifier spontaneous emission light from a semiconductor optical amplifier (SOA) and an optical spectrum analyzer. The optical spectrum analyzer recorded the normalized throughput (reflected) spectrum in peak-hold mode while the polygon mirror was spinning at its maximum speed of 15.7 kHz. The measured tuning range was 90 nm which is substantially smaller than the theoretical value of 126 nm. The discrepancy was due to the aberration of the telescope, primarily field curvature, associated with relatively large angular divergence of the beam from the grating. It is expected that the aberration would be improved by using optimized lenses. The free spectral range was 73.5 nm in agreement with the theoretical calculation. The FWHM bandwidth was measured to be 0.12 nm. The discrepancy with theoretical limit of 0.11 nm may be reasonable considering the aberration and imperfection of the optical elements.

Figure 7:
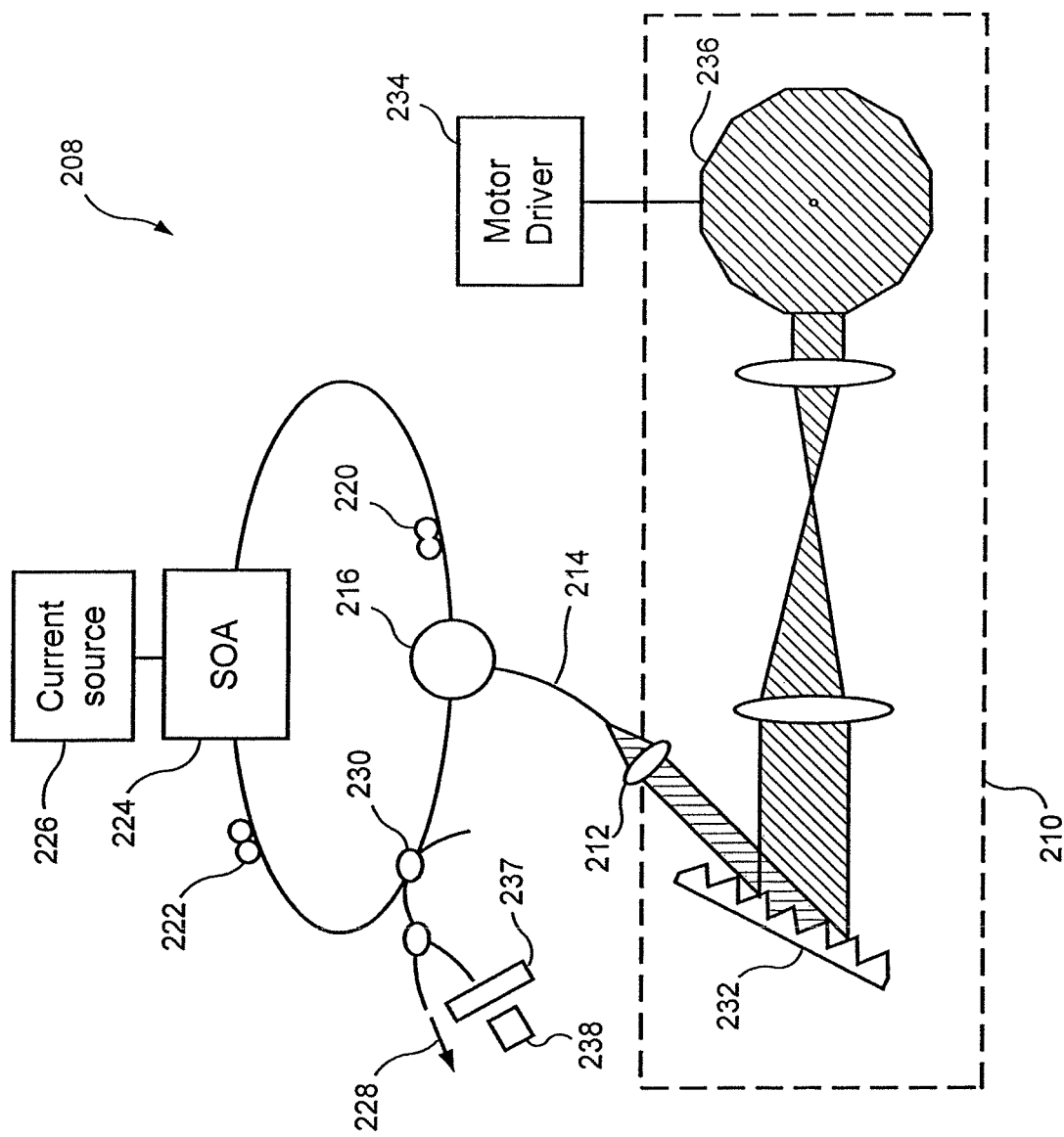
FIG. 7 is a block diagram of a wavelength-swept laser arrangement according to an exemplary embodiment of the present invention.

FIG. 7 shows an extended-cavity semiconductor laser 208 according to an exemplary embodiment of the present invention which can include a filter 210 that may, for example, be similar to the filter 170 described above with reference to FIG. 6. The filter 210 is coupled through a light directing element 212 and a light path 214 to a Faraday circulator 216. In this exemplary embodiment, the filter 210 includes a grating 232 and a polygonal mirror 236. Thus, the filter 210 may correspond to a polygon-based filter. A motor 234 drives the mirror.

The Faraday circulator 216 of this exemplary embodiment is coupled through polarization controllers 220, 222 to a gain medium 224 which in one exemplary embodiment can be a semiconductor optical amplifier (e.g., SOA, Philips, CQF 882/e) having coupled thereto a current source 226 which provides an injection current to the SOA 224. The intracavity elements may be connected by single-mode optical fibers, for example. The two polarization controllers 220, 222 can align the polarization states of the intracavity light to align to the axes of maximum efficiency of the grating 232 and of maximum gain of the SOA 224.

A laser output 228 may be obtained through a 90% port of a fiber-optic fused coupler 230. To generate a sync signal useful for potential applications, 5% of the laser output may be coupled through a variable wavelength filter 237 having a bandwidth of 0.12 nm and is directed toward a photodetector 238. In one exemplary embodiment, the center wavelength of the filter may be fixed at 1290 nm. The detector signal generates short pulses when the output wavelength of the laser is swept through the narrowband passband of the fixed-wavelength filter. The timing of the sync pulse is controlled by changing the center wavelength of the filter.

FIG. 8A shows a graph 240 of an output spectrum of a laser of the type described above with reference to FIG. 7 as measured by an optical spectrum analyzer in peak-hold mode, when the polygon mirror (i.e. mirror 236 in FIG. 7) spins at a rate of 15.7 kHz. The edge-to-edge sweep range may be from 1282 nm to 1355 nm over 73 nm-width equal to the free-spectral range of the filter. The Gaussian-like profile of the measured spectrum, rather than a square profile, is likely due to the polarization-dependent cavity loss caused by polarization sensitivity of the filter and the birefringence in the cavity. It is preferable to adjust the polarization controllers to obtain the maximum sweep range and output power.

FIG. 8B shows a curve 242 of a laser output in a time domain. The upper trace 244 corresponds to a sync signal obtained through the fixed-wavelength filter. The amplitude of power variation from facet to facet was less than 3.5%. The peak and average output power was 9 mW and 6 mW, respectively. It should be mentioned that the y-axis scale of curve 240 had to be calibrated from the time-domain measurement, because the optical spectrum analyzer only recorded a time-averaged spectrum due to the laser tuning speed much faster than the sweep speed of the spectrum analyzer.

A frequency downshift in the optical spectrum of the intracavity laser light may arise as the light passes through an SOA gain medium (e.g. SOA 224 in FIG. 7), as a result of intraband four-wave mixing phenomenon. In the presence of the frequency downshift, the positive wavelength scan can facilitate tuning of the laser spectrum, and thereby produce higher output powers. The peak power of the laser output can be measured as a function of the tuning speed. The negative tuning speed may be obtained by flipping the position of the collimator and the orientation of the grating with respect to an optic axis (e.g., axis 182 in FIG. 6). It is preferable to make the physical parameters of the filter approximately identical in both tuning directions. Thus, the combined action of self-frequency shift and positive tuning allows higher output to be obtained and enables the laser to be operated at higher tuning speed. Therefore, the positive wavelength scan may be the preferred operation. The output power may decrease with increasing tuning speed. Thus, a short cavity length may be desired to reduce the sensitivity of the output power to the tuning speed. In this case, a free-space laser cavity is preferred.

Figure 9A:
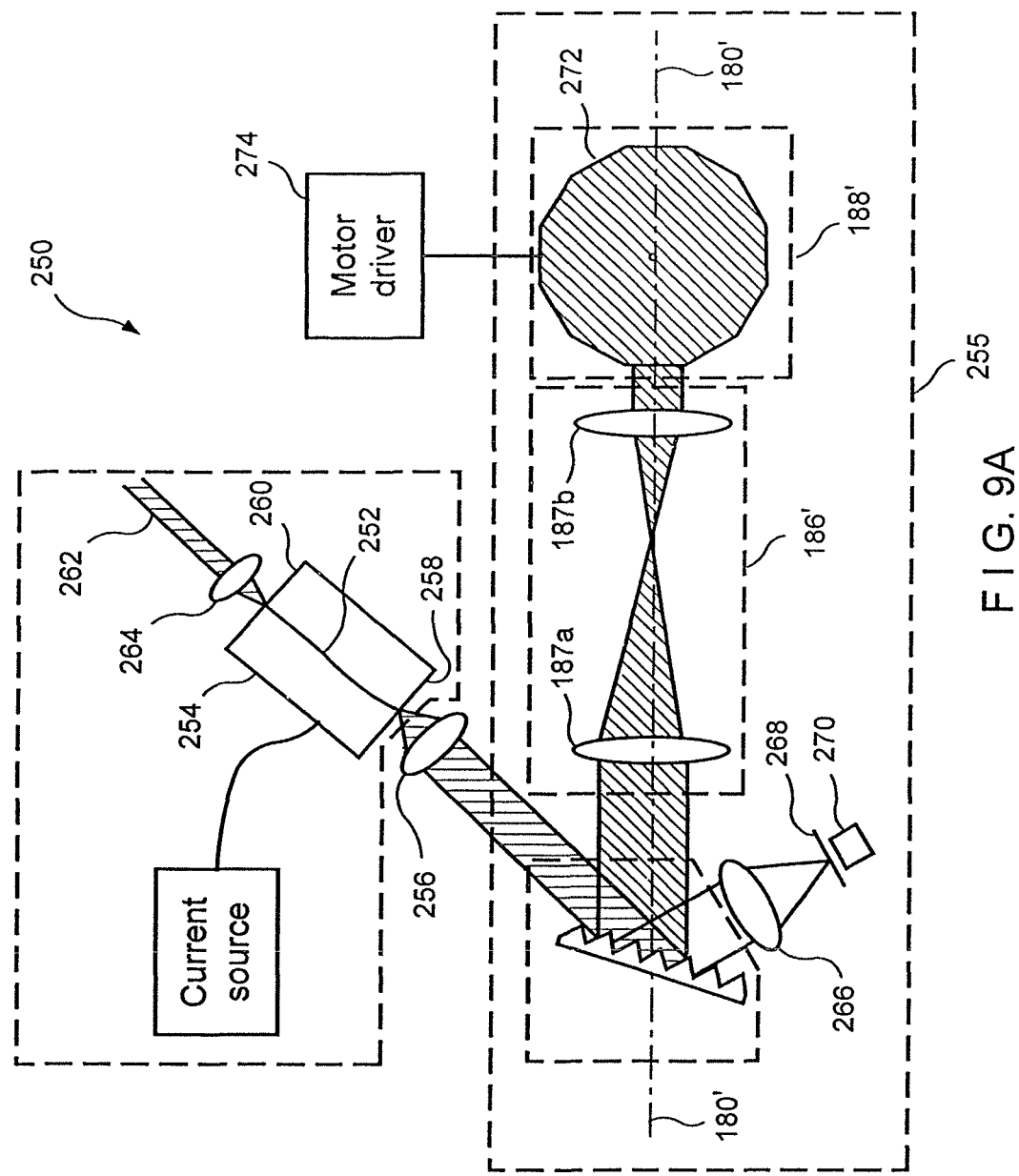
FIG. 9A is a block diagram of a wavelength tunable filter arrangement bearing a polygonal mirror according to yet another exemplary embodiment of the present invention.

FIG. 9A shows an exemplary embodiment of a free-space extended-cavity semiconductor tunable laser 250 according to an exemplary embodiment of the present invention that includes a semiconductor waveguide 252 fabricated on a substrate chip 254 coupled to a polygon scanning filter 255 through a collimating lens 256. A front facet 258 may be anti-reflection coated, and an output facet 260 is cleaved or preferably coated with dielectrics to have an optimal reflectivity. An output 262 of the laser is obtained through the output coupling lens 264. The collimating lenses 256, 264 are preferably provided as aspheric lenses.

The filter 255 includes a wavelength dispersing element 180' adapted to receive the beam directed thereto from the lens 256. The wavelength dispersing element 180' may be similar to wavelength dispersing element 180 described above with reference to FIG. 6. A lens system 186' can be disposed between the wavelength dispersing element 180' and a beam deflection device 188'. The wavelength dispersing element 180' and a beam deflection device 188' may be similar to wavelength dispersing element 180 and a beam deflection device 188 described above with reference to FIG. 6. The lens systems 186' includes a pair of lenses 187a, 187b which are preferably provided as achromats having low aberration particularly in field curvature and coma.

A sync output may be obtained by using a lens 266, a pinhole 268, and a photodetector 270 positioned on the 0-th order diffraction path for the light which is on retro-reflection from a polygon scanner 272. The detector generates a short pulse when the focus of the optical beam of a particular wavelength sweeps through the pinhole 268. Other types of gain medium may include, but are not limited to, rare-earth-ion doped fiber, Ti:$Al_2O_3$, and $Cr^{4+}$:forsterite.

Figure 9B:
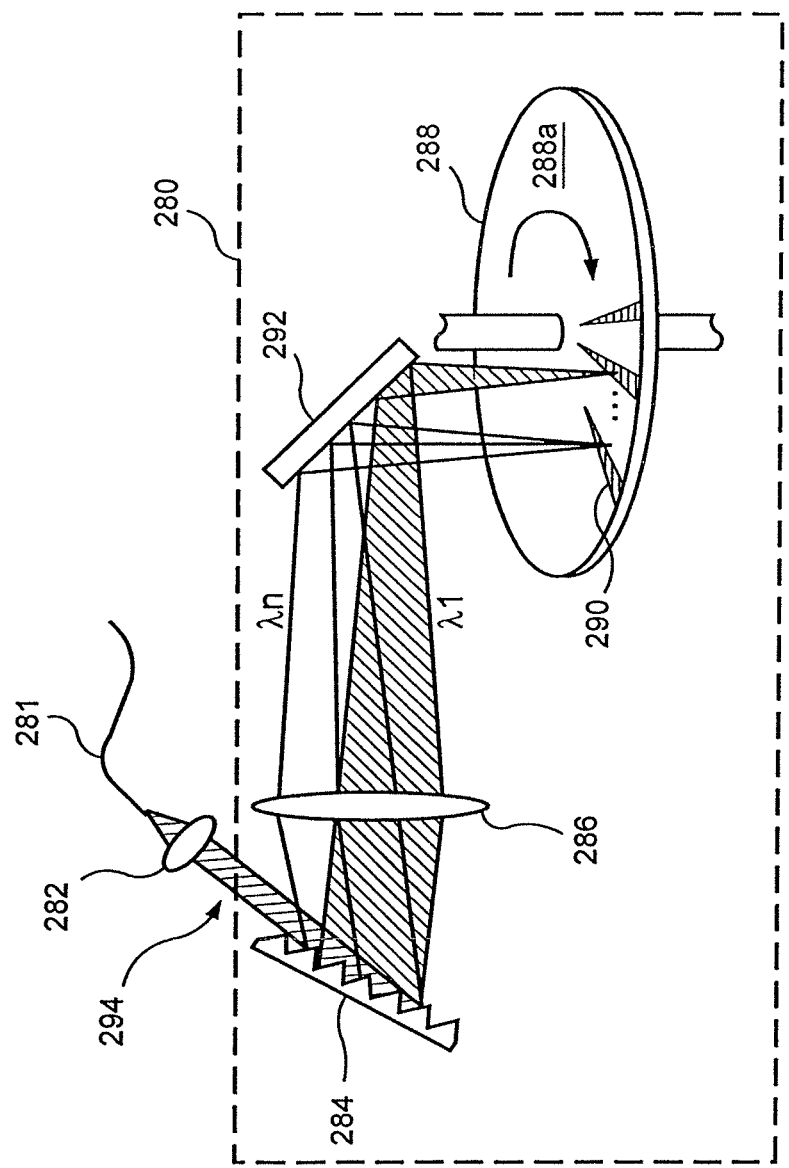
FIG. 9B is a block diagram of a wavelength tunable filter arrangement having reflective disk according to still another exemplary embodiment of the present invention.

FIG. 9B, shows another exemplary embodiment of a wavelength tunable filter 280 according to the present invention which may include an optical fiber 281 coupled to an input collimating lens 282, optically coupled to a diffraction grating 284, a focusing lens 286, and a spinning disk 288. The diffraction grating 284 may be replaced by other angular dispersive elements such as a prism. In one exemplary embodiment, the diffraction grating 284 can have a concave curvature with a focal length selected such the focusing lens 286 is not needed.

Preferably more than one reflector 290 may be deposited on a surface 288a of the spinning disk 288. Preferably, the reflectors 290 comprise multiple narrow stripes periodically and radially patterned. The material for the reflectors is preferably gold. The disk 288 can be composed of a lightweight plastic or silicon substrate. Instead of the reflectors deposited on the top surface of the disk, the disk can have a series of through holes followed by a single reflector attached to the back surface of the disk. Incident from the optical fiber 281, the optical beams of different wavelengths may be illuminated on the surface of the disk into a line after being diffracted by the grating and focused by the lens 286 (in those systems which include lens 286). Preferably, only the beam that impacts the reflectors of the spinning disk may be retro-reflected and received by the optical fiber 281. A mirror 292 may be used to facilitate the access of the beam onto the disk.

The distance from the lens 286 to the reflectors of the disk 288 is equal to the focal length, F, of the lens. It can be shown from the grating equation that the tuning range of the filter is given by $\Delta\lambda = p \cos \beta_0 (D/F)$ where D denotes the distance between the stripes. The width of the strip, w, is preferably made to be substantially equal to the beam spot size $w_s$, at the surface of the disk:

$$w_s = W \frac{\cos\beta_0}{\cos\alpha} \cdot \frac{F/z}{\sqrt{1+(f/z)^2}}$$

where $z = \pi w_s^2/\lambda$. It leads to a FWHM filter bandwidth given by $(\delta\lambda)_{FWHM}/\lambda_0 = A \cdot (p/m) \cos \alpha/W$ where $A = \sqrt{4\ln 2}/\pi$. For the $w > w_s$, filter bandwidth becomes greater, and for $w < w_s$, the efficiency (reflectivity) of the filter is decreased by beam clipping. The orientation of an incident beam 294 with respect to the optic axis of the lens 286 and the spinning direction 288 preferably determines the sense of wavelength tuning. The positive wavelength scan is preferable, which is achieved by spinning the disk 288 in a clockwise direction as shown in FIG. 9B.

a. Interferometer

Figure 10A:
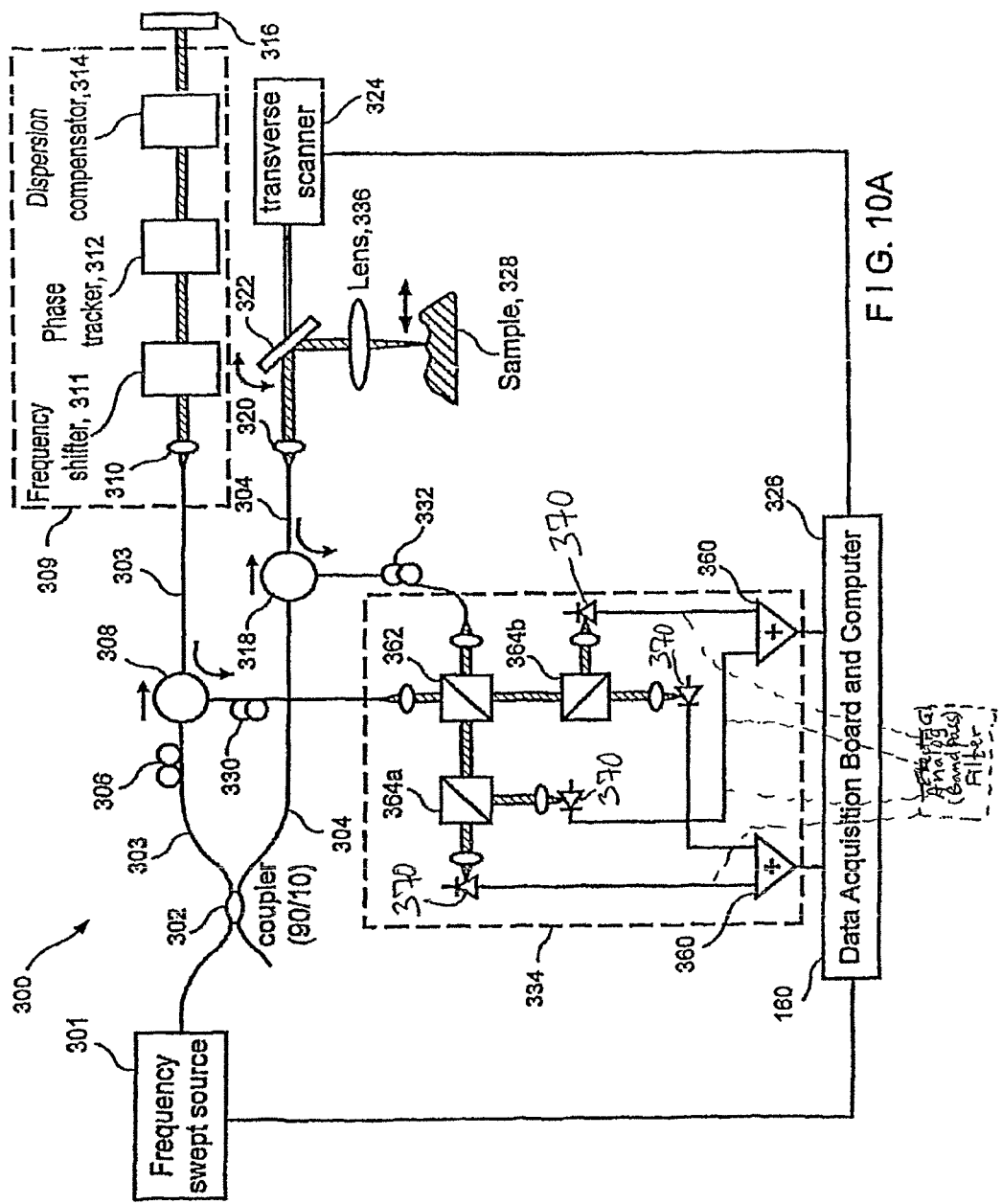
FIG. 10A is a block diagram of an optical frequency domain imaging ("OFDI") system which includes a wavelength-swept laser and a polarization diversity-balanced detection ("PDBD") circuit according to a further exemplary embodiment of the present invention.

FIG. 10A shows an exemplary embodiment of an OFDI system 300 according to the present invention for performing optical imaging using frequency-domain interferometry includes a frequency swept source 301 which emits a light signal having an instantaneous emission spectrum comprised of a plurality of frequency modes of the light source. Source 301 may, for example, be provided as one of the sources described above with reference to FIGS. 4A, 5, 6, 7, 9 and 9B. The light from source 301 can be directed toward a fiber-optic coupler 302 which divides the light fed thereto into a reference arm 303 and a sample arm 304.

The reference arm 303 preferably includes a polarization circuit 306 and a circulator 308. Thus, light propagates from source 301 through the coupler 302, the polarization circuit 306 and the circulator 308 to an optional motion artifact circuit 309. The optional motion artifact circuit 309 may be provided from a lens 310 which directs the light toward a frequency shifter 311, a phase tracker 312 and a dispersion compensator 314. The light passes through optional circuit 309 and is incident upon a reference mirror 316. It should be appreciated that circuit 309 functions to remove or reduce motion artifacts. It should also be appreciated that circuit 309 may include all of the elements 310-314, and/or one or more of the circuit elements 310-314.

The sample arm 304 may include a circulator 318. Thus, a light signal transmitted from the source 301 propagates from source 301 through the coupler 302 and the circulator 308 to a lens 320 which directs the light toward a scanning mirror 322. The scanning mirror 322 may be provided from a wide variety of optical elements including but not limited to, a galvanometer, a piezoelectric actuator or another functionally equivalent device. A transverse scanner 324 is coupled to the scanning mirror 322 and a data acquisition board and computer 326. The data acquisition board and computer 326 is also coupled to the frequency swept source 301.

The OFDI system 300 shown in FIG. 10A can also include a polarization diversity balanced detection ("PDBD") circuit 334 configured to receive signals from the reference arm 303 and/or the sample arm 304. In particular, the reference arm 303 is connected through circulator 308 and polarization control circuit 330 to a reference port of the PDBD circuit 334. Similarly, sample arm 304 is connected through circulator 318 and polarization control circuit 332 to a sample port of the PDBD circuit 334.

b. Interferometer

The sample arm 304 collects light reflected from a tissue sample 328 and is combined with the light from the reference arm 303 in the polarization diversity balanced detection (PDBD) circuit 334 to form interference fringes.

For example, the OFDI technique does not require that the optical path length in the reference arm be scanned in time. Thus, in certain exemplary embodiments of the present invention, it may be preferable to provide the reference arm as a fixed delay reference arm. Such fixed delay reference arms may have various configurations that are known to those having ordinary skill in the art.

The reference arm 303 can be either of reflective and/or transmission type, and can return light back from the mirror 316. The returned light is directed toward the polarization control circuit 330 via the circulator 308. Similarly, the reflected light from the sample 338 can be directed toward a polarization control circuit 332 via the circulator 318. The reference arm can also be transmission with no reflection. The polarization control circuit 330 can be used to match the polarization state of the reference-arm light to that of the sample-arm. The total birefringence in the interferometer should be minimized not to induce wavelength-dependent birefringence. The polarization controller may include, but is not limited to, a fiber-optic polarization controller based on bending-induced birefringence or squeezing.

Preferably, the chromatic dispersion should be matched substantially between the reference and sample arm. The result of strong dispersion mismatch may be a loss in the axial resolution. Any residual dispersion can likely be compensated by appropriate signal processing, such as nonlinear mapping based on interpolation of the detector data before the Fourier transform. This mapping may also be accomplished, at least in part, by adjusting the optical layout of the wavelength-swept source. In one example in which the source 301 includes a polygon scanner and a telescope, the distance between the polygon scanner and the telescope can be adjusted to convert wavelength space to wave vector space prior to Fourier transformation.

c. Sample Arm

For certain OFDI applications, the sample arm may be terminated by an optical probe comprising a cleaved (angled, flat, or polished) optical fiber or free space beam. A lens 336 (such as, but not limited to, aspherical, gradient index, spherical, diffractive, ball, drum or the like) may be used to focus the beam on or within the sample. Beam directing elements (such as, but not limited to, mirror, prism, diffractive optical element or the like) may also be contained within the probe to direct the focused beam to a desired position on the sample. The position of the beam may be changed on the sample as a function of time, allowing reconstruction of a two-dimensional image. Altering the position of the focused beam on the sample may be accomplished by the scanning mirror 322. The scanning mirror 322 may be provided, for example, from a number of different devices including, but not limited to, a galvanometer, piezoelectric actuator, an electro-optic actuator or the like.

Figure 10B:
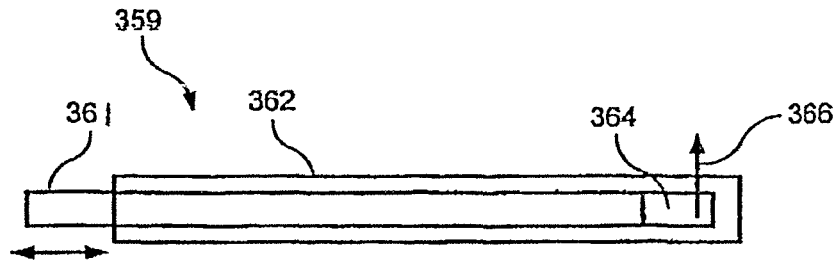
FIG. 10B is a block diagram of an exemplary probe arrangement shown in FIG. 10A.

The sample arm probe may be a fiber optic probe that has an internally moving element, such that the motion is initiated at a proximal end of the probe and the motion is conveyed by a motion transducing arrangement (such as, but not limited to, wire, guidewire, speedometer cable, spring, optical fiber and the like) to the distal end. The fiber optic probe may be enclosed in a stationary sheath which is optically transparent where the light exits the probe at the distal end. Thus, scanning way also be accomplished by moving the optical fiber. For example, by rotating the optical fiber, or linearly translating the optical fiber. FIG. 10B shows an exemplary embodiment of the probe 359 which includes an inner cable 361 (that may rotate or linearly translate along the axis of the probe), an outer transparent or semi-transparent sheath 362, distal optics 364, and remitted light 366 (which may be at any angle with respect to axis of catheter).

d. Detection

The PDBD circuit 334 may include a plurality of detectors 370 disposed to provide dual balanced detection. Dual balanced detection may be preferred in certain applications for the following reasons. First, most light sources generate 1/f noise (f=frequency) at relatively low frequencies and balanced detection will eliminate 1/f source noise. Second, an interference term of the sample arm light with itself (i.e. an auto-correlation term) can be present on top of the true signal term, which is preferably the interference between sample and reference arm. Such auto-correlation term can be eliminated by a differential technique and balanced detection may eliminate this auto-correlation term from the measured signal. Third, RIN can be reduced.

The detectors 370 may preferably include photodiodes (such as, but not limited to, silicon, InGaAs, extended InGaAs, and the like). Balanced detection can be implemented by subtracting diode signals that are exactly out of phase with respect to the maxima and minima pattern. The difference between two detector signals is obtained by a differential circuit included in PDBD circuit 334 and amplified by trans-impedance amplifiers ("TIA") 360. The dual balanced receiver may be further followed by a low-pass or band-pass filter to reject noise outside the detection bandwidth.

In this exemplary embodiment of the present invention, the dual balanced detection can be implemented as follows. The polarization beam splitter 362 receives signals from the reference and sample arms and provides two output signals. The two output signals are further split by two non-polarizing beam splitters 364a, 364b, respectively. The outputs from each beam splitter 364a, 364b are detected by a dual balanced receiver provided from the four detectors 370. Furthermore, the two outputs of the dual balanced receivers are digitized and processed in a computer arrangement to obtain a polarization diversity.

The receiver output is provided to circuit 326 which acquires and digitizes the signals fed thereto via A/D converters, and stores the digitized signals in a computer for further processing. The bandwidth of the TIA is preferably matched to half the sampling rate. Gain of the TIA is preferably selected such that the maximum receiver output range is matched to the voltage range of the A/D converter.

e. Processing

If more than two detectors are used, the signals can be selectively subtracted and complex spectral density can be obtained. Using the Fourier transform, the complex cross spectral density can be converted to a depth profile in the tissue. Several methods to process the complex spectral density to obtain depth profile information are known to those skilled in the art, such as, but not limited to, by obtaining at least two signals with a Pi/2 phase shift in the reference arm and then reconnecting the complex spectral density by some linear combination of the two signals, or by squaring the spectral density.

Following the detection, analog processing can include a trans-impedance amplifier, low pass (band pass) filter, and digitization of the signal. This signal may then be converted to reflectivity as a function of depth by the Fourier transform operation. Digital processing includes digitization, digital band pass filtering in either the frequency domain or time domain (FIR or IIR filter) and inverse Fourier transformation to recover the tissue reflectivity as a function of depth.

Prior to the Fourier transformation, the detected non-linear wavelength coordinates is preferably converted to regularly sampled wave-vector space. Typically zero padding the signal, Fourier transformation, and inverse Fourier transformation with re-sampling can be utilized for remapping. Other interpolation methods known in the art, such as linear, bi-linear, and cubic spline interpolation of the data may also be used to convert wavelength space into regularly sampled k space. This mapping may also be accomplished in part by adjusting the optical layout of the wavelength-swept source. In one example, the distance between the polygon scanner and the telescope may be adjusted to convert wavelength space to wavevector space prior to Fourier transformation.

Another exemplary embodiment of the present invention can utilize one or more techniques described below to further enhance the performance and functionality of imaging. These techniques are not limited to the OFDI techniques that use a multiple-frequency-mode tuned source, but can be applied in the OFDI technique using a single-frequency tuned source.

a. Polarization Diversity

For an application where polarization fading is a problem, a polarization diversity scheme may be used. Various configurations for polarization diversity are known in the art.

In the system shown in FIG. 10A, the polarization diversity circuit operates as follows. The polarization beam splitter 362 separates the reference-arm and sample-arm light signals depending upon their polarization states. The polarization controller 330 is preferably adjusted so that the reference-arm power is split with an equal magnitude by the polarization controller. The polarization state of the sample arm power can be assumed to vary randomly due to the probe or sample motion, therefore the separating ratio of the sample arm power by the polarization splitter can vary in time. However, the two output signals at the two output ports of the polarization beam splitter 362 can be detected by a photo receiver, e.g., squared and summed. The resulting signal is independent of the polarization state of the sample arm light.

b. Carrier-frequency Heterodyne Detection

The optical frequency shifter 311 may be situated in the reference arm 303 to shift the optical frequency for carrier-frequency heterodyne detection. As a result, the signal frequency band is shifted by the magnitude of the frequency shift. In this manner, relatively large 1/f noise (f=frequency) and RIN around DC can be avoided. The frequency shifter can be, but not limited to, an acousto-optic frequency shifter. In the detection, a proper electronics should be used to demodulate the carrier frequency.

Figure 10C:
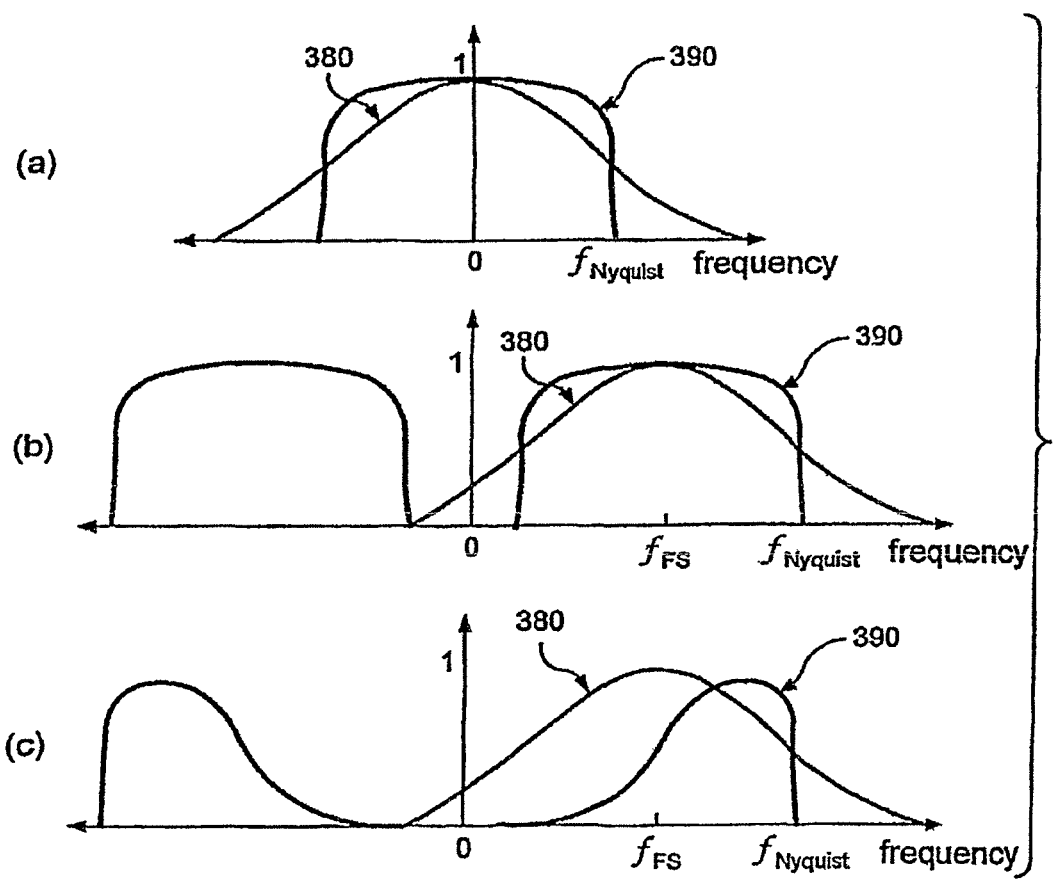
FIG. 10C is a plurality of graphs illustrating exemplary outputs of a carrier-frequency heterodyne detection using the system of FIG. 10A.

One of the benefits of using the frequency shifter 311 is that the effective ranging depth can be doubled. This can be illustrated in the electrical frequency domain, as shown in FIG. 10C in which a graph 380 depicts the fringe visibility curve given by the instantaneous output spectrum of the source. The visibility curve has a Gaussian profile if the source's instantaneous spectrum is Gaussian. A curve 390 depicts the transmission efficiency profile of an electrical filter, which is optimized for a given Nyquist frequency defined as the half of the sampling frequency. Section (a) of FIG. 10C shows a typical case where there is no frequency shifter in the interferometer and the electrical filter is a low pass filter. Because the positive and negative frequency band is not differentiable, the images associated with the positive and negative frequency band, respectively, are overlapped. Because of this ambiguity, only half of the frequency range (zero to $f_N$) or (zero to $-f_N$) is usable in this case. However, using a frequency shifter results in a shift of the visibility curve by $f_{FS}$, as shown in portion (b) of FIG. 10C. With a bandpass filter (or a low pass filter), both sides of the frequency band centered at $f_{FS}$ produce images without ambiguity, resulting in a twice larger ranging depth compared to section (a) of FIG. 10C.

Instead of a square-top bandpass filter, it is possible to use a slope filter. In an example shown in FIG. 10C section (c), the transmission efficiency curve of the filter, 390, has an exponentially-rising (falling) slope in its low frequency band. This filter may be useful in which attenuation is significant and the resulting signal strength decays with depth. The slope filter can improve the dynamic range of the detection by effectively suppressing the large signal from the surface relative to that at greater depths.

c. Reference Arm Delay (Phase Tracking and Auto-ranging)

As described above, the OFDI technique does not: require the optical path length in the reference arm to be scanned in time. A fixed-delay reference arm can be made in various configurations that are known to those having ordinary skill in the art. The reference arm can be of either reflective or transmission type.

In certain applications, the capability of varying the optical delay in the reference arm may be useful when a larger ranging depth is desired, without increasing the data acquisition rate or reducing the instantaneous linewidth of the optical source. Such ability is useful in a clinical study where the distance from the imaging lens and the front surface of the sample can varies significantly. Such variation can result from the motion or from the uncontrolled position of a probing catheter. For example, a rotating catheter inside a blood vessel can have distance variation by a couple of millimeter over a single A-scan.

A mechanism in the reference arm 303 may allow for scanning the group delay of the reference arm 303. This group delay can be produced by any of a number of techniques known to those having ordinary skill in the art, such as, but not limited to, stretching an optical fiber, free space translational scanning using a piezoelectric transducer, or via a grating based pulse shaping optical delay line. Preferably, the delay can be introduced by a non-mechanical or motionless arrangement. By the term "non-mechanical", what is meant is that there are no mechanically moving parts being utilized. The absence of the mechanically moving parts is believed to reduce the known deficiencies of using mechanical devices to introduce delay. In contrast to traditional LCI or OCT systems, the reference arm 303 according to an exemplary embodiment of the present invention does not necessarily need to scan over the full ranging depth in the sample, and can preferably scan over at least a fraction of the ranging depth equal to one over the number of detectors (1/N). This scanning feature is different from the conventional delay scanning schemes used in the known LCI and OCT systems. The reference arm 303 optionally has a phase modulator mechanism, such as but not limited to, an acoustooptic modulator, electro-optic phase modulator or the like, for generating a carrier frequency.

Phase tracking is preferable performed to eliminate phase instabilities in the interferometer. Phase instabilities can cause individual interferometric fringes to shift in location. If detection is slow relative to the shifting of the fringes, the resulting averaging results in chirping of the interference signal. A-scan rate of 10 to 40 kHz results in an effective integration time of 100 to 25 µs. Phase instabilities arising on a time frame shorter than the integration time should be compensated. Phase locking circuitry is commonly used in electronics, and is frequently used in radar and ultrasound. Active phase tracking can be implemented by modulating the interferometer path length difference at 10 MHz with an electro-optic phase modulator in the reference arm over a fraction of the wavelength. By demodulating the intensity measured by one detector at the output of the interferometer at the frequency of the path length modulation, an error signal can be generated indicating in which direction the phase modulator should shift to lock onto a fringe amplitude maximum. By adding an offset to the phase modulator as determined by the error signal, the phase tracker actively locks onto a fringe maximum.

The phase modulator can modulate the path length difference over a few wavelengths. The processing unit can determine if the phase modulator has reached its range limit, and jump by a full wave in phase to maintain lock on a different fringe maximum. This approach exploits the fact that phase should be controlled only modulo $2\pi$. In addition, the processing drives a slower component (e.g., the Rapid Scanning Optical Delay ("RSOD") line) to extend the path length range of the phase modulator/RSOD combination over several millimeters. Phase locking can be performed on a fringe maximum, minimum, or zero crossing, based on the type of mixing performed in the demodulation circuit.

Another exemplary embodiment of the present invention can also use autoranging techniques and technology, including processing techniques described in U.S. patent application publication no. 2002/0198457, the disclosure of which is hereby incorporated herein by reference in its entirety. The autoranging mechanism may, in one exemplary embodiment, include a processor unit for (a) obtaining a first scan line; (b) locating a surface location "S" of a sample; (c) locating an optimal scan range "R" of the sample; (d) modifying a reference arm delay waveform to provide an output; (e) outputting the output to a reference arm; (f) determining whether the image is complete; and/or (g) moving to the next scan line if the image is not complete or remapping the image using the surface S data and the waveform data stored in the memory storage device if the image is complete.

If the light signal returned from the sample has a low amplitude, phase locking may be unstable due to the presence of noise. In another exemplary embodiment of the present invention, a separate, preferably monochromatic, light source can be transmitted into the interferometer. The separate source wavelength may be within the wavelength tuning range of the OFDI source or may be centered at a different wavelength than the OFDI source spectrum. The separate source is preferably of higher power, and may be combined with the source arm (using wavelength division, multiplexer, grating, prism, filter or the like) travel to the reference and sample arms and return back to the beam recombining element. The returned separate source light can then be separated from the OFDI light following transmission back through the beam recombining element (i.e. beam splitter output). A separation arrangement can perform spectral separation by a dispersing element, such as a dichroic mirror, filter, grating, prism, wavelength division multiplexer or the like. The separate source will be detected separately from the OFDI light using one or more detectors. The higher power provided by this separate source can enable detection of a higher amplitude interference pattern, and provide an improved input to the phase tracker, thus enabling more stable phase tracking.

Figure 11:
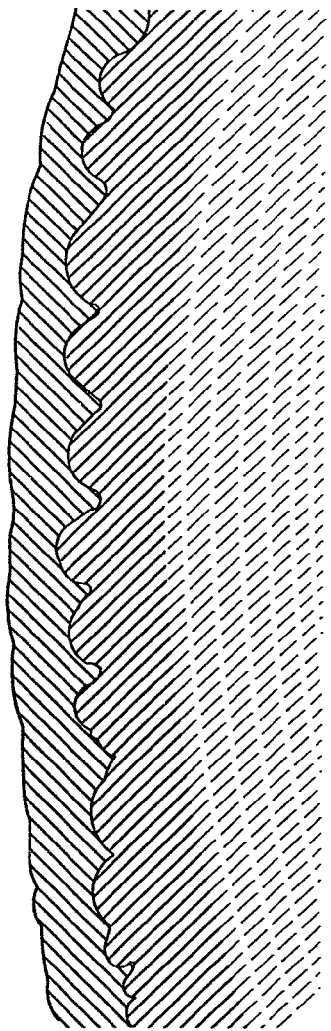
FIG. 11 is an exemplary in-vivo image of a human finger tip obtained using exemplary embodiments of the present invention.

Referring now to FIG. 11, an in vivo image of a subject's fingertip (300*500 pixels) acquired at an A-line scan rate of 15.7 kHz is shown using the exemplary embodiment of the system and process according to the present invention. The optical sensitivity was measured to be about −100 dB. The SNR is superior to an equivalent TD OCT of the same A-line scan rate. The vertical line noise arises due to an un-optimized detection when there is a strong mirror-like reflection from the surface of the tissue, but should preferably be eliminated substantially by a detection optimization and/or an appropriate signal processing.

Figure 12:
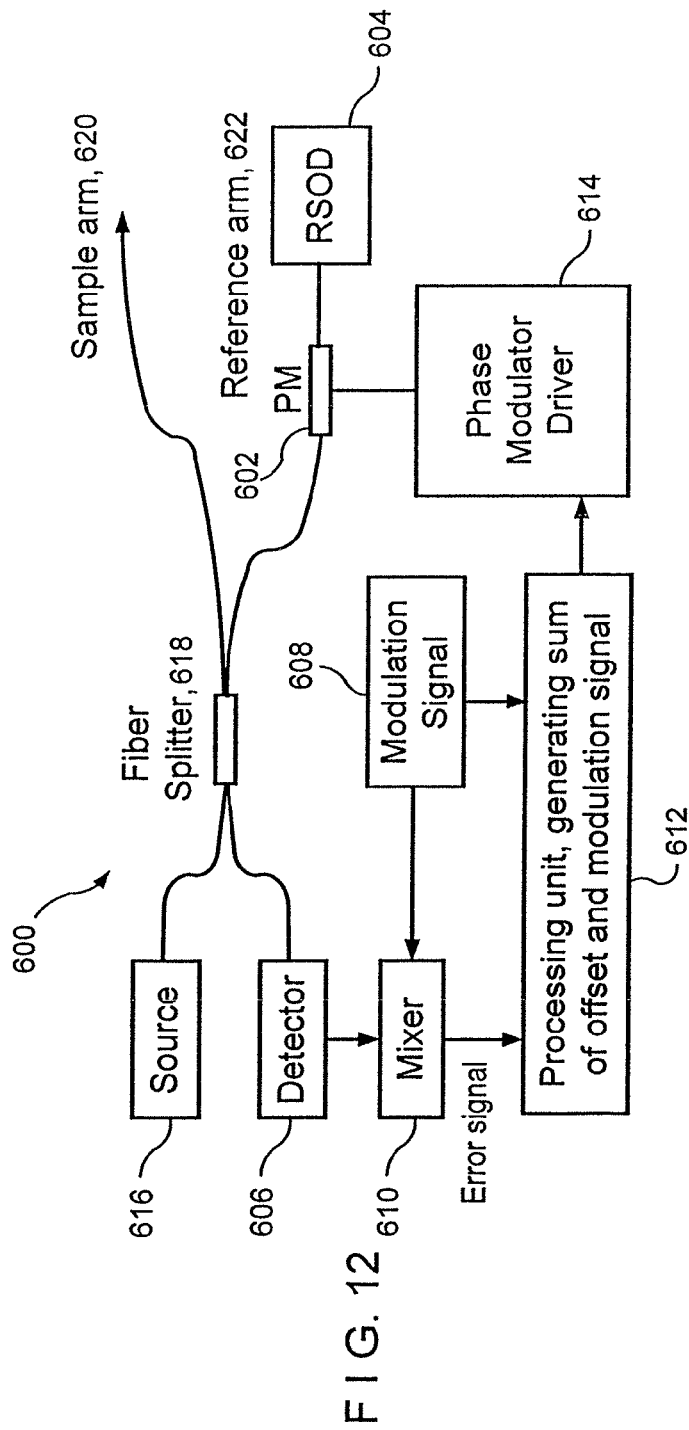
FIG. 12 is a block diagram of a phase tracker arrangement according to an exemplary embodiment of the present invention.

FIG. 12 shows another exemplary embodiment of a phase tracker system 600 according to the present invention having an extended phase lock range is provided. This done by combining a fast element 602 (which may be provided, for example, as an electro-optic (EO) phase modulator 602) to modulate the path length difference over a small range, and a slower element 604 (which may, for example, be provided as a Rapid Scanning Optical Delay (RSOD) line 604) to modulate the path length over an extended range. The detector 606 signal can be mixed with the phase modulator modulation frequency 608 by a mixer 610 and low pass filtered (filter not shown) to generate an error signal. The processing unit 612 preferably processes the error signal to generate an offset voltage, and adds this offset voltage to the modulation signal 608, so as to generate the output for the phase modulator driver 614. In addition, the processing unit 612 can generate a signal to the RSOD 604 to provide extended range tracking of the phase over distances of several millimeters. Light source 616, fiber splitter 618, sample arm 620 and reference arm 622 are shown, and are described herein.

The intensity I(t) at the detector at a given moment within a single oscillation of the fringe pattern is given by $I(t) = \cos[\phi(t)]$ where the phase φ gives the position in the fringe. For φ=0, the signal is at a fringe maximum, for φ=π, the signal is at a fringe minimum. At an arbitrary moment t, the phase φ(t) is given by, $\phi(t) = \alpha + \beta \sin(\omega t)$ where α describes the position within a single oscillation of the fringe pattern, and β*sin(ωt) is the phase modulation introduced by the phase modulator, with β the amplitude of the phase modulation, and ω the frequency of the phase modulation signal. The intensity at the photodetector I(t) can be mixed with a carrier at frequency ω and 2ω, resulting in the mixer signal MixerC(t), MixerS(t), Mixer2ωC(t) and Mixer2ωS(t), $\mathrm{Mixer}C(t) = \cos(\omega t) \cdot \cos(\alpha + \beta \sin(\omega t));$ $\mathrm{Mixer}S(t) = \sin(\omega t) \cdot \cos(\alpha + \beta \sin(\omega t));$ $\mathrm{Mixer}2\omega C(t) = \cos(2\omega t) \cdot \cos(\alpha + \beta \sin(\omega t)); \mathrm{Mixer}2\omega S(t) = \sin(2\omega t) \cdot \cos(\alpha + \beta \sin(\omega t))$ The time average over a single oscillation of the carrier frequency ω of MixerC, MixerS, Mixer2ωC and Mixer2ωS is given by, $\overline{\mathrm{MixerC}(t)} = 0$; $\overline{\mathrm{MixerS}(t)} = \sin(\alpha) \cdot J_1(\beta)$; $\overline{\mathrm{Mixer2\omega C}(t)} = \cos(\alpha) \cdot J_2(\beta)$; $\overline{\mathrm{Mixer2wS}(t)} = 0$, where $J_1(\beta)$ and $J_2(\beta)$ are a Bessel functions of the first kind; its value depends on β, the amplitude of the phase modulation. Thus, the signal $\overline{\mathrm{MixerS}(t)}$ and $\overline{\mathrm{Mixer2\omega C}(t)}$ are proportional to sin(α) and cos(α), respectively, with α the position within a single oscillation of the fringe pattern. The mixer outputs $\overline{\mathrm{MixerS}(t)}$ and Mixer2ωC(t) are used as an error signal to generate an offset voltage to steer the phase modulator to a new center position that minimizes the error signal, and locks the interferometer output on a fringe maximum or minimum, or a zero crossing, respectively. The complex spectral density can now be determined by two consecutive tuning scans, one where the error signal sin(α) is minimized, and the next where the error signal cos(α) is minimized, resulting in a 90 degrees phase shift between the two interference patterns. Using this mixing arrangement, the complex spectral density can be obtained rapidly and without resorting to an additional mechanical arrangement for changing the phase of the reference arm light.

Figure 13:
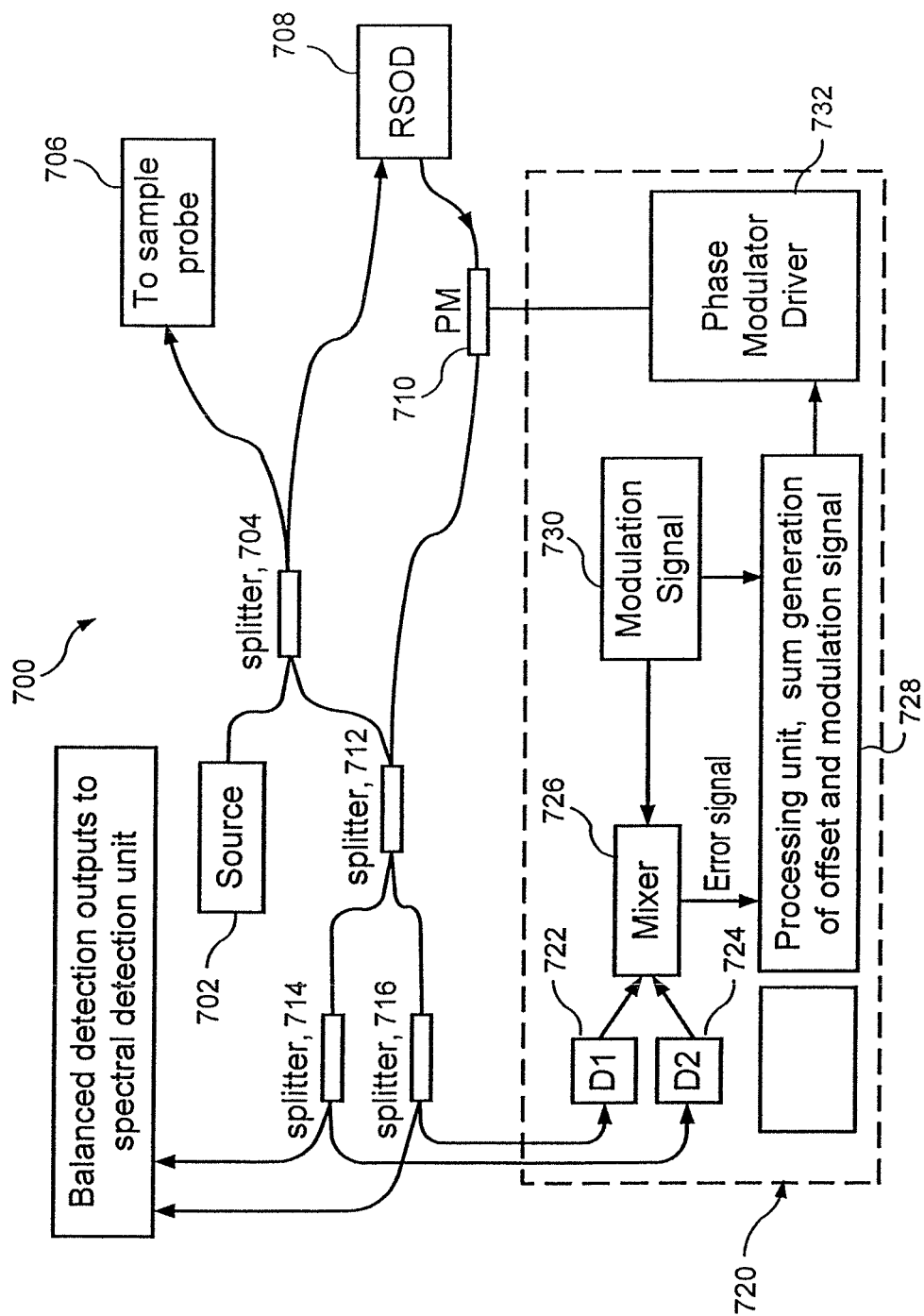
FIG. 13 is a block diagram of an exemplary embodiment of the OFDI system according to the present invention having the phase tracker.

FIG. 13 shows a further exemplary embodiment of an OFDI system 700 which includes a phase tracker for providing balanced detection according to the present invention. In this exemplary embodiment, a source 702 provides an electro-magnetic radiation (e.g., light) which passes through a splitter 704, that sends part of the light to a sample probe 706 and the remainder of the light to a Rapid Scanning Optical Delay ("RSOD") line 708. Light is passed from the RSOD 708 to the phase modulator PM 710. Light from the phase modulator PM 710 is transmitted through a splitter 712, and then through two additional splitters 714 and 716, a portion of the output of which is sent as balanced detection outputs to spectral detection units (not shown, but as described elsewhere herein) and the remainder of the output is sent to the phase tracker assembly 720. In the phase tracker assembly 720, phase tracker detectors $D_1$ and $D_2$, 722 and 724, receive the partial output of the pair of splitters 714 and 716, which in turn send signal to a mixer 726 to generate an error signal. A processing unit 728 processes the error signal, where the sum generation of offset voltage and adds this to the modulation signal 730 to generate the output for the phase modulator driver 732. Modulation signal, shown at box 730, is forwarded to the mixer 726 and the processing unit 726. In addition, the fringe amplitude could be too small for the phase tracker to lock. Alternatively, a secondary source with longer coherence length can be coupled to the system 700, e.g., to provide a larger fringe amplitude to the phase tracker.

Figure 14A:
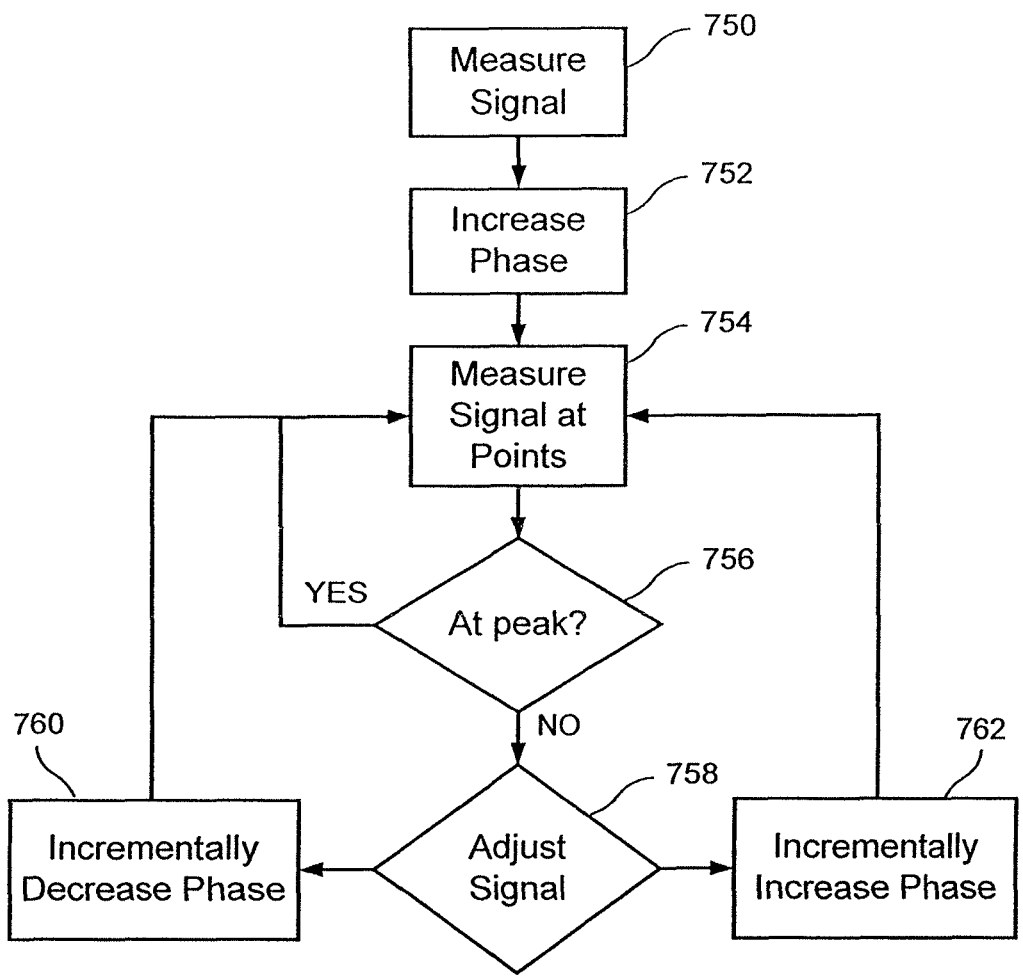
Figure 14B:
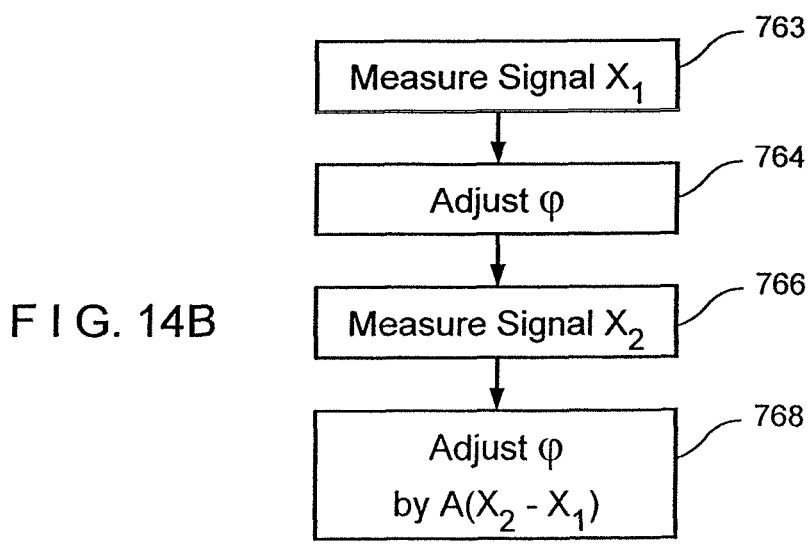

FIGS. 14A-14C show an exemplary embodiment of a method for tracking phase in an imaging system begins in processing blocks 750 and 752 according to the present disclosure by measuring a signal received from the sample arm (also see block 763 of FIG. 14B and block 770 of FIG. 14C), and then increasing a phase of the signal (also see block 764 of FIG. 14B where the phase is adjusted and block 772 of FIG. 14C where the phase is increased). Processing of this exemplary method then proceeds to block 754 of FIG. 14A, in which a first signal partition of the signal defined as $x_1$ is measured at least one peak of the signal. In decision block 756, a determination is as to whether the signal defined as $x_1$ has been measured at least one peak of the signal. If in decision block 756, it is determined that the signal defined as $x_1$ has been measured at at least one peak of the signal, then processing returns to block 754 and the signal is again measured.

On the other hand, if in decision block 756, it is determined that the signal defined as $x_1$ has not been measured at at least one peak of the signal, then processing flows to a decision block 758, where a determination is made as to whether to adjust the signal. The adjustment may be, e.g., an increase or a decrease in the phase of the signal by an incremental amount as shown in blocks 760 and 762. Regardless of whether an increase or a decrease in the phase of the signal is made, processing returns to processing block 754, where a second signal partition of the signal is measured at its peak. Blocks 756-762 are then repeated for such measured signal. It should be noted that the functions of blocks 750-762 may be performed in parallel and/or series with other imaging processes.

As shown in FIGS. 14B and 14C, the adjustment of phase "ϕ" can be defined as $A(x_2-x_1)$, where "A" is a constant. For example, FIGS. 14B and 14C illustrate other exemplary embodiments of the method for tracking phase in the imaging system. As shown in FIG. 14B, a signal $x_1$ can be received and measured from the sample arm in block 763, and then a phase ϕ of the signal $x_1$ is adjusted in block 764. Then, in this exemplary embodiment, another signal $x_2$ be received and measured from the sample arm in block 766 and then a phase ϕ of such signal $x_2$ is adjusted in block 764 by $A(x_2-x_1)$. Turning to the exemplary embodiment of FIG. 14C, the signal $x_1$ can be received and measured from the sample arm in block 770, and then a phase ϕ of the signal $x_1$ is increases in block 770. Then, in this further exemplary embodiment, determining whether to increase or decrease the phase of the signal $x_2$ by a incremental amount may further comprise the substeps of (1) determining whether $A(x_2-x_1)$ —shown in block 776— is within the range of the phase modulator—see block 778; and 2) changing ϕ by an amount equal to $A(x_2-x_1)$ if $A(x_2-x_1)$ is within the range (block 782) or changing ϕ by an amount equal to $A(x_2-x_1)-m2\pi$ if $A(x_2-x_1)$ is outside of the range, where M is an integer greater than 1 (block 782). The exemplary method may optionally further comprise a substep (3) re-measuring signal $x_1$.

d. Data Processing

In general, the data recorded by the detector in time may not be sampled as a strictly linear function of the optical frequency ω or wave number k. The Fourier transform, however, can link z and k space (or t and ω). Because of the non-linear sampling in k, the acquired spectrum is interpolated to create evenly spaced samples in the k domain. Alternatively, the tuning slope of the laser could be adjusted in such a way that the light is samples in equal intervals in k space, such that the interpolation becomes obsolete. Alternatively, the detection timing could be designed to sample the light evenly spread in the k domain, such that the interpolation becomes obsolete. To achieve the optimal point spread function, dispersion in the sample and reference arm of the interferometer should preferably be balanced. Dispersion imbalance can also be corrected by digital processing. Phase chirping induced by motions can also be corrected by digital processing. For the motion artifact correction, the axial movement of the sample is measured, and a proper nonlinear mapping can be calculated from the velocity of the movement.

Various interpolation techniques are known to those having ordinary skill in the art. This includes, but is not limited to, simple two-point interpolation, FFT zero-padding followed by two-point interpolation, and rigorous interpolation with the sinc function dictated by the Nyquist theorem.

An exemplary embodiment of the present invention may also provide a probe for locating atherosclerotic plaque in a blood vessel, comprising: an interferometer; a spectral separating unit which splits signal received from the interferometer into a plurality of optical frequencies; and a detector arrangement capable of detecting at least a portion of the optical frequencies received from the spectral separating unit.

e. Frequency Shifting Technique

For high-speed OFDI techniques, the maximum ranging depth can likely be limited by the finite width of the coherence function of the laser output because the coherence length is often compromised to obtain higher tuning speed, higher output power, or wider tuning range. The finite coherence length may cause the visibility of the interference fringe to decrease as the path length difference of the interferometer increases. This result in the degradation of SNR, and therefore limits the maximum ranging depth. Furthermore, the inability to distinguish between a positive and negative electrical frequency in a conventional interferometry may lead to the ambiguity between positive and negative depths. To avoid the imaging folding artifact, the reference delay of the interferometer should be adjusted so that the image presents at only either positive or negative depth. This further may limit the ranging depth for a given coherence length of the source.

To avoid such possible limitation, quadrature interference signals have been measured based on active or passive phase biasing using a piezoelectric actuator, birefringence plate or 3×3 coupler. These techniques may provide otherwise overlapping images associated with positive and negative depths, but tended to leave significant residual artifacts due to the difficulty of producing stable quadrature signals. In this paper, we propose and demonstrate a simple technique that effectively eliminates the ambiguity between positive and negative depths.

The exemplary technique according to the exemplary embodiment of the present invention uses an optical frequency shifter in the interferometer to provide a constant frequency shift of the detector signal. This allows both sides of the coherence range to be used without crosstalk, and can double the ranging depth. The same concept has been described above in the context of 1-dimensional optical frequency domain reflectometry using rotating birefringence plates at 58 Hz or a recirculating frequency shifting loop. In this exemplary embodiment, an acousto-optic frequency shifter is used, and the technique is applied to high-speed OFDI with several orders of magnitude faster ranging speed. Furthermore, a signal processing technique according to a further exemplary embodiment of the present invention is provided to accommodate a nonlinear tuning slope of the swept source in the frequency shifting technique.

A. Principle

Frequency Shift

FIG. 15 shows a high level diagram of the OFDI system according to the present invention which includes a wavelength-swept source 95, singlemode-fiber interferometer employing an optical frequency shifter 311 in a reference arm 80, a photodetector 88, and a signal processor 160. With a roundtrip frequency shift of Δf in the reference arm, the photocurrent associated with the interference between the reference and sample light can be expressed as $$t_s(t) = \eta\sqrt{P_r(t)P_s(t)} \int \sqrt{R(z)}\, G(|z|)\cos\left[\frac{4\pi}{c}v(t)z + \phi(z) + 2\pi\Delta f t\right]dz,$$

where $\eta$ denotes the quantum efficiency of the detector, Pr(t) and Ps(t) the optical powers of the reference and sample arm light, respectively, R(z) the reflectivity profile of the sample, G(|z|) the coherence function corresponding to the fringe visibility, c the speed of light, v(t) the optical frequency, and $\phi(z)$ the phase of backscattering. In the case of a linear tuning, i.e. v(t)=0-1t, the frequency of the detector signal is given by $$f_s = \left|v_1\frac{2z}{c} - \Delta f\right|$$

The zero signal frequency corresponds to a depth z=c$\Delta$f/(2v1). Therefore, by choosing the direction of frequency shifting same as the tuning direction of the swept source, the zero signal frequency can be made to point to a negative depth. FIGS. 16(a) and 16(b) illustrate the effect of the frequency shift. The fringe visibility or the coherence function has a peak value at the zero depth and decrease as the depth increases. The coherence length $z_c$ indicates the depth where the visibility drops to 0.5 and thereby the SNR drops by 6 dB. One may arguably define the effective ranging depth as the maximum depth span where the SNR penalty is less than 6 dB. For example, in FIG. 16(a), a single side of the coherence range can be used due to the sign ambiguity of the signal frequency (hatched region). In contrast, as shown in FIG. 16(b), with an appropriate frequency shift, both sides of the coherence range from $-z_c$ to $z_c$ can be utilized without any image crosstalk between the negative and positive depths.

Nonlinear Tuning

Nonlinearity in v(t) with respect to time results in frequency chirping of the signal at a constant depth and causes the degradation of axial resolution. As a solution to this problem, the detector signal may be sampled with nonlinear time interval compensating for the frequency chirping. Alternatively, the detector signal can be sampled with a constant time interval, and then the sampled data be mapped to a uniform v-space by interpolation prior to discrete Fourier transform ("DFT"). Both methods have been demonstrated to yield a transform-limited axial resolution. However, these methods are not applicable directly in the frequency shifting technique. Both the nonlinear sampling and interpolation method can result in artificial chirping of the frequency shift, leading to sub optimal axial resolution. Thus, a modified interpolation method can be used to achieve nearly transform-limited axial resolution over the entire ranging depth. The exemplary technique may be as follows:

Step 1. Obtain N samples of the signal with uniform time interval during each wavelength sweep of the source.
Step 2. Produce DFT of N data points in the electrical frequency domain.
Step 3. Separate two frequency bands below and above $\Delta f$ corresponding to negative and positive depths, respectively.
Step 4. Shift each frequency band such that the zero depth is aligned to the zero electrical frequency.
Step 5. Apply zero-padding to each frequency band and perform inverse DFT resulting in an array of increased number of samples in the time domain with smaller time interval for each frequency band.
Step 6. Interpolate each array in the time domain into a uniform v space using a proper mapping function given by the nonlinearity of the swept source.
Step 7. Conduct DFT of each interpolated array.
Step 8. Combine the two arrays (images) by shifting the array index.

As a result, the zero depth lies at the electrical frequency of $\Delta f$.

B. Experiment

OFDI System

Figure 17:
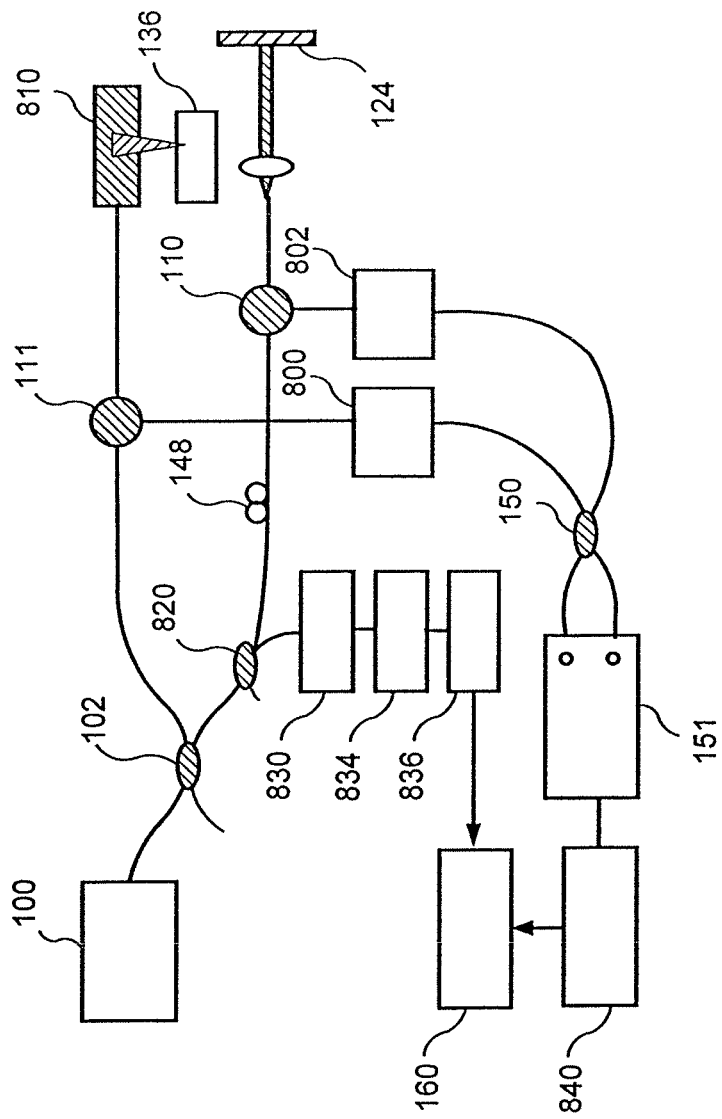
FIG. 17 is a block diagram of the OFDI system employing two acousto-optic frequency shifters according to still another exemplary embodiment of the present invention.

FIG. 17 depicts the experimental setup of an exemplary OFDI system employing two acousto-optic frequency shifters (FS1 800 and FS2 802, Brimrose Inc. AMF-25-1.3) according to an exemplary embodiment of the present invention. The two frequency shifters may be driven with voltage controlled oscillators to produce a net shift of $\Delta f$=FS2−FS1. The use of two frequency shifters balanced the material dispersion of the acousto-optic crystals automatically. The insertion loss of each device including fiber coupling may be less than 2.5 dB. The sampling rate of the digitizer can be 10 MHz. The swept laser 100 may be constructed to provide a tuning range of 108 nm centered swept from 1271 nm to 1379 nm (v 1=135 GHz/µs). Although a repetition rate up to 36 kHz could be achieved, the laser was operated at a reduced rate of 7 kHz and 1300 samples were acquired during a single wavelength sweep. This resulted in a depth span of 5.8 mm in the image corresponding to the Nyquist frequency of 5 MHz. The probe 810 may include a galvanometer mirror and an imaging lens produced a probe beam with a confocal parameter of 1.1 mm. An optical tap coupler 820 can be used in conjunction with a narrowband filter 830 and a photodetector 834 to generate a TTL trigger signal in an electrical circuit 836. The TTL signal may be used as a trigger in analog to digital conversion.

The interference signal can be measured using a dual balanced receiver 151. The detector signal was further processed prior to digitization using a low pass electrical filter 840. Other types of electrical filters such as a band pass filter and a slope filter. The transmission of the slope filter may have an exponentially-rising (falling) slope in its low frequency band. This filter may be useful in which attenuation is significant and the resulting signal strength decays with depth. The slope filter can improve the dynamic range of the detection by effectively suppressing the large signal from the surface relative to that at greater depths.

To characterize the coherence function of the swept laser 100, the point spread function of the system may be measured at $\Delta f$=0 (FS1=−25 MHz, FS2=−25 MHz) with a partial reflector at various locations of the reference mirror. For comparison, the sampled data acquired at each depth was processed with and without the mapping process. FIGS. 18(a) and 18(b) show exemplary results, where the y-axis represents the square of the DFT amplitudes normalized to the value at zero frequency, and the bottom and top x-axes represent the signal frequency and the depth z, respectively. Without mapping, the point spread function suffers from significant broadening and large degradation of the peak power as the depth increases, because of the nonlinearity of our swept laser [see FIG. 18(a)]. With the mapping process, however, the spread function exhibits nearly transform-limited axial resolution as shown in FIG. 18(b). The finite coherence length of the laser output accounts for the decrease of the signal power depth. Over the entire depth span of 5.8 mm, the SNR is reduced by more than 11 dB. According to the criterion for the effective ranging depth introduced earlier, the depth corresponding to the coherence length may be only 2.9 mm, a half the total in the image. The same experiment was conducted with a non-zero frequency shift of $\Delta f$=−2.5 MHz (FS1=−22.5 MHz, FS2=−25 MHz). FIGS. 18(c) and 18(d) show the point spread functions measured with and without the mapping process, respectively. As shown in these figures, the peak of the signal power occurring at the zero depth present at a frequency of 2.5 MHz is at least approximately equal to the net acousto-optic frequency shift. The nearly transform-limited axial resolution observed in FIG. 18(d) validates the mapping technique. The reduction in the signal power is less than 5 dB over the entire depth span of 5.8 mm, demonstrating the benefit of the frequency shifting technique in terms of extending the ranging depth.

Image

Exemplary imaging of a human lung tissue ex vivo was conducted with the OFDI system. FIGS. 19A and 19B depict two images/graphs, obtained under identical experimental conditions except that Δf=0 for the image/graph in FIG. 19A and Δf=−2.5 MHz for the image/graph in FIG. 19B. Each image/graph was obtained using the mapping technique described above. The surface of the tissue was placed with an angle with respect to the probe beam axis, and the reference mirror was positioned such that the signal was present at both positive and negative depths in the image. In FIG. 19A, the tissue image is contained within the effective ranging depth of 2.8 mm, i.e. the top half of the total depth span. However, the relatively large variation in the sample location resulted in the imaging folding artifact. In contrast, in FIG. 19B the entire positive and negative depths could be displayed without ambiguity taking advantage of the ranging depth increased to 5.8 mm by the frequency shifting technique.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention.

The invention claimed is:

1. An apparatus, comprising:
   at least one first arrangement configured to provide at least one first electro-magnetic radiation directed to a sample and at least one second electro-magnetic radiation directed to a reference, wherein a frequency of the radiation provided by the at least one first arrangement varies over time; and
   at least one second arrangement configured to detect an interference between at least one third radiation associated with the at least one first radiation and at least one fourth radiation associated with the at least one second radiation to generate an electrical first signal,
   wherein the at least one second arrangement is configured to obtain a second signal associated with at least one phase of at least one frequency component of the electrical first signal, and wherein the at least one second arrangement includes a computing arrangement which compares the second signal to at least one particular information.

2. The apparatus according to claim 1, wherein the at least one second arrangement is configured to determine a third signal associated with at least one further phase of at least one further frequency component of the electrical first signal, and wherein the at least one particular information is the third signal.

3. The apparatus according to claim 1,
   wherein the at least one second arrangement is configured to determine a third signal associated with at least one further phase of at least one further frequency component of a further electrical signal, the further electrical signal being different from the electrical first signal, and wherein the at least one particular information is the third signal.

4. The apparatus according to claim 3, wherein the electrical first signal and the further electrical signal are obtained at different times.

5. The apparatus according to claim 3, wherein the electrical first signal and the further electrical signal are obtained at different locations of the sample.

6. The apparatus according to claim 1, wherein the at least one second arrangement includes at least one third arrangement that includes an interferometric arrangement.

7. A method comprising:
   providing at least one first electro-magnetic radiation directed to a sample and at least one second electro-magnetic radiation directed to a reference, wherein a frequency of the radiation varies over time;
   detecting an interference between at least one third radiation associated with the at least one first radiation and at least one fourth radiation associated with the at least one second radiation to generate an electrical first signal;
   obtaining a second signal associated with at least one phase of at least one frequency component of the electrical first signal; and
   comparing the second signal to at least one particular information.

8. The method according to claim 7, further comprising determining a third signal associated with at least one further phase of at least one further frequency component of the electrical first signal, and wherein the at least one particular information is the third signal.

9. The method according to claim 8, further comprising:
   determining a third signal associated with at least one further phase of at least one further frequency component of a further electrical signal, the further electrical signal being different from the electrical first signal,
   wherein the at least one particular information is the third signal.

10. The method according to claim 9, wherein the electrical first signal and the further electrical signal are obtained at different times.

11. The method according to claim 9, wherein the electrical first signal and the further electrical signal are obtained at different locations of the sample.

12. The method according to claim 7, wherein the second signal is an interferometric signal.

13. A system comprising:
    at least one arrangement configured to (i) detect an interference between at least one first radiation associated with a first split portion of a radiation received from a sample and a second split portion of the radiation received from a reference and (ii) to generate an electrical first signal associated with the interference, wherein a frequency of the radiation varies over time, and wherein the at least one arrangement is configured to obtain a second signal associated with at least one phase of at least one frequency component of the electrical first signal, and wherein the at least one arrangement includes a computing arrangement which compares the second signal to at least one particular information.

14. The apparatus according to claim 13, wherein the at least one arrangement is configured to obtain a third signal corresponding to the electrical first signal between the first and second split portions of the radiation, and wherein the second signal is associated with at least one phase of at least one frequency component of an additional electrical signal associated with the third signal.

* * * * *